(12) United States Patent
Blattmann et al.

(10) Patent No.: US 7,968,342 B2
(45) Date of Patent: Jun. 28, 2011

(54) MUTANT E. COLI APPA PHYTASE ENZYMES AND NATURAL VARIANTS THEREOF, NUCLEIC ACIDS ENCODING SUCH PHYTASE ENZYMES, VECTORS AND HOST CELLS INCORPORATING SAME AND METHODS OF MAKING AND USING SAME

(75) Inventors: Beat O Blattmann, Richterswil (CH); Aldis Darzins, Highlands Ranch, CO (US); John M. Davis, Houston, TX (US); Lance P. Encell, Madison, WI (US); Thomas B. Morrison, Winchester, MA (US); Gregory T. Mrachko, San Diego, CA (US); Volker Schellenberger, Palo Alto, CA (US)

(73) Assignee: Danisco US Inc., Palo Alto, CA (US)

(*) Notice: Subject to any disclaimer, the term of this patent is extended or adjusted under 35 U.S.C. 154(b) by 697 days.

(21) Appl. No.: 10/524,234

(22) PCT Filed: Aug. 11, 2003

(86) PCT No.: PCT/US03/25058
§ 371 (c)(1),
(2), (4) Date: Dec. 1, 2005

(87) PCT Pub. No.: WO2004/015084
PCT Pub. Date: Feb. 19, 2004

(65) Prior Publication Data
US 2006/0141562 A1 Jun. 29, 2006

Related U.S. Application Data

(60) Provisional application No. 60/403,330, filed on Aug. 12, 2002.

(51) Int. Cl.
*C12N 15/55* (2006.01)
*C12N 9/16* (2006.01)
(52) U.S. Cl. .................. 435/471; 435/440; 435/196
(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,034,506 A | 7/1991 | Summerton et al. | |
| 5,235,033 A | 8/1993 | Summerton et al. | |
| 5,510,471 A | 4/1996 | Lebrun et al. | |
| 5,571,706 A | 11/1996 | Baker et al. | |
| 5,644,048 A | 7/1997 | Yau | |
| 5,750,871 A | 5/1998 | Moloney et al. | |
| 5,773,269 A | 6/1998 | Somers et al. | |
| 5,876,997 A | 3/1999 | Kretz | |
| 6,039,942 A | 3/2000 | Lassen et al. | |
| 6,066,725 A | 5/2000 | DeBoer et al. | |
| 6,110,719 A | 8/2000 | Kretz | |
| 6,139,902 A | 10/2000 | Kondo et al. | |
| 6,190,897 B1 | 2/2001 | Kretz | |
| 6,221,644 B1 | 4/2001 | Berka et al. | |
| 6,261,592 B1 | 7/2001 | Nagashima et al. | |
| 6,720,014 B1 * | 4/2004 | Short et al. | ............ 426/52 |
| 6,855,365 B2 | 2/2005 | Short et al. | |

FOREIGN PATENT DOCUMENTS

| | | |
|---|---|---|
| EP | 0 684 313 | 11/1995 |
| WO | WO 87/05330 | 9/1987 |
| WO | WO 01/36607 | 5/2001 |
| WO | WO 01/09333 | 11/2001 |
| WO | WO 02/48332 A2 | 6/2002 |

OTHER PUBLICATIONS

J.C. van der Laan et al. "Cloning, Charcterization, and Multiple Chromosomal Integration of a Bacillus Alkaline Protease Gene", Appl. Environ. Microbiol. 57(4): 901-909. (Apr. 1991).*
Al-Batshan, H.A. et al. ,"Duodenal calcium uptake, femur ash, and eggshell quality decline with age and increase following molt," *Poultry Science*, 73(10):1590-6, 1994.
Altschul, S.F. et al., "Basic local alignment search tool," *J. Mol. Biol.*, 215(3): 403-410, 1990.
Altschul, S.F. et al., "Gapped BLAST and PSI-BLAST: a new generation of protein database search programs," *Nucleic Acids Res.*, 25(17):3389-3402, 1997.
Aplin, J.D. et al., "Preparation, Properties, and Applications of Carbohydrate Conjugates of Proteins and Lipids," *Critical Reviews in Biochemistry*, 10(4): 259-306, 1981.
Beaucage, S.L. et al., "Deoxynucleoside phosphoramidites—A new class of key intermediates for deoxypolynucleotide synthesis," *Tetrahedron Lett.*, 22(20):1859-1862, 1981.
Benton, W.D. et al., "Screening λgt recombinant clones by hybridization to single plaques in situ," *Science*, 196(4286):180-182, 1977.
Birnboim, H. C. et al. "A rapid alkaline extraction procedure for screening recombinant plasmid DNA," *Nucl. Acids Res.*, 7(6): 1513-1523, Nov. 24, 1979.
Bolli, M. et al.,"α-Bicyclo-DNA: Synthesis, Characterization, and Pairing Properties of α-DNA-Analogues with Restricted Conformational Flexibility in the Sugar-Phosphate Backbone," In *Carbohydrate Modifications in Antisense Research*, edited by Y.S. Sanghvi et al., pp. 100-117. Washington, D.C.: American Chemical Society, 1994.
Botstein, D. et al., "Strategies and applications of in vitro mutagenesis," *Science*, 229(4719): 1193-1201, 1985.
Brill, W.K.D. et al., "Synthesis of oligodeoxynucleoside phosphorodithioates via thioamidites," *J. Am. Chem. Soc.*, 111(6): 2321-2322, 1989.
Brisson, N. et al., "Plant Virus Vectors: Cauliflower Mosaic Virus," In *Methods for Plant Molecular Biology*, edited by A. Weissbach et al., pp. 437-463. New York: Academic Press, 1988.
Brisson, N. et al., "Expression of a bacterial gene in plants by using a viral vector," *Nature*, 310(5977): 511-514, 1984.

(Continued)

*Primary Examiner* — Rebecca E. Prouty

(57) ABSTRACT

Cells producing mutant phytases having modified activity are provided, as well as the phytases so produced. Also provided are methods of making and producing such phytases and the use of the expressed phytase protein in feed as a supplement.

3 Claims, 22 Drawing Sheets

OTHER PUBLICATIONS

Broglie, R. et al., "Light-regulated expression of a pea ribulose-1,5-bisphosphate carboxylase small subunit gene in transformed plant cells," *Science*, 224(4651): 838-43, 1984.

Cadwell, R.C. et al., "Randomization of genes by PCR mutagenesis," *PCR Methods Appl.*, 2(1): 28-33, 1992.

Carlsson, C. et al., "Screening for genetic mutations," *Nature*, 380(6571):207, 1996.

Clunies, M. et al.,"Effect of dietary calcium level on plasma proteins and calcium flux occurring during a 24 h ovulatory cycle," *Can. J. Anim. Sci.*, 75(3): 439-444, 1995.

Committee on Food Chemicals Codex, "Phytase Activity," In *Food Chemicals Codex*, pp. 808-810, Washington, D.C., National Academy Press, 1996.

Coruzzi, G. et al., "Tissue-specific and light-regulated expression of a pea nuclear gene encoding the small subunit, of ribulose-1,5-bisphosphate carboxylase," *The EMBO Journal*, 3(8): 1671-1679, 1984.

Creighton, T.E., *Proteins: Structures and Molecular Principles*, pp. 79-86, San Francisco, W.H. Freeman & Co., 1983.

Cromwell, G.L. et al., "Phosphorus—a key essential nutrient, yet a possible major pollutant—its central role in animal nutrition," In *Biotechnology in the feed industry*, edited by T.P. Lyons, pp. 133-145, Nicholasville, KY: Alltech Tehcnical, 1991.

Cromwell, G.L. et al., "Efficacy of phytase in improving the bioavailability of phosphorus in soybean meal and corn-soybean meal diets for pigs," *J. Anim. Sci.*, 71(7): 1831-1840, 1993.

Damron, B.L. et al., "Calcium supplementation of hen drinking water," *Poult Sci.*, 74(5): 784-787, 1995.

Dassa, J. et al., "The complete nucleotide sequence of the *Escherichia coli* gene appA reveals significant homology between pH 2.5 acid phosphatase and glucose-1-phosphatase," *J. Bacteriol.*, 172(9): 5497-5500, 1990.

Dayhoff, M.O. et al. "A Model of Evolutionary Change in Proteins," In *Atlas of Protein Sequence and Structure*, edited by M.O. Dayhoff, 5 supp. 3, pp. 345-352, Silver Spring, MD, National Biomedical Research Foundation, 1978.

Dempcy, R.O. et al., "Synthesis of a thymidyl pentamer of deoxyribonucleic guanidine and binding studies with DNA homopolynucleotides," *Proc. Natl. Acad. Sci. U.S.A.*, 92(13): 6097-6101, 1995.

Eckert, K.A. et al., "DNA polymerase fidelity and the polymerase chain reaction," *PCR Methods Appl.*, 1(1): 17-24, 1991.

Edge, A.S.B. et al., "Deglycosylation of glycoproteins by trifluoromethanesulfonic acid," *Analytical Biochemistry* 118(1): 131-137, 1981.

Egholm, M. et al. "PNA hybridizes to complementary oligonucleotides obeying the Watson-Crick hydrogen-bonding rules," *Nature*, 365(6446): 566-568, 1993.

Egholm, M. et al., "Peptide nucleic acids (PNA). Oligonucleotide analogues with an achiral peptide backbone," *Journal of the American Chemical Society*, 114(5): 1895-1897, 1992.

Ehrlich, K.C. et al., "Identification and cloning of a second phytase gene (phyB) from *Aspergillus niger* (ficuum)," *Biochemical and Biophysical Research Communications*, 195(1): 53-57, 1993.

Elander, R.P. "Microbial screening, selection and strain improvement," In *Basic Biotechnology*, edited by J. Bu'Lock et al., pp. 217-251, New York: Academic Press, 1987.

Evan, G.I. et al., "Isolation of monoclonal antibodies specific for human c-myc proto-oncogene product," *Molecular and Cellular Biology*, 5(12): 3610-3616, 1985.

Field, J. et al., "Purification of a RAS-responsive adenylyl cyclase complex from *Saccharomyces cerevisiae* by use of an epitope addition method," *Molecular and Cellular Biology*, 8(5):2159-2165, 1988.

Finkelstein, D.B., "Transformation," In *Biotechnology of Filamentous Fungi: Technology and Products*, edited by D.B. Finkelstein et al., pp. 113-156, Boston, MA: Butterworth-Heinemann, 1992.

Fiske, C.H. et al., "The Colorimetric Determination of Phosphorus," *J. Blol. Chem.*, 66: 375-400, 1925.

Fraser, C.M. et al., "Fish," In *The Merck veterinary manual: a handbook of diagnosis, therapy, and disease prevention and control for the veterinarian*, pp. 1268-1269, Rahway, N. J.: Merck & Co., 1991.

Fromant, M. et al., "Direct random mutagenesis of gene-sized DNA fragments using polymerase chain reaction," *Anal. Biochem.*, 224(1): 347-353, 1995.

Fungaro, M.H.P. et al.,"Transformation of *Aspergillus nidulans* by microprojectile bombardment on intact conidia," *FEMS Microbiology Letters*, 125(2-3): 293-297, 1995.

Gao, X. et al., "Unusual conformation of a 3'-thioformacetal linkage in a DNA duplex," *J. Biomol. NMR*, 4(1): 17-34, 1994.

Gelvin, S.B. et al., "vir genes influence conjugal transfer of the Ti plasmid of *Agrobacterium tumefaciens*," *J. Bacteriol.*, 172(3): 1600-1608, 1990.

Gish, W. et al., "Identification of protein coding regions by database similarity search," *Nat. Genet.*, 3(3): 266-272, 1993.

Golovan, S. et al., "Characterization and overproduction of the *Escherichia coli* appA encoded bifunctional enzyme that exhibits both phytase and acid phosphatase activities," *Can. J. Microbiol.*, 46(1): 59-71, 2000.

Greiner, R. et al., "Purification and characterization of two phytases from *Escherichia coli*," *Arch. Biochem. Biophys.*, 303(1):107-113, 1993.

de Groot, M.J.A. et al., "*Agrobacterium tumefaciens*-mediated transformation of filamentous fungi," *Nat. Biotech.* 16(9): 839-842, 1998.

Grunstein, M. et al., "Colony Hybridization: A Method for the Isolation of Cloned DNAs that Contain a Specific Gene," *Proc. Natl. Acad. Sci. U.S.A.*, 72(10): 3961-3965, 1975.

Harayama, S., "Artificial evolution by DNA shuffling," *Trends Biotechnol.*, 16(2): 76-82, 1998.

van Hartingsveldt, W. et al., "Cloning, characterization and overexpression of the phytase-encoding gene (phyA) of *Aspergillus niger*," *Gene*, 127(1): 87-94, 1993.

Henikoff, S. et al., "Amino Acid Substitution Matrices from Protein Blocks," *Proc. Natl. Acad. Sci. USA*, 89: 10915-10919, 1992.

Henke, E. et al., "Directed Evolution of an Esterase from *Pseudomonas fluorescens*. Random Mutagenesis by Error-Prone PCR or a Mutator Strain and Identification of Mutants Showing Enhanced Enantioselectivity by a Resorufin-Based Fluorescence Assay," *Biological Chemistry*, 380(7-8):1029-1033, 1999.

Herdewijn, P. et al., "Hexopyranosyl-Like Oligonucleotides," In *Carbohydrate Modifications in Antisense Research*, edited by Y.S. Sanghvi et al., pp. 80-99. Washington, D.C., American Chemical Society, 1994.

Higgins, D.G. et al., "CLUSTAL V: improved software for multiple alignment," *CABIOS* 8: 189-191, 1992.

Hopp, T.P. et al., "A Short Polypeptide Marker Sequence Useful for Recombinant Protein Identification and Purification," *Nat. Biotech.*, 6(10): 1204-1210, 1988.

Horn, T. et al. "Oligonucleotides with alternating anionic and cationic phosphoramidate linkages: Synthesis and hybridization of stereo-uniform isomers," *Tetrahedron Letters*, 37(6): 743-746, 1996.

Inoue, H. et al., "High efficiency transformation of *Escherichia coli* with plasmids," *Gene*, 96(1): 23-28, 1990.

Jenkins, G.N. et al., "The biosynthesis of carbocyclic nucleosides," *Chem. Soc. Rev.*, 24(3): 169-176, 1995.

Jeroch, V.H. et al., "Zur Wirksamkeit Mikrobieller Phytase zu Legehennenrationen auf Mais-bzw. Weizenbasis," *Die Bodenkultur*, 45: 361-368, 1994.

Jung, P.M. et al., "Hybridization of Alternating Cationic/Anionic Oligonucleotides to RNA—Segments," *Nucleotides and Nucleosides*, 13(6 and 7):1597-1605, 1994.

Karlin, S. et al., "Applications and statistics for multiple high-scoring segments in molecular sequences," *Proc. Natl. Acad. Sci. USA*, 90(12): 5873-5877, 1993.

Kerovuo, J. et al., "Isolation, Characterization, Molecular Gene Cloning, and Sequencing of a Novel Phytase from *Bacillus subtilis*," *Appl. Environ. Microbiol.*, 64(6): 2079-2085, 1998.

Kerovuo, J. et al. "Analysis of myo-inositol hexakisphosphate hydrolysis by *Bacillus phytase*: indication of a novel reaction mechanism," *Biochemical Journal*, 352(Pt 3): 623-628, 2000.

Kiedrowski, G. et al., "Parabolic Growth of a Self-Replicating Hexadeoxynucleotide Bearing a 3'-5'-Phosphoamidate Linkage," *Angewandte Chemie International Edition in English*, 30(4):423-426, 1991.

Kornegay, E.T. et al., "Response of Broilers to Graded Levels of Microbial Phytase Added to Maize-soyabean-Meal-Based Diets Containing Three Levels of Non-Phytate Phosphorus," *British Journal of Nutrition*, 75(06): 839-852, 1996.

Kostrewa, D. et al., "Crystal structure of phytase from *Aspergillus ficuum* at 2.5 Å resolution," *Nat. Struct Mol. Biol.* 4(3):185-190, 1997.

Lehmann, M. et al., "From DNA sequence to improved functionality: using protein sequence comparisons to rapidly design a thermostable consensus phytase," *Protein Eng.*, 13(1): 49-57, 2000.

Letsinger, R.L. et al., "Effects of pendant groups at phosphorus on binding properties of d-ApA analogues," *Nucleic Acids Res.*, 14(8): 3487-3499, 1986.

Letsinger, R.L. et al., "Phosphoramidate analogs of oligonucleotides," *J. Org. Chem.*, 35(11):3800-3803, 1970.

Letsinger, R.L. et al., "Cationic oligonucleotides," *J. Am. Chem. Soc.*, 110(13): 4470-4471, 1988.

Leung, D.W. et al., "A method for random mutagenesis of a defined DNA segment using a modified polymerase chain reaction," *Technique*, 1(1): 11-15, 1989.

Lim, D. et al., "Crystal structures of *Escherichia coli* phytase and its complex with phytate," *Nat. Struct Mol. Biol.* 7(2):108-113, 2000.

Ling, M.M. et al., "Approaches to DNA mutagenesis: an overview," *Anal. Biochem.*, 254(2): 157-178, 1997.

Lutz-Freyermuth, C. et al., "Quantitative determination that one of two potential RNA-binding domains of the A protein component of the U1 small nuclear ribonucleoprotein complex binds with high affinity to stem-loop II of U1 RNA," *Proc. Natl. Acad. Sci. U.S.A.*, 87(16):6393-6397, 1990.

Madden, T.L. et al., "Applications of network BLAST server," *Meth. Enzymol.*, 266:131-41, 1996.

Maddry, J.A. et al., "Synthesis of Nonionic Oligonucleotide Analogues," In *Carbohydrate Modifications in Antisense Research*, edited by Y.S. Sanghvi et al., pp. 40-51, Washington, D.C., American Chemical Society, 1994.

Mag, M. et al. "Synthesis and selective cleavage of an oligodeoxynucleotide containing a bridged internucleotide 5'-phosphorothioate linkage," *Nucleic Acids Res.*, 19(7):1437-1441, 1991.

Martin, G.A. et al., "GAP domains responsible for ras p21-dependent inhibition of muscarinic atrial K+ channel currents," *Science*, 255(5041):192-194, 1992.

Meier, C. et al., "Peptide Nucleic Acids(PNAs)—Unusual Properties of Nonionic Oligonucleotide Analogues," *Angewandte Chemie International Edition in English*, 31(8):1008-1010, 1992.

Melnikov, A. et al., "Random mutagenesis by recombinational capture of PCR products in *Bacillus subtilis* and cinetobacter calcoaceticus," *Nucl. Acids Res.*, 27(4):1056-1062, 1999.

de Mesmaeker, A. et al., "Comparison of rigid and flexible backbones in antisense oligonucleotides," *Bioorganic & Medicinal Chemistry Letters*, 4(3): 395-398, 1994.

de Mesmaeker, A. et al., "Novel Backbone Replacements for Oligonucleotides," In *Carbohydrate Modifications in Antisense Research*, edited by Y.S. Sanghvi et al., pp. 24-39, Washington, D.C., American Chemical Society, 1994.

Mitchell, D.B. et al., "The phytase subfamily of histidine acid phosphatases: isolation of genes for two novel phytases from the fungi *Aspergillus terreus* and *Myceliophthora thermophila*," *Microbiology*, 143(1): 245-252, 1997.

Murry, L.E. "Genetic Engineering." In *McGraw Hill Yearbook of Science and Technology*, pp. 189-196. New York, McGraw Hill, 1992.

Myers, R.M. et al., "A general method for saturation mutagenesis of cloned DNA fragments," *Science*, 229(4710):242-247, Jul. 19, 1985.

Needleman, S.B. et al., "A general method applicable to the search for similarities in the amino acid sequence of two proteins," *J. Mol. Biol.*, 48(3):443-453, 1970.

Oakley, B.R. et al., "Cloning, mapping and molecular analysis of the pyrG (orotidine-5'-phosphate decarboxylase) gene of *Aspergillus nidulans*," *Gene*, 61(3): 385-399, 1987.

Ostanin, K. et al., "Overexpression, site-directed mutagenesis, and mechanism of *Escherichia coli* acid phosphatase," *J. Biol. Chem.*, 267(32):22830-22836, 1992.

Ostanin, K. et al., "Asp$^{304}$ of *Escherichia coli* acid phosphatase is involved in leaving group protonation," *J. Biol. Chem.*, 268(28):20778-20784, 1993.

Paborsky, L.R. et al., "Mammalian cell transient expression of tissue factor for the production of antigen," *Protein Eng.*, 3(6):547-553, 1990.

Pandey, A. et al., "Production, purification and properties of microbial phytases," *Bioresource Technology*, 77(3):203-214, 2001.

Pasamontes, L. et al., "Cloning of the phytases from *Emericella nidulans* and the thermophilic fungus *Talaromyces thermophilus*," *Biochim. Biophys. Acta*, 1353(3): 217-223, 1997.

Pasamontes, L. et al., "Gene cloning, purification, and characterization of a heat-stable phytase from the fungus *Aspergillus fumigatus*," *Appl. Environ. Microbiol.*, 63(5): 1696-1700, 1997.

Pauwels, R., "Biological Activity of New 2-5A Analogues," *Chemica Scripta*, 26: 141-145, 1986.

Pearson, W.R. et al., "Improved Tools for Biological Sequence Comparison," *Proc. Natl. Acad. Sci. USA*, 85(8):2444-2448, 1988.

Piddington, C.S. et al., "The cloning and sequencing of the genes encoding phytase (phy) and pH 2.5-optimum acid phosphatase (aph) from *Aspergillus niger* var. *awamori*," *Gene*, 133(1): 55-62, 1993.

Powar, V.K. et al., "Purification and properties of phytate-specific phosphatase from *Bacillus subtilis*," *J. Bacteriol.* 151(3):1102-1108, 1982.

Qi, Y. et al., "The pst operon of *Bacillus subtilis* has a phosphate-regulated promoter and is involved in phosphate transport but not in regulation of the pho regulon," *J. Bacteriol*,. 179(8): 2534-2539, 1997.

Rawls, R. L., "Optimistic about Antisense," *Chemical & Engineering News*, 75(22): 35-39, 1997.

Rodriguez, E. et al., "Cloning, Sequencing, and Expression of an *Escherichia coli* Acid Phosphatase/Phytase Gene (appA2) Isolated from Pig Colon," *Biochemical and Biophysical Research Communications*, 257(1):117-123, 1999.

Rodriguez, E. et al., "Site-Directed Mutagenesis Improves Catalytic Efficiency and Thermostability of *Escherichia coli* pH 2.5 Acid Phosphatase/Phytase Expressed in *Pichia pastoris*," *Archives of Biochemistry and Biophysics*, 382(1): 105-112, 2000.

Rogers, S.G. et al., "Gene Transfer in Plants: Production of Transformed Plants Using Ti Plasmid Vectors," In *Methods for Plant Molecular Biology*, edited by A. Weissbach et al., pp. 423-436. New York, Academic Press, 1988.

Roland, D.A. et al., "Influence of calcium and environmental temperature on performance of first-cycle cycle (phase 1) commercial leghorns," *Poultry Science*, 75(1):62-8, 1996.

Sanger, F. et al., "DNA Sequencing with Chain-Terminating Inhibitors," *Proceedings of the National Academy of Sciences of the United States of America*, 74(12):5463-5467, 1977.

Sawai, H., "Synthesis and properties of oligoadenylic acids containing 2'-5' phosphoramide linkage," *Chemistry Letters*, (5):805-808, 1984.

Schwartz, R.M. et al., "Matrices for detecting distant relationships," In *Atlas of Protein Sequence and Structure*, edited by M.O. Dayhoff, 5 supp. 3:pp. 345-352, Silver Spring, MD, National Biomedical Research Foundation, 1978.

Shimizu, M., "Purification and Characterization of Phytase from *Bacillus subtilis* (natto) N-77," *Bioscience, Biotechnology, Biochemistry*, 56(8):1266-1269, 1992.

Simons, P.C.M. et al., "Improvement of Phosphorus Availability by Microbial Phytase in Broilers and Pigs," *British Journal of Nutrition*, 64(02):525-540, 1990.

Skinner, R.H. et al., "Use of the Glu-Glu-Phe C-terminal epitope for rapid purification of the catalytic domain of normal and mutant ras GTPase-activating proteins," *J. Biol. Chem.*, 266(22):14163-14166, 1991.

Smith, T.F. et al., "Comparison of biosequences," *Adv. Appl. Math.*, 2:482-489, 1981.

Sojar, H.T. et al., "A chemical method for the deglycosylation of proteins," *Arch. Biochem. Biophys.*, 259(1):52-57, 1987.

Sprinzl, M. et al., "Enzymatic Incorporation of ATP and CTP Analogues into the 3' End of tRNA," *European Journal of Biochemistry*, 81(3):579-589, 1977.

Stemmer, W.P.C., "Rapid evolution of a protein in vitro by DNA shuffling," *Nature*, 370(6488):389-391, 1994.

Takamatsu, N. et al., "Expression of bacterial chloramphenicol acetyltransferase gene in tobacco plants mediated by TMV-RNA," *EMBO J.*, 6(2): 307-311, 1987.

Thotakura, N. R. et al., "Enzymatic deglycosylation of glycoproteins," *Meth. Enzymol.*, 138: 350-359, 1987.

Timberlake, W.E., "Cloning and Analysis of Fungal Genes," In *More Gene Manipulations in Fungi*, edited by J.W. Bennett et al., pp. 51-85, San Diego, CA, Academic Press, 1991.

Tjalsma, H. et al., "Signal Peptide-Dependent Protein Transport in *Bacillus subtilis*: a Genome-Based Based Survey of the Secretome," *Microbiol. Mol. Biol. Rev.*, 64(3):515-547, 2000.

Ullah, A.H.J. et al., "Extracellular Phytase (E. C. 3.1.3.8) from *Aspergillus ficuum* NRRL—3135: Purification and Characterization," *Preparative Biochemistry*, 17(1):63, 1987.

Weber, K.L. et al., "Rapid acquisition of unknown DNA sequence adjacent to a known segment by multiplex restriction site PCR," *BioTechniques*, 25(3): 415-419, 1998.

Weidner, G. et al., "Development of a homologous transformation system for the human pathogenic fungus *Aspergillus fumigatus* based on the pyrG gene encoding orotidine 5"-monophosphate decarboxylase," *Current Genetics*, 33(5):378-385, 1998.

Winter, J. et al., "The expression of heat shock protein and cognate genes during plant development," *Results and Problems in Cell Differentiation*, 17:85-105, 1991.

Wodzinski, R.J. et al., "Phytase," In *Advances in Applied Microbiology*, 42:pp. 263-302. http://www.sciencedirect.com/science/article/B7CSY-4S8VDD6-7/2/362d9c0f18191d689512ab68d6232128, New York: Academic Press, 1996.

Wyss, M. et al., "Biochemical Characterization of Fungal Phytases (myo-Inositol Hexakisphosphate Phosphohydrolases): Catalytic Properties," *Appl. Environ. Microbiol.*, 65(2):367-373, 1999.

Yamada, K. et al., "Phytase from *Aspergillus terreus*," *Agr. Biol. Chem.*, 32(10):1275-1282, 1968.

PCT International Search Report for PCT/US03/25058, filed Aug. 11, 2003.

EP Supplementary European Search Report for EP 03 78 5159, filed Aug. 11, 2003.

Sanchez, O. et al., "Efficient transformation of *Aspergillus nidulans* by electroporation of germinated conidia," *Fungal Genet. Newsletter*, 43:48-51, 1996.

\* cited by examiner

```
         1         10        20        30        40        50        60        70        80        90
EBC18B2  VRSKKLWIVASTALLISVAFSSSIASAAEEQSEPELKLESVVIVSRHGVRAPTKATQLMQDVTPDAWPTWPVKLGWLTPRGGELIAYLGH  (SEQ ID No. 2)
PHY679   ----------------------------------------A-----------------------------------------------  (SEQ ID No. 3)
PHY735   ----------------------------------------------------------------------------------------  (SEQ ID No. 4)
PHY736   ----------------------------------------------------------------------------------------  (SEQ ID No. 5)
PHY846   --------L-------------------------------------------------------------------------------  (SEQ ID No. 6)
PHY850   ----------------------------------------------------------------R---------------------  (SEQ ID No. 7)
PHY902   ----------------------------------------------------------------------------------------  (SEQ ID No. 8)

100       110       120       130       140       150       160       170       180
EBC18B2  YQRQRLVADGLLAKKGCPQSGQVAIIADVDERTRKTGEAFAAGLAPDCAITVHTQADTSSPDLFNPLKTGVCQLDNANVTDAILSRAGG  (SEQ ID No. 2)
PHY679   -----------------------------------------------R----------------------------------------  (SEQ ID No. 3)
PHY735   -----------------------------------------------R----------K-----------------------------  (SEQ ID No. 4)
PHY736   ------------V----------------------------------R----------------------------------------  (SEQ ID No. 5)
PHY846   -----------------------------------------------R----------------------------------------  (SEQ ID No. 6)
PHY850   -----------------------------------------------R----------------------------------------  (SEQ ID No. 7)
PHY902   ----------------------------------------------------------------------------------------  (SEQ ID No. 8)

190       200       210       220       230       240       250       260       270
EBC18B2  SIADFTGHRQTAFRELERVLNFPQSNLCLKREKQDESCSLTQALPSELKVSADNVSLTGAVSLASMLTEIFLLQQAQGMPEPGWGRITDS  (SEQ ID No. 2)
PHY679   ----------------------------------------------------------------------------------------  (SEQ ID No. 3)
PHY735   ----------------------------------------------------------------------------P-----------  (SEQ ID No. 4)
PHY736   ----------------------------------------------------------------------------------------  (SEQ ID No. 5)
PHY846   ----------------------------------------------------------------------------------------  (SEQ ID No. 6)
PHY850   ----------------------------R-----------------------------------------------------------  (SEQ ID No. 7)
PHY902   ----------------------------------------------------------------------------------------  (SEQ ID No. 8)
```

FIG. 12A

```
           280       290       300       310       320       330       340       350       360
EBC18B2    HQWNTLLSLHNAQFYLLQRTPEVARSRATPLLDLIKTALTPHPPQKQAYGVTLPTSVLFIAGHDTNLANLGGALELNWTLPGQPDNTPPG (SEQ ID No. 2)
PHY679     ------------------------------------------------------------------------------------------ (SEQ ID No. 3)
PHY735     ------------------------------------------------------------------------------------------ (SEQ ID No. 4)
PHY736     ------------------------------------------------------------------------------------------ (SEQ ID No. 5)
PHY846     ------------------------------------------------------------------------------------------ (SEQ ID No. 6)
PHY850     ------------------------------------------------------------------------------------------ (SEQ ID No. 7)
PHY902     ------------------------------------------------------------------------------------------ (SEQ ID No. 8)

370       380       390       400       410       420       430       440
EBC18B2    GELVFERWRRLSDNSQWIQVSLVFQTLQQMRDKTPLSLNTPPGEVKLTLAGCEERNAQGMCSLAGFTQIVNEARIPACSL (SEQ ID No. 2)
PHY679     -------------------------------------------------------------------------------- (SEQ ID No. 3)
PHY735     -------------------------------------------------------------------------------- (SEQ ID No. 4)
PHY736     -------------------------------------------------------------------------------- (SEQ ID No. 5)
PHY846     -------------------------------------------------------------------------------- (SEQ ID No. 6)
PHY850     -------------------------------------------------------------------------------- (SEQ ID No. 7)
PHY902     -------------------------------------------------------------------------------- (SEQ ID No. 8)
```

FIG. 12B

```
         1         10        20        30        40        50        60        70        80        90
EBC18B2  VRSKKLNIVASTALLISVAFSSSIASAAEEQSEPELKLESVVIVSRHGVRAPTKATQLMQDVTPDAWPTWPVKLGWLTPRGGELIAYLGH  (SEQ ID No. 2)
PHY850   ---------L----------------------------------------------------------------------------  (SEQ ID No. 9)
PHY1361  ---------L----------------------------------------------E-----------------------------  (SEQ ID No. 10)
PHY1363  ---------L------------------------------------------------------------V---------------  (SEQ ID No. 11)

100       110       120       130       140       150       160       170       180
EBC18B2  YQRQRLIVADGLLAKKGCPQSGQVAIIADVDERTRKTGEAFAAGLAPDCAITVHTQADTSSPDLFNPLKTGVCQLDNANVTDAILSRAGG  (SEQ ID No. 2)
PHY850   -------------------------------------------------R------------------------------------  (SEQ ID No. 9)
PHY1361  -------------------------------------------------R------------------------------------  (SEQ ID No. 10)
PHY1363  -------------------------------------------------R------------------------------------  (SEQ ID No. 11)

190       200       210       220       230       240       250       260       270
EBC18B2  SIADFTGHRQTAFRELERVLNFPQSNLCLKREKQDESCSLTQALPSELKVSADNVSLTGAVSLASMLTEIPLLQQAQGMPEPGWGRITDS  (SEQ ID No. 2)
PHY850   --------------------------------------------------------------------------------------  (SEQ ID No. 9)
PHY1361  --------------------------------------------------------------------------------------  (SEQ ID No. 10)
PHY1363  --------------------------------------------------------------------------------------  (SEQ ID No. 11)

280       290       300       310       320       330       340       350       360
EBC18B2  HQWNTLLSLHNAQFYLLQRTPEVARSRATPLLDLIKTALTPHPPQKQAYGVTLPTSVLFIAGHDTNLANLGGALELNWTLPGQPDNTPPG  (SEQ ID No. 2)
PHY850   --------------------------------------------------------------------------------------  (SEQ ID No. 9)
PHY1361  --------------------------------------------------------------------------------------  (SEQ ID No. 10)
PHY1363  --------------------------------------------------------------------------------------  (SEQ ID No. 11)

370       380       390       400       410       420       430       440
EBC18B2  GELVFERWRRLSDNSQWIQVSLVFQTLQQMRDKTPLSLNTPPGEVKLTLAGCEERNAQGMCSLAGFTQIVNEARIPACSL  (SEQ ID No. 2)
PHY850   -------------------------------------------------------------------------------  (SEQ ID No. 9)
PHY1361  ---------------------------------------------------------D-------------------S  (SEQ ID No. 10)
PHY1363  ---------------------------------------------------------V--------------------  (SEQ ID No. 11)
```

FIG. 14

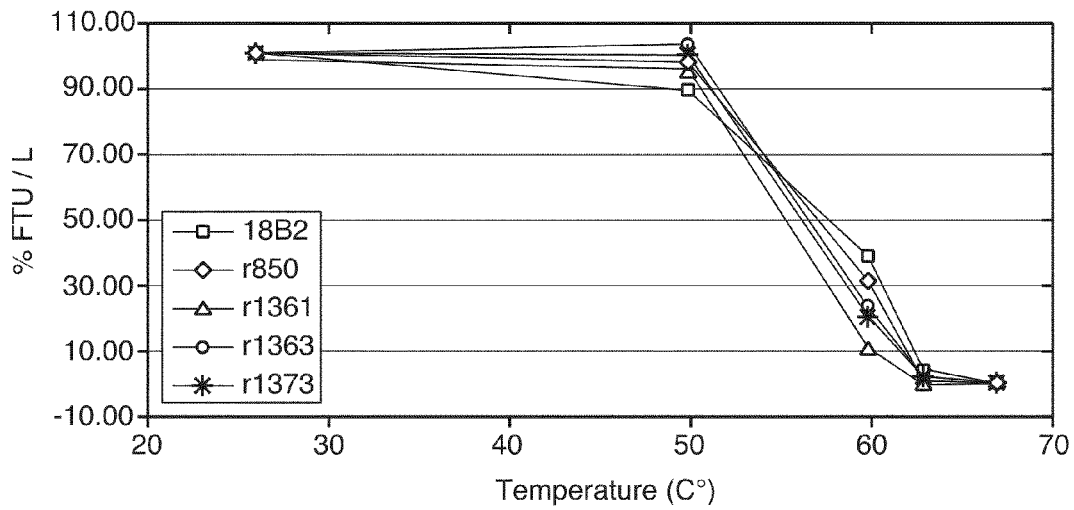

FIG. 18

Oligonucleotide primers and combinations thereof used to amplify AppA related sequences.

AppA3F 5'-atgaaagcgatcttaat (SEQ ID No. 12)
AppA5F 5'-cgtcatggtgtgcgtgctcc (SEQ ID No. 13)
AppA6F 5'-cgccagaggttgcccg (SEQ ID No. 14)
App/7R 5'-gcggctggcaacctctgg (SEQ ID No. 15)
AppA4R 5'-ttacaaactgcacgccggtatgcgtgcgtgcttcatt (SEQ ID No. 16)

Primer combinations:

AppA 3F+4R = 1.3kb product
AppA 3F+7R = 0.86kb product
AppA 5F+4R = 1.19kb product
AppA 6F+4R = 0.44kb product
AppA SF+7R 0.75kb product

FIG. 19

| Source | | 10 | 20 | 30 | 40 | 50 | 60 | 70 | 80 | |
|---|---|---|---|---|---|---|---|---|---|---|
| E. coli | | MKAILIPFLS | LLIPLTPQSA | FAQSEPELKL | ESVVIVSRHG | VRAPTKATQL | MQDVTPDAWP | TWPVKLGWLT | PRGELIAYL | (SEQ ID No. 17) |
| Shigella flexnarii | | .......... | ....S..... | .......... | .......... | .......... | .......... | .......... | .....F... | (SEQ ID No. 18) |
| Shigella sonnei | | .......... | .......... | .......... | .......... | .......... | .......... | .......... | ......... | (SEQ ID No. 19) |
| Pasteurella aerogenes | | .......... | .......... | .......... | .......... | .......... | .......... | .......... | ......... | (SEQ ID No. 20) |
| Enterobacter cloacae | | .......... | .......... | .......... | .......... | .......... | .......... | .......... | .....F... | (SEQ ID No. 21) |
| Enterobacter agglomerans | | .......... | .......... | .......... | .......... | .......... | .......... | .......... | ......... | (SEQ ID No. 22) |
| Proteus vulgaris | | .......... | .......... | .......... | .......... | .......... | .......... | .......... | ......... | (SEQ ID No. 23) |
| Zoo Compost Enrichment | | .......... | .......... | .......... | .......... | .......... | .......... | .......... | ......... | (SEQ ID No. 32) |

| Source | | 90 | 100 | 110 | 120 | 130 | 140 | 150 | 160 | |
|---|---|---|---|---|---|---|---|---|---|---|
| E. coli | | GHYQRQRLVA | DGLLAKKGCP | QSGQVAIIAD | VDERTRKTGE | AFAAGLAPDC | AITVHTQADT | SSPDPLFNPL | KTGVCQLDNA | (SEQ ID No. 17) |
| Shigella flexnarii | | .......... | .......... | .......P.. | .......... | .......... | .......... | .......... | .......... | (SEQ ID No. 18) |
| Shigella sonnei | | .......... | .......... | .......... | .......... | .......... | .......... | .......... | .......... | (SEQ ID No. 19) |
| Pasteurella aerogenes | | .......... | .......... | .......... | .......... | .......... | .......... | .......... | .......... | (SEQ ID No. 20) |
| Enterobacter cloacae | | .......... | .......... | .......P.. | .......... | .......... | .......... | .......... | .......... | (SEQ ID No. 21) |
| Enterobacter agglomerans | | .......... | .......... | .......P.. | .......... | .......... | .......... | .......... | .......... | (SEQ ID No. 22) |
| Proteus vulgaris | | .......... | .......... | .......... | .......... | .......... | .......... | .......... | .......... | (SEQ ID No. 23) |
| Zoo Compost Enrichment | | .......... | .......... | .......... | .......... | .......... | .......... | .......... | .......... | (SEQ ID No. 32) |

| Source | | 170 | 180 | 190 | 200 | 210 | 220 | 230 | 240 | |
|---|---|---|---|---|---|---|---|---|---|---|
| E. coli | | NVTDAILSRA | GGSIADFTGH | RQTAFRELER | VLNFPQSNLC | LKREKQDESC | SLTQALPSEL | KVSADNVSLT | GAVSLASMLT | (SEQ ID No. 17) |
| Shigella flexnarii | | .......... | .......... | .......... | .......... | .......... | .......... | .......... | .......... | (SEQ ID No. 18) |
| Shigella sonnei | | .......... | .......... | .......... | .......... | .......... | .......... | .......... | .......... | (SEQ ID No. 19) |
| Pasteurella aerogenes | | .......... | .......... | .......... | .......... | .......... | .......... | ....A..... | .......... | (SEQ ID No. 20) |
| Enterobacter cloacae | | .......... | .......... | .......... | .......... | .......... | .......... | .......... | .......... | (SEQ ID No. 21) |
| Enterobacter agglomerans | | .......... | .......... | .......... | .......... | ....F..... | .......... | .......... | .......... | (SEQ ID No. 22) |
| Proteus vulgaris | | .......... | .......... | .......... | .......... | .......... | .......... | .......... | .......... | (SEQ ID No. 23) |
| Zoo Compost Enrichment | | .......... | .......... | .......... | .......... | .......... | .......... | .........C | .......... | (SEQ ID No. 32) |

FIG. 20A

| Source | 250 EIFLLQQAQG | 260 MPEPGWGRIT | 270 DSHQWNTLLS | 280 LHNAQFYLLQ | 290 RTPEVARSRA | 300 TPLLDLIKTA | 310 LTPHPEQKQA | 320 YGVTLPTSVL | |
|---|---|---|---|---|---|---|---|---|---|
| E. coli | EIFLLQQAQG | MPEPGWGRIT | DSHQWNTLLS | LHNAQFYLLQ | RTPEVARSRA | TPLLDLIKTA | LTPHPEQKQA | YGVTLPTSVL | (SEQ ID No. 17) |
| Shigella flexnarii | .......... | .......... | .......... | .......... | .......... | .......... | .......... | .......... | (SEQ ID No. 18) |
| Shigella sonnei | .......... | .......... | .......... | .......... | .......... | ......MA.. | .......... | .......... | (SEQ ID No. 19) |
| Pasteurella aerogenes | .......... | .......... | .......... | .......... | .......... | .......,.. | .......... | .......... | (SEQ ID No. 20) |
| Enterobacter cloacae | .......... | .......... | .......N.. | .......... | .......... | .......... | .......... | .......... | (SEQ ID No. 21) |
| Enterobacter agglomerans | .......... | .......... | .......... | .......... | .......... | .......... | .......... | .......... | (SEQ ID No. 22) |
| Proteus vulgaris | .......... | .......... | .......... | .........I | .......... | .......... | .......... | .......... | (SEQ ID No. 23) |
| Zoo Compost Enrichment | .......... | .......... | .......S.. | .......... | .......... | .......... | .......... | .......... | (SEQ ID No. 32) |

| Source | 330 FIAGHDTNLA | 340 NLGGALELNW | 350 TLPGQPDNTP | 360 PGGELVFERW | 370 RRLSDNSQWI | 380 QVSLVFQTLQ | 390 QMRDKTPLSL | 400 NTPPGEVKLT | |
|---|---|---|---|---|---|---|---|---|---|
| E. coli | FIAGHDTNLA | NLGGALELNW | TLPGQPDNTP | PGGELVFERW | RRLSDNSQWI | QVSLVFQTLQ | QMRDKTPLSL | NTPPGEVKLT | (SEQ ID No. 17) |
| Shigella flexnarii | .......... | .F........ | .......... | .......... | .......... | .......... | .......... | .......... | (SEQ ID No. 18) |
| Shigella sonnei | .......... | .......... | .......... | .......... | .......... | .......... | .......... | .......... | (SEQ ID No. 19) |

| Source | 410 LAGCEERNAQ | 420 GMCSLAGFTQ | 430 IVNEARIPAC | 440 SL* | |
|---|---|---|---|---|---|
| E. coli | LAGCEERNAQ | GMCSLAGFTQ | IVNEARIPAC | SL* | (SEQ ID No. 17) |
| Shigella flexnarii | .......... | .......... | .......... | .. | (SEQ ID No. 18) |
| Shigella sonnei | .......... | .......... | .......... | .. | (SEQ ID No. 19) |

*FIG. 20B*

```
                 1              *             20             *             40             *             60             *             80
E. coli    ATGAAAGGCGATCTTAATCCCATTTTTATCTCTTCTGATTCCGTTAACCCCGCAATCTGCATTCGCTCAGAGTGAGCCGGA  (SEQ ID No. 24)
S. flex.   ----------------------------------------T-----------------------------------------  (SEQ ID No. 25)
S. sonn.   ----------------------------------------------------------------------------------  (SEQ ID No. 26)
P. aero.   ----------------------------------------------------------------------------------  (SEQ ID No. 27)
E. cloa.   ----------------------------------------------------------------------------------  (SEQ ID No. 28)
E. aggl.   ----------------------------------------------------------------------------------  (SEQ ID No. 29)
P. vulg.   ----------------------------------------------------------------------------------  (SEQ ID No. 30)
compost    ----------------------------------------------------------------------------------  (SEQ ID No. 33)

*            100             *            120             *            140             *            160
E. coli    GCTGAAGCTGGAAAGTGTGGTGATTGTCAGTCGTCATGGTGTGCGTGCTCCAACCAAGGCCACGCAACTGATGCAGGATG  (SEQ ID No. 24)
S. flex.   ----------------------------------------------------------------------------------  (SEQ ID No. 25)
S. sonn.   ----------------------------------------------------------------------------------  (SEQ ID No. 26)
P. aero.   ----------------------------------------------------------------------------------  (SEQ ID No. 27)
E. cloa.   ----------------------------------------------------------------------------------  (SEQ ID No. 28)
E. aggl.   ----------------------------------------------------------------------------------  (SEQ ID No. 29)
P. vulg.   ----------------------------------------------------------------------------------  (SEQ ID No. 30)
compost    ----------------------------------------------------------------------------------  (SEQ ID No. 33)

*            180             *            200             *            220             *            240
E. coli    TCACCCCAGACGCATGGCCAACCTGGCCGGTAAAACTGGGTTGGCTGACACCGGCGGTGGTGAGCTAATCGCCTATCTC  (SEQ ID No. 24)
S. flex.   -----------------------------------------------------------------------------T--  (SEQ ID No. 25)
S. sonn.   ----------------------------------------------------------------------------------  (SEQ ID No. 26)
P. aero.   ----------------------------------------------------------------------------------  (SEQ ID No. 27)
E. cloa.   -----------------------------------------------------------------------------T--  (SEQ ID No. 28)
E. aggl.   ----------------------------------------------------------------------------------  (SEQ ID No. 29)
P. vulg.   ----------------------------------------------------------------------------------  (SEQ ID No. 30)
compost    ----------------------------------------------------------------------------------  (SEQ ID No. 33)
```

```
              *               740                *               760                *               780                *               800
E. coli   GAGATATTTCTCCTGCAACAAGCACACAGGAATGCCGGAGCCCGGGGTGGGGAAGGATCACCGATTCACACCAGTGGAACAC    (SEQ ID No. 24)
S. flex.  ----------------------------------------------A------------------------------------    (SEQ ID No. 25)
S. sonn.  ------------------------------------------------------------------------------------    (SEQ ID No. 26)
P. aero.  ------------------------------------------------------------------------------------    (SEQ ID No. 27)
E. cloa.  --------------------------------------------------------------A---------------------    (SEQ ID No. 28)
E. aggl.  ------------------------------------------------------------------------A-----------    (SEQ ID No. 29)
P. vulg.  ------------------------------------------------------------------------A-----------    (SEQ ID No. 30)
compost   ----------------------------------------------------------------------------G-------    (SEQ ID No. 33)

*               820                *               840                *               860                *               880
E. coli   CTTGCTAAGTTTGCATAACGCGCAATTTTATTTGCTACAACGCCAGAGTTGCCCGCCAGCCGCCACCCCGTTAT           (SEQ ID No. 24)
S. flex.  -G--------T-G------------------------------------------------------------           (SEQ ID No. 25)
S. sonn.  -------------------------------------------------------------------------           (SEQ ID No. 26)
P. aero.  -------------------------------------------------------------------------           (SEQ ID No. 27)
E. cloa.  -------------------------------------------------------------------------           (SEQ ID No. 28)
E. aggl.  -------------------------------------------------------------------------           (SEQ ID No. 29)
P. vulg.  --------------------------------------------A----------------------------           (SEQ ID No. 30)
compost   -------------------------------------------------------------------------           (SEQ ID No. 33)

*               900                *               920                *               940                *               960
E. coli   TAGATTTGATCAAGACAGCGTTGACGCCCATCCACCGCAAAAACAGGCGTATGGTGTGACATTACCCACTTCAGTGCTG    (SEQ ID No. 24)
S. flex.  -G------------------------------------------------------------------------A----    (SEQ ID No. 25)
S. sonn.  -------------------------------------------------------------------------------    (SEQ ID No. 26)
P. aero.                                                                                      (SEQ ID No. 27)
E. cloa.                                                                                      (SEQ ID No. 28)
E. aggl.                                                                                      (SEQ ID No. 29)
P. vulg.                                                                                      (SEQ ID No. 30)
compost                                                                                       (SEQ ID No. 33)
```

FIG. 21D

```
                        *         980         *        1000         *        1020         *        1040
E. coli    TTTATCGCCGGACACGATACTAATCTGGCAAATCTCGGCGGCGCACTGAGACTCAACTGAGACGCTTCCGGTCAGCCGGA  (SEQ ID No. 24)
S. flex.   -----T------------------------------------------T-----------------------------  (SEQ ID No. 25)
S. sonn.   ----------------------------------------------------------------------------   (SEQ ID No. 26)
P. aero.   ----------------------------------------------------------------------------   (SEQ ID No. 27)
E. cloa.   ----------------------------------------------------------------------------   (SEQ ID No. 28)
E. aggl.   ----------------------------------------------------------------------------   (SEQ ID No. 29)
P. vulg.   ----------------------------------------------------------------------------   (SEQ ID No. 30)
compost    ----------------------------------------------------------------------------   (SEQ ID No. 33)

*        1060         *        1080         *        1100         *        1120
E. coli    TAACACGCCGCCAGTGTGGTGTTTGAACTGGTGTGTTTGAACGCTGGCGTCGGCTAAGCGATAACAGCCAGTGATTCAGTTTCGC  (SEQ ID No. 24)
S. flex.   ----------------------------------------------------------------------------   (SEQ ID No. 25)
S. sonn.   ----------------------------------------------------------------------------   (SEQ ID No. 26)
P. aero.   ----------------------------------------------------------------------------   (SEQ ID No. 27)
E. cloa.   ----------------------------------------------------------------------------   (SEQ ID No. 28)
E. aggl.   ----------------------------------------------------------------------------   (SEQ ID No. 29)
P. vulg.   ----------------------------------------------------------------------------   (SEQ ID No. 30)
compost    ----------------------------------------------------------------------------   (SEQ ID No. 33)

*        1140         *        1160         *        1180         *        1200
E. coli    TGGTCTTCCAGACTTTACAGCAGATGCGTGATAAAACGCCCGCTGTCATTAAATACGCGCCCCGGAGAGGTGAAACTGACC  (SEQ ID No. 24)
S. flex.   ----------------------------------------------------------------------------   (SEQ ID No. 25)
S. sonn.   ----------------------------------------------------------------------------   (SEQ ID No. 26)
P. aero.   ----------------------------------------------------------------------------   (SEQ ID No. 27)
E. cloa.   ----------------------------------------------------------------------------   (SEQ ID No. 28)
E. aggl.   ----------------------------------------------------------------------------   (SEQ ID No. 29)
P. vulg.   ----------------------------------------------------------------------------   (SEQ ID No. 30)
compost    ----------------------------------------------------------------------------   (SEQ ID No. 33)
```

FIG. 21E

```
              *         1220          *         1240          *         1260          *         1280
E. coli  CTGGCAGGATGTGAAGAGCGAAATGCGCAGGCATGTGTTCGTTGGCAGTTTTACGCAAATCGTGAATGAAGCACGCAT  (SEQ ID No. 24)
S. flex. ------------------------------------------------------------------------------  (SEQ ID No. 25)
S. sonn. ------------------------------------------------------------------------------  (SEQ ID No. 26)
P. aero. ------------------------------------------------------------------------------  (SEQ ID No. 27)
E. cloa. ------------------------------------------------------------------------------  (SEQ ID No. 28)
E. aggl. ------------------------------------------------------------------------------  (SEQ ID No. 29)
P. vulg. ------------------------------------------------------------------------------  (SEQ ID No. 30)
compost                                                                                  (SEQ ID No. 33)

*         1309
E. coli  ACCGGGCGTGCAGTTTGTAA  (SEQ ID No. 24)
S. flex. ------------^^^       (SEQ ID No. 25)
S. sonn. ------------^^^       (SEQ ID No. 26)
P. aero. ------------          (SEQ ID No. 27)
E. cloa. ------------          (SEQ ID No. 28)
E. aggl. ------------          (SEQ ID No. 29)
P. vulg. ------------          (SEQ ID No. 30)
compost                        (SEQ ID No. 33)
```

FIG. 21F

MUTANT *E. COLI APPA* PHYTASE ENZYMES AND NATURAL VARIANTS THEREOF, NUCLEIC ACIDS ENCODING SUCH PHYTASE ENZYMES, VECTORS AND HOST CELLS INCORPORATING SAME AND METHODS OF MAKING AND USING SAME

CROSS-REFERENCE

This application is a national stage application of PCT patent application number PCT/US2003/025058 filed Aug. 11, 2003, and claims priority from US Provisional patent application No. 60/403,330 filed Aug. 12, 2002, each of which are incorporated herein in their entirety.

FIELD OF THE INVENTION

The present invention relates to natural variantss of the *E. coli* AppA phytase isolated from various microbial sources, mutant appA phytase from *E. coli*, nucleic acid sequences encoding phytase, as well as the production of mutant *E. coli* appA phytase and its use.

REFERENCES al-Batshan et al., Poultry Science 73(10):1590-1596 (1994).

Altschul, S. F., Gish, W., Miller, W., Myers, E. W. & Lipman, D. J. (1990) "Basic local alignment search tool." J. Mol. Biol. 215:403-410.

Altschul, S. F., Madden, T. L., Schäffer, A. A., Zhang, J., Thang, Z., Miller, W. & Lipman, D. J. (1997) "Gapped BLAST and PSI-BLAST: a new generation of protein database search programs." Nucleic Acids Res. 25:3389-3402.

Aplin and Wriston, Crit. Rev. Biochem., pp. 259-306 (1981).

ASC Symposium Series 580, "Carbohydrate Modifications in Antisense Research", Chapters 2, 3, 6 and 7, Ed. Y. S. Sanghui and P. Dan Cook.

Ausubel et al. (eds.) (1995) Current Protocols In Molecular Biology, 3rd edition, John Wiley & Sons, Inc.

Baker et al., U.S. Pat. No.5,571,706 (1996).

Beaucage et al. (1993) Tetrahedron 49(10):1925.

Benner, Steven A., U.S. Pat. No. 5,216,141 (1993).

Bennett & Lasure, More Gene Manipulations in Fungi, Academic Press, San Diego, pp. 70-76 (1991).

Benton, W. and Davis, R., 1977, Science 196:180.

Berger and Kimmel, (1987), Guide to Molecular Cloning Techniques, Methods in Enzymology, Vol. 152, Academic Press, San Diego Calif.

Birnboim, H. C. and Doly, J. (1979). Nucleic Acids Research 7: 1513-23.

Botstein, D. and Shortle, D. (1985) Science 229:1193-1201.

Bowen et al., U.S. Pat. No. 5,736,369 (1998).

Bremel et al., U.S. Pat. No. 6,291,740 (2001).

Bremel et al., U.S. Pat. No. 6,080,912 (2000).

Brisson et al (1984) Nature 310:511-514.

Briu et al. (1989) J. Am. Chem. Soc. 111:2321.

Broglie et al (1984) Science 224:838-843).

Cadwell, R. C. and Joyce, G. F., 1992, PCR Methods Applic. 2: 28-33.

Canadian Journal of Animal Science 75(3):439-444 (1995).

Committee on Food Chemicals Codex, Institute of Medicine, *Food Chemicals Codex*, 4th Edition, National Academy Press, Washington, D.C., 1996.

Carlsson et al., Nature 380:207 (1996).

Clark, H. Fred, U.S. Pat. No. 5,610,049 (1997).

Common et al., Nature 143:370-380 (1989)

Conklin et al., U.S. Pat. No. 5,750,386 (1998).

Cook et al., U.S. Pat. No. 5,637,684 (1997).

Coruzzi et al (1984) EMBO J 3:1671-1680.

Creighton, T. E., Proteins: Structure and Molecular Properties, W. H. Freeman & Co., San Francisco, pp. 79-86 (1983).

Cromwell et al., "P—a key essential nutrient, yet a possible major pollutant—its central role in animal nutrition", In *Biotechnology in the Feed Industry* (T. P. Lyons, ed.) Alltech Technical Publications, Nicholasville, Ky. (1991) p. 133.

Cromwell, G. L. T., T. S. Stahly, R. D. Coffey, H. J. Monegue, and J. H. Randolph. 1993. Efficacy of phytase in improving bioavailability of phosphorus in soybean and corn-soybean meal diets for pigs. J. Anim. Sci. 71:1831.

Damron et al., Poultry Science 74(5):784-787 (1995).

Dassa et al., J. Bacteriol. 172:5497-5500 (1990).

Dayhoff, M. O., Schwartz, R. M. & Orcutt, B. C. (1978) "A model of evolutionary change in proteins." In "Atlas of Protein Sequence and Structure, vol. 5, suppl. 3." M. O. Dayhoff (ed.), pp. 345-352, Natl. Biomed. Res. Found., Washington, D.C. Deutscher, Methods in Enzymology, 182 (1990).

DeBoer et al, U.S. Pat. No. 6,066,725 (2000).

De Clercq et al., U.S. Pat. No. 5,589,615 (1996).

De Mesmaeker et al., U.S. Pat. No. 5,602,240 (1997).

De Mesmaeker et al., Bioorganic & Medicinal Chem. Lett. 4:395 (1994).

Denpcy et al., Proc. Natl. Acad. Sci. USA 92:6097 (1995).

Devlin, Robert H., U.S. Pat. No. 5,998,697 (1999).

Dieffenbach C. W. and Dveksler G. S., 1995, PCR Primer, a Laboratory Manual, Cold Spring Harbor Press, Plainview N.Y.

Eckert, K. A. and Kunkel, T. A., 1991, PCR Methods Applic. 1: 17-24.

Eckstein, Oligonucleotides and Analogues: A Practical Approach, Oxford University Press.

Edge et al., Anal. Biochem., 118:131 (1981).

Egholm (1992) J. Am. Chem. Soc. 114:1895.

Ehrlich, K. C., Montalbano, B. G., Mullaney, E. J., Dischinger Jnr., H. C. & Ullah, A. H. J. (1993). Identification and cloning of a second phytase gene (phy B) from *Aspergillus niger* (ficum). Biochemical and Biophysical Research Communications 195, 53-57.

Elander, R. P., Microbial screening, Selection and Strain Improvement, in Basic Biotechnology, J. Bullock and B. Kristiansen Eds., Academic Press, New York, 1987, 217.

Evan et al., Molecular and Cellular Biology, 5:3610-3616 (1985).

Field et al., Mol. Cell. Biol., 8:2159-2165 (1988).

Finkelstein, DB 1992 Transformation. In Biotechnology of Filamentous Fungi. Technology and Products (eds by Finkelstein & Bill) 113-156.

Fiske, C. H. and SubbaRow, Y. (1925). Journal of Biological Chemistry 66:375-392.

Fromant et al., Anal. Biochem. 224(l):347-353 (1995).

Fungaro et al. (1995) Transformation of *Aspergillus nidulans* by microprojection bombardment on intact conidia, FEMS Microbiology Letters 125 293-298.

Gelvin et al., J. Bacteriol. 172(3):1600-1608 (1990).

Gish, W. & States, D. J. (1993) "Identification of protein coding regions by database similarity search." Nature Genet. 3:266-272.

Glover, DM and Hames, BD (Eds.), DNA Cloning: A Practical Approach, Vols 1 and 2, Second Edition.

Glover, DM and Hames, BD (Eds.), 1995, DNA Cloning 1: A Practical Approach, Oxford University Press, Oxford).

Glover, DM and Hames, BD (Eds.), 1995, DNA Cloning 2: A Practical Approach, Oxford University Press, Oxford).

Golovan et al., Can. J. Microbiol. 46:59-71 (2000).

Greiner et al., Arch. Bbiochm, biophys. 303:107-113 (1993).

Groot et al. (1998) *Agrobacterium tuinefaciens*—mediated transformation of filamentous fungi, Nature Biotechnology 16 839-842.

Grunstein, M. and Hogness, D., 1975, Proc. Natl. Acad. Sci. USA 72:3961.

Hakimuddin, et al., Arch. Biochem. Biophys., 259:52 (1987).

Hale & Marham, THE HARPER COLLINS DICTIONARY OF BIOLOGY, Harper Perennial, NY (1991).

Harayama, Trends Biotechnol. 16(2):76-82 (1998).

Henikoff & Henikoff, Proc. Natl. Acad. Sci. USA 89:10915 (1989).

Henke et al., Biol. Chem. 380(7-8):1029-1033 (1999).

Hershey et al., U.S. Pat. No. 5,268,526 (1993).

Higgins D. G., Bleasby A. J., Fuchs R. (1992) CLUSTAL V: improved software for multiple sequence alignment. Comput. Appl. Biosci. 8:189-191.

Hobbs S or Murry LE (1992) in McGraw Hill Yearbook of Science and Technology McGraw Hill, New York, N.Y., pp 191-196.

Hodges et al., U.S. Pat. No. 5,677,175 (1997).

Hopp et al., BioTechnology, 6:1204-1210 (1988).

Houdebine et al., U.S. Pat. No. 6,268,545 (2001).

Inoue et al., Gene 96:23-28 (1990).

Jaynes et al., U.S. Pat. No. 5,597,945 (1997).

Jeffs et al., J. Biomolecular NMR 34:17 (1994).

Jenkins et al., Chem. Soc. Rev. (1995) pp169-176.

Jeroch et al., Bodenkultur Vo. 45(4):361-368 (1994).

Karatzas et al., U.S. Pat. No. 5,907,080 (1999).

Karlin & Altschul, Proc. Nat'l. Acad. Sci. USA 90:5873-5787 (1993).

Kerovuo, J., Lauraeus, M., Nurminen, P., Kalkkinen, N., Apajalahti, J. (1988) Isolation, characterization and molecular gene cloning, and sequencing of a novel phytase from *Bacillus subtilis*. Appl. Environ. Micro., 64, 6, 2079-2085.

Kerovuo et al., Biochem. J. 352(pt. 3):623-628 (2000).

Kiedrowshi et al., Angew. Chem. Intl. Ed. English 30:423 (1991).

Kornegay, E. T., D. M. Denbow, Z. Yi., and V. Ravindran. 1996. Response of broilers to graded levels of Natuphosâ phytase added to corn-soybean meal-based diets containing three levels of nonphytate phosphorus. Br. J. Nutr.

Kostrewa et al., Nat. Struct. Biol. 4(3):185-190 (1997).

Kretz, K., U.S. Pat. No. 5,876,997 (1999).

Kretz, K., U.S. Pat. No. 6,110,719 (2000).

Kretz, K., U.S. Pat. No. 6,190,897 (2001).

Lebrun et al., U.S. Pat. No. 5,510,471 (1996).

Lehmann et al., Protein Engineering 13:49-57 (2000).

Letsinger, J. Org. Chem. 35:3800 (1970).

Letsinger et al., Nucleoside & Nucleotide 13:1597 (1994).

Letsinger et al. (1988) J. Am. Chem. Soc. 110:4470.

Letsinger et al. (1986) Nucl. Acids Res. 14:3487.

Leung, D. W., Chen, E., and Goeddel, D. V., 1989, Technique 1: 11-15.

Lim et al., Nature Struct. Biol. 7:108-113 (2000).

Ling et al., Anal. Biochem. 254(2):157-178 (1997).

Lubon et al., U.S. Pat. No. 6,262,336 (2001).

Lundquist et al., U.S. Pat. No. 5,780,708 (1998).

Lundquist et al., U.S. Pat. No. 5,538,880 (1996);

Lutz-Freyermuth et al., Proc. Natl. Acad. Sci. USA, 87:6393-6397 (1990).

Madden, T. L., Tatusov, R. L. & Zhang, J. (1996) "Applications of network BLAST server" Meth. Enzymol. 266:131-141.

Mag et al. (1991) Nucleic Acids Res. 19:1437.

Martin et al., Science, 255:192-194 (1992).

Meier et al. (1992) Chem. Int. Ed. Engl. 31:1008.

Melnikov et al., Nucleic Acids Res. 27(4):1056-1062 (1999).

The Merck Veterinary Manual (Seventh Edition, Merck & Co., Inc., Rahway, N.J., USA, 1991, page 1268).

Myers, R. M., Lerman, L. S., and Maniatis, T., 1985, Science 229: 242-247.

Mitchell, D. B., Vogel, K., Weimann, B. J., Pasamontes, L. and van Loon, A. P., Microbiology 143 (Pt 1), 245-252 (1997)).

Moloney et al., U.S. Pat. No. 5,750,871(1998).

Mullis, Kary B., U.S. Pat. No. 4,683,202 (1990).

Needleman & Wunsch, J. Mol. Biol. 48:443 (1970).

Nielsen (1993) Nature,365:566.

Oakley et al., *Gene* 61(3): 385-99 (1987).

Ostanin et al., J. Biol. Chem. 267:22830-22836 (1992).

Ostanin et al., J. Biol. Chem. 268:20778-28784 (1993).

Paborsky et al., Protein Engineering, 3(6):547-553 (1990).

Paxidey et al., Bioresource Technol. 77(3):203-214 (2001).

Pasamontes, L., Haiker, M., Henriquez-Huecas, M., Mitchell, D. B. and van Loon, A. P., Cloning of the phytases from *Emericella nidulans* and the thermophilic fungus *Talaromyces thermophilus*, Biochim. Biophys. Acta 1353 (3), 217-223 (1997).

Pasamontes, L., Haiker, M., Wyss, M., Tessier, M. and van Loon, A. P., Gene cloning, purification, and characterization of a heat-stable phytase from the fungus *Aspergillus fumigatus*, Appl. Environ. Microbiol. 63 (5), 1696-1700 (1997).

Pauwels et al. (1986) Chemica Scripta 26:141.

Pearson & Lipman, Proc. Nat'l. Acad. Sci. USA 85:2444 (1988).

Piedrahita et al., U.S. Pat. No. 6,271,436 (2001).

Piddington, C. S., Houston, C. S., Paloheimo, M., Cantrell, M., Miettinen-Oinonen, A., Nevalainen, H. & Rambosek, J. (1993). The cloning and sequencing of the genes encoding phytase (PhyA) and pH 2.5-optimum acid phosphatase (aph) from *Aspergillus niger* var. *awamoli*. Gene 133, 55-62.

Powar, V. K. and Jagannathan V., (1982) J. Bacteriology, 151(3), 1102-1108.

Qi et al., J. Bacteriol. 179:2534-2539 (2000).

Rawls, C & E News June 2, 1997 page 35.

Rodriguez et al, Biochem. Biophys. Res. Comm. 257:117-123 (1999).

Rodriguez et al., Arch. Biochem. Biophys. 382:105-112 (2000).

Roland et al., Poultry Science, 75(1):62-68 (1996).

Sambrook, J., Fritsch, E. F. and Maniatis, T. (1989). Molecular Cloning—A Laboratory Manual, $2^{nd}$ Ed. Cold Spring Harbour Press.

Sambrook et al. (2001). Molecular Cloning, A Laboratory Manual, 3d Ed., Cold Spring Harbor Laboratory Press, Cold Spring Harbor, N.Y.

Sanchez, O. and J. Aguirre. 1996. Efficient transformation of *Aspergillus nidulans* by electroporation of germinated conidia. Fungal Genetics Newsletter 43: 48-51.

Sanger, F., Nilken, S. and Coulson, A. R. (1977). Proc. Nat'l. Acad. Sci. USA, 74: 5463-5467.

Sanghvi et al. U.S. Pat. No. 5,386,023 (1995)

Sawai et al. (1984) Chem. Lett. 805.

Schwartz, R. M. & Dayhoff, M. O. (1978) "Matrices for detecting distant relationships." In "Atlas of Protein Sequence and Structure, vol. 5, suppl. 3." M. O. Dayhoff (ed.), pp. 353-358, Natl. Biomed. Res. Found., Washington, D.C.

Scopes, Protein Purification: Principles and Practice, Springer-Verlag, New York (1982).

Shimizu, M., (1992) Biosci. Biotech. Biochem., 56 (8), 1266-1269.

Shimizu, M., Japanese Patent Application 6-38745 (1994).

Simons et al., Br. J. Nutrition 64:525-540 (1990).

Singleton, et al., DICTIONARY OF MICROBIOLOGY AND MOLECULAR BIOLOGY, 2D ED., John Wiley and Sons, New York (1994).

Skinner et al., J. Biol. Chem., 266:15163-15166 (1991).

Smith & Waterman, Adv. Appl. Math. 2:482 (1981).

Somers et al., U.S. Pat. No. 5,773,269 (1998).

Sprinzl et al. (1977) Eur. J. Biochem. 81:579.

Stemmer, Nature 370(6488):324-325 (1994).

Summerton et al., U.S. Pat. No. 5,235,033 (1993).

Summerton et al., U.S. Pat. No. 5,034,506 (1991).

Takamatsu et al (1987) EMBO J 6:307-311.

Thotakura et al., Meth. Enzymol., 138:350 (1987).

Tjalsma et al., Microbiol. Mol. Biol. Rev. 64(3):515-547 (2000).

T'so et al., U.S. Pat. No. 4,469,863 (1984).

Ullah, H. J. and Gibson, D. M., Preparative Biochemistry, 17 (1) (1987), 63-91.

van Gorcom, Robert Franciscus Maria; van Hartingsveldt, Willem; van Paridon, Peter Andreas; Veenstra, Annemarie Eveline; Luiten, Rudolf Gijsbertus Marie; Selten, Gerardus Cornelis Maria; EP 420 358 (1991).

van Hartingsveldt, W., van Zeijl, C. M. J., Harteveld, G. M., Gouka, R. J., Suykerbuyk, M. E. G., Luiten, R. G. M., van Paridon, P. A., Selten, C. G. M., Veenstra, A. E., van Gorcom, R. F. M. & van den Hondel, C. A. J. J. (1993). Cloning, characterization and over expression of the phytase-encoding gene (PhyA) of *Aspergillus niger*. Gene 127:87-94.

Van Loon, A. and Mitchell, D.; EP 684 313 (1995).

Weber, K. L. et al., *Biotechniques* 25(3): 415-9 (1998).

Weidner, G., d'Enfert, C., Koch, A., Mol, P., and Brakhage, A. A. (1998) Development of a homologous transformation system for the human pathogenic fungus *Aspergillus fumigatus* based on the pyrG gene encoding orotidine monophosphate decarboxylase. Current Genet. 33: 378-385.

Weissbach and Weissbach (1988) Methods for Plant Molecular Biology, Academic Press, New York, N.Y., pp 421-463.

Wheeler, Mathew B., U.S. Pat. No. 5,942,435 (1999).

Winter J and Sinibaldi RM (1991) Results Probl Cell Differ 17:85-105.

Wyss et al., Appl. Env. Microbiol. 65:367-373 (1999).

Yau, Eric K., U.S. Pat. No. 5,644,048 (1997).

Yamada et al., Agr. Biol. Chem., 32 (10) (1968), 1275-1282.

BACKGROUND OF THE INVENTION

Phosphorous (P) is an essential element for growth. A substantial amount of the phosphorous found in conventional livestock feed, e.g., cereal grains, oil seed meal, and by products that originate from seeds, is in the form of phosphate which is covalently bound in a molecule know as phytate (myo-inositol hexakisphosphate). The bioavailability of phosphorus in this form is generally quite low for non-ruminants, such as poultry and swine, because they lack digestive enzymes for separating phosphorus from the phytate molecule.

Several important consequences of the inability of non-ruminants to utilize phytate may be noted. For example, expense is incurred when inorganic phosphorus (e.g., dicalcium phosphate, defluorinated phosphate) or animal products (e.g., meat and bone meal, fish meal) are added to meet the animals' nutritional requirements for phosphorus. Additionally, phytate can bind or chelate a number of minerals (e.g., calcium, zinc, iron, magnesium, copper) in the gastrointestinal tract, thereby rendering them unavailable for absorption. Furthermore, most of the phytate present in feed passes through the gastrointestinal tract, elevating the amount of phosphorous in the manure (see, e.g., Common et al., 1989). This leads to an increased ecological phosphorous burden on the environment (See, e.g., Cromwell et al., 1991).

Ruminants, such as cattle, in contrast, readily utilize phytate thanks to an enzyme produced by rumen microorganisms known as phytase. Phytase catalyzes the hydrolysis of phytate to (1) myo-inositol and/or (2) mono-, di-, tri-, tetra- and/or penta-phosphates thereof and (3) inorganic phosphate. Two different types of phytases are known: (1) a so-called 3-phytase (myo-inositol hexaphosphate 3-phosphohydrolase, EC 3.1.3.8) and (2) a so-called 6-phytase (myo-inositol hexaphosphate 6-phosphohydrolase, EC 3.1.3.26). The 3-phytase preferentially hydrolyzes first the ester bond at the 3-position, whereas the 6-phytase preferentially hydrolyzes first the ester bond at the 6-position.

Microbial phytase, as a feed additive, has been found to improve the bioavailability of phytate phosphorous in typical non-ruminant diets (See, e.g., Cromwell, et al, 1993). The result is a decreased need to add inorganic phosphorous to animal feeds, as well as lower phosphorous levels in the excreted manure (See, e.g., Komegay, et al, 1996).

Despite such advantages, few of the known phytases have gained widespread acceptance in the feed industry. The reasons for this vary from enzyme to enzyme. Typical concerns relate to high manufacture costs and/or poor stability/activity of the enzyme in the environment of the desired application. A number of enzymatic criteria must be fulfilled by a phytase if it is to be attractive for widespread use in the animal feed industry. These include a high overall specific activity, a low pH optimum, resistance to gastrointestinal proteases and thermos/ability (See, e.g., Simons et al., 1990). Thermostability is perhaps the single most important prerequisite for successful application of feed enzymes because all of the components, including phytase, are briefly exposed to temperatures between 60 and 95° C. in the feed pelleting process. Since all known microbial phytases unfold at temperatures between 56 and 78° C. (Lehmann et al., 2000), genetically engineered enzymes that can overcome this limitation would clearly have an advantage in feed applications It is, thus, generally desirable to discover and develop novel enzymes having good stability and phytase activity for use in connection with animal feed, and to apply advancements in fermentation technology to the production of such enzymes in order to make them commercially viable. It is also desirable to ascertain nucleotide sequences which can be used to produce more efficient genetically engineered organisms capable of expressing such phytases in quantities suitable for industrial production. It is still further desirable to develop a phytase expression system via genetic engineering which will enable the purification and utilization of working quantities of relatively pure enzyme.

The *E. coli* appA gene encodes a periplasmic enzyme that exhibits both acid phosphatase and phytase activity (see, Greiner et al.,1993). Based on a survey of purified phytases from several microbial sources, the native enzyme from *E. coli* exhibits the highest reported activity (see, Wyss et al., 1999). Furthermore, the enzyme exhibits a single pH optimum of 4.5 for phytase activity and a temperature optimum of ~60° C. Therefore, based on its established high intrinsic activity, low pH optimum, and inherent temperature resistance, the *E. coli* phytase represents an excellent starting point from which to begin directed evolution of a thermostable phytase for commercial feed and various other phytase applications.

The DNA sequence of the complete *E. coli* K-12 appA gene was originally reported by Dassa et al. (1990). Since that original report, however, a number of appA gene variants (naturally occurring or laboratory generated) have been described. Ostanin et al. (1992) used site-directed mutagenesis to examine the catalytic importance of 2 histidine and 4 arginine residues which are conserved in a number of acid phosphatases. The replacement of Arg16(R16A) or His17 (H17N) within the conserved N-terminal RHGXRXP (SEQ ID No. 30) motif of the *E. coli* AppA protein completely abolished activity on p-nitrophenyl phosphate (pNPP). Mutagenesis of Arg20 (R20A), Arg92 (R92A) and His303 (H303A) resulted in proteins with only 0.4% the activity of the wild-type (WT) enzyme while replacement of Arg63 (R63A) did not affect activity. Site directed mutagenesis experiments, designed to explore the role of Asp304 as a proton donor, demonstrated only small decreases in Km values of the substrate pNPP for the mutants D304A and D304Q (Ostanin et al., 1993). However, Vmax values were greatly reduced.

Several bacterial strains isolated from the contents of pig colon were found to produce phytase activity. One strain, identified as an *E. coli*, had the highest activity. The appA gene (designated appA2) from this *E. coli* strain was found to be 95% identical with the *E. coli* K-12 appA gene sequence (Rodriguez et al., 1999). This corresponded to a six amino acid differences between the two proteins: S102P, P195S, S197L, K202N, K298M and T299A. The purified AppA2 protein (expressed in *Pichia pastoris*), however, had a dramatically lower activity than the purified AppA enzyme (Greiner et al., 1993; Wyss et al., 1999; Golovan et al., 2000).

Wild-type AppA and several mutants generated by site directed mutagenesis were expressed in *P. pastoris* to investigate the effect of N-linked glycosylation on the thermostability profile of the AppA protein (Rodriguez et al., 2000). AppA mutants A131N/V143N/D207N/S211N, C200N/D207N/S211N and A131N/V134N/C200N/D207N/S211N were examined for levels of glycosylation and phytase activity. Despite no enhancement of glycosylation, mutant C200N/D207N/S211N was more active at pH 3.5-5.5 and retained more activity after heat treatment than the WT protein produced in *P. pastoris*. In addition, its apparent catalytic efficiency $k_{cat}/K_m$ for phytate was improved 5.3× over that of the AppA protein. The authors speculate that the C200N mutation might eliminate the disulfide bond between the G helix and the GH loop in the alpha-domain of the protein (Lim et al., 2000) thereby modulating domain flexibility and catalytic efficiency and thermos/ability.

Three recent U.S. patents (U.S. Pat. Nos. 5,876,997, 6,110,719 and 6,190,897) by Kretz describe the sequence of the appA gene from the *E. coli* B strain. The AppA proteins from strains K-12 and B are identical except for two amino acid differences: K276M and T277A (residue numbering is based on the mature polypeptide). These same two amino acid changes have been discovered in the appA2 gene (Rodriguez et al., 1999).

A major source of potential genetic diversity for directed evolution studies is in nature, where phytases are found widely distributed (Wodzinski et al., "Phytase", In *Advances in Applied Microbiology*, vol. 42, Academic Press, San Diego, Calif. (1996) pp. 263-302). They are found in many bacteria, fungi, and plants. Phytase activity has been detected in several bacterial sources which include the enteric bacteria *E. coli* (Dassa et al, 1990), *Enterobacter* spp. and *Klebsiella* spp. (Yoon et al., 1996; Greiner et al., 1997; Shah et al., 1990). Active phytase (AppA) gene variants have been successfully amplified from an *E. coli* strain isolated from a pig colon (Rodriguez et al., 1999) as well as from *E. coli* strain B (9). Besides the AppA gene product, the *E. coli* agp gene encodes an enzyme that has both glucose-1-phosphatase and phytase activities (Golovan et al., 2000; Kretz, U.S. Pat. No. 6,110,719). This is not entirely surprising given the fact that the two proteins share about 30% overall sequence identity including many of the amino acid residues at the conserved active site (Dassa et al., 1990). Therefore, amplification and/or cloning of the phytase variants from enteric strains (e.g., belonging to such genera as *Escherichia, Salmonella, Shigella, Enterobacter* and *Klebsiella*) is likely to generate AppA gene variants useful in the directed evolution of a commerically viable *E. coli* phytase (AppA) enzyme.

SUMMARY OF THE INVENTION

Provided herein are recombinant phytase proteins, as well as nucleic acids encoding said proteins and transformed cells that express said proteins. Also provided are methods of making and using the phytase proteins.

As will be appreciated, an advantage of the present invention is that polynucleotides have been isolated which provide the capability of isolating further polynucleotides which encode proteins having phytase activity.

In one aspect of the invention, a group of modified amino acid sequences for variants of the *E. coli* AppA phytase or for variants of natural variants of the AppA *E. Coli* phytase are provided. These modified phytase amino acid sequences have improved phytase characteristics and further comprise a modification of at least one amino acid sequence position selected from the group of residue(s) corresponding to residue(s) 26, 43, 54, 73, 113, 126, 184, 228, 384 and 410 in the mature phytase. In an additional aspect of the invention, these modified phytase amino acid sequences comprise a modification of at least one amino acid sequence position that is located within 5 amino acid residues either upstream or downstream of the amino acid sequence positions selected form the group of residue(s) corresponding to residues 26, 43, 54, 73, 113, 126, 184, 228, 384 and 410. In a further aspect of the invention, with respect to the mature folded protein, these modified phytase amino acid sequences comprise a modification of at least one amino acid sequence position that has their alpha carbons at least within 6Å of the alpha carbons of the amino acid residue(s) selected from the group of residue(s) corresponding residue(s) 26, 43, 54, 73, 113, 126, 184, 228, 384 and 410 in the mature phytase. In yet a further aspect of the invention, the modified phytases comprise at least a combination of at least two of the above mentioned modifications.

It will be understood in the art that any of the polynucleotide sequences encoding an amino acid sequence for a AppA phytase or for a natural variant of an AppA phytase, as provided herein, can serve as a starting sequence for mutagenesis screening of phytases with improved phytase characteristics. In addition, polynucleotide sequences which have already gone through one round of mutagenesis, in which the resulting codons encode amino acid residues which have been altered from their native sequence, can also serve as a starting sequence for further rounds of mutagenesis as described herein.

In one aspect of the invention, various Modified AppA sequences are screened for improved phytase characteristics. It will be understood in the art that improved phytase characteristics encompass improved expression; improved thermostability; improved specific activity and improved pH optimum.

As will be appreciated, an advantage of the present invention is that, by virtue of providing a protein having phytase activity, it is possible to produce, through recombinant means, a host cell which is capable of producing the protein having phytase activity in relatively large quantities.

Yet another advantage of the present invention is that commercial application of proteins having phytase activity is made practical. For example, the present invention provides animal feed incorporating the phytase described herein.

Other objects and advantages of the present invention will become apparent from the following detailed specification.

BRIEF DESCRIPTION OF THE DRAWINGS

FIG. 12 show the amino acid sequence of the 18B2 control AppA phytase and locations of variations in the sequence found in different mutants of the invention. The composite Bacillus signal sequence (residues 1-30) is underlined and the conserved RHGXRXP (SEQ ID No. 30) motif characteristic for histidine phosphatases is in bold italics. Only differences from the control sequence are indicated for the AppA sequences of the identified mutants. Each of the mutant amino acid sequences comprises a substitution at residue 143 (corresponding to residue 113 of the mature E. coli K-12 AppA phytase). Bacillus subtilis hosts expressing a mutant AppA shown in this figure had improved phytase activity as compared with clones expressing the control AppA.

FIG. 14 shows the amino acid sequence of several AppA proteins. The control 18B2 sequence is as described in FIG. 12, as is the AppA sequence for the PHY850 mutant. The three clones having the highest activity in the assay described in Example 5 and illustrated in FIG. 13 were also sequenced. The sequences for PHY1361 and PHY1363 are shown. A third mutant, PHY1373, had a sequence identical to 1363. All of the higher-activity mutants comprised a change in residue 414 (corresponding to residue 384 of the mature E. coli K-12 AppA phytase).

FIG. 18 shows the percent phytase activity in culture supernatants heated to elevated temperatures as compared with the activity of the same supernatant at 37° C., as described in Example 7C. The supernatant was taken from cultures of Bacillus clones expressing various appA genes. The plot shows that the thermostability of all of the mutants tested was similar to the control AppA of clone 18B2.

FIG. 19 shows the oligonucleotide primers and combinations thereof used to amplify AppA related sequences.

FIG. 20 shows a table of an alignment of amino acid sequences of E. coli K-12 and AppA natural variants (full and partial sequences).

FIG. 21 shows a table of an alignment of polynucleotide sequences of E. coli and AppA natural variants (full and partial sequences).

DETAILED DESCRIPTION OF THE INVENTION

Figure 1:
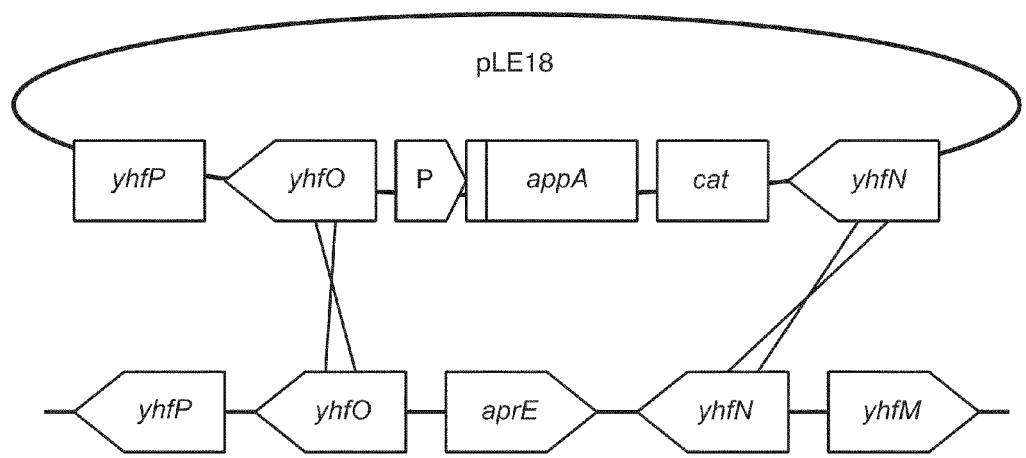
FIG. 1 depicts schematically the integration of the appA gene from plasmid pLE18 (top) into the genome (chromosomal expression locus) of B. subtilis strain OS21.10 (bottom). The inserted sequence contains the PstS promoter sequence (P), the sequence encoding mature E. coli K-12 AppA (appA), the composite Bacillus signal sequence (intervening P and appA), and the chloramphenicol resistance gene (cat).

The present invention describes the generation, identification and characterization of a novel group of AppA gene mutants or of natural variants of AppA gene mutants. These phytase mutants were created with a random mutagenesis approach to generate genetic diversity. The mutants disclosed herein have increased phytase activity and/or are secreted in increased amounts from host cells. These mutants contain unique amino acid changes that could not have been predicted by a rational design approach. The invention also provides means for optimizing the secretion of the E. coli phytase enzyme in a Generally Regarded As Safe (GRAS) host such as Bacillus subtilis.

The present invention also describes the isolation and characterization of a novel group of nucleotide gene sequences that encode natural variants of the E. coli AppA gene. These variant genes or fragments thereof were PCR amplified from various isolated enteric strains or from bacterial communities present in phytate enrichment cultures. These natural variants provide diverse sources of sequences for the production of chimeric phytases with novel and improved characteristics as compared with known and/or naturally occurring phytases.

I. Definitions

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acid sequences are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

"Protein", as used herein, includes proteins, polypeptides, and peptides. As will be appreciated by those in the art, the nucleic acid sequences of the invention, as defined below and further described herein, can be used to generate protein sequences.

As used herein, the term "phytase" or "phytase activity" refers to a protein or polypeptide which is capable of catalyzing the hydrolysis of phytate to (1) myo-inositol and/or (2) mono-, di-, tri-, tetra- and/or penta-phosphates thereof and (3) inorganic phosphate. For example, enzymes having catalytic activity as defined in Enzyme Commission EC number 3.1.3.8, or EC number 3.1.3.26.

"AppA phytase", as used herein, refers to a phytase protein derived from an Eschericia species, preferably from an E. coli strain, most preferably from the E. coli K-12 strain. In one embodiment, the AppA phytase comprises the amino acid sequence disclosed in GenBank accession numbers P07102 and M58708, and the translation of the appA gene disclosed in Genbank accession number NC_000913, each of which are incorporated herein. Likewise, the phrase "appA ", "appA gene", or "gene encoding AppA" and grammatical equivalents thereof refers to a nucleic acid comprising a sequence encoding an AppA, preferably a nucleic acid derived from an Eschericia species, most preferably from an E. coli strain such as the E. coli K-12 strain. In one embodiment, the appA gene has the sequence disclosed in Genank accession number M58708, or the sequence designate "appA gene" disclosed in GenBank accession number NC_000913, each of which are incorporated herein. In a preferred embodiment, an appA gene comprises a sequence encoding residues 31-440 of the amino acid sequence designated EBC18B2 in FIG. 12.

The term "amino acid residue equivalent to", "amino acid corresponding to" and grammatical equivalents thereof is used herein to refer to a amino acid residue of a protein having the similar position and effect as that indicated in a particular amino acid sequence of a particular protein. For example, the residue of an AppA protein equivalent to amino acid 46 of the EBC18B2AppA protein of FIG. 12 is a residue equivalent to the first Arginine of the conserved RHGXRXP (SEQ ID No. 30) motif characteristic of histide phosphatases such as the *E. coli* AppA phytase. The amino acid sequence and crystal structure of many phytases are known (see e.g., Lim et al., 2000; Pandey et al., 2001; Kerovuo et al., 2000; and Kostrewa et al., 1997). The person of skill in the art will recognize the equivalence of specified residues in comparable phytase proteins.

By "mature phytase" and grammatical equivalents thereof is meant a phytase following signal processing, such as removal of secretion signal sequences. In a preferred embodiment, the "mature AppA phytase of FIG. 12" and grammatical equivalents thereof refers to a phytase having the sequence from residue 31 to residue 440 of the sequence designated EBC18B2 in FIG. 12. This sequence correspond to residues 23 to 432 of the AppA protein encoded by the appA gene of *E. coli* strain K-12.

As used herein, the phrase "composite *Bacillus* signal sequence", "composite signal sequence of *Bacillus* origin" and grammatical equivalents thereof refers to a signal sequence, preferably a secretion signal sequence, having the sequence of residues 1-30 of the sequence designated EBC18B2 in FIG. 12.

In the broadest sense, by "nucleic acid sequence", "polynucleotide" or "oligonucleotide" or grammatical equivalents herein means at least two nucleotides covalently linked together. A nucleic acid sequence of the present invention will generally contain phosphodiester bonds, although in some cases, as outlined below, nucleic acid sequence analogs are included that may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805(1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644, 048), phosphorodithioate (Briu et al., J. Am. Chem. Soc. 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34-17 (1994); Tetrahedron Lett. 37:743 (1996)) and nonribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) ppl69-176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological or food processing environments.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which include peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4°C drop in Tm for an internal mismatch. With the non-ionic PNA backbone, the drop is closer to 7-9°C. Similarly, due to their non-ionic nature, hybridization of the bases attached to these backbones is relatively insensitive to salt concentration. In addition, PNAs are not degraded by cellular enzymes, and thus can be more stable.

The nucleic acid sequences may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid sequence may be DNA, both genomic and cDNA, RNA or a hybrid, where the nucleic acid sequence contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid sequence, each containing a base, are referred to herein as a nucleoside.

The term "identical" in the context of two nucleic acid sequences or polypeptide sequences refers to the residues in the two sequences that are the same when aligned for maximum correspondence, as measured using one of the following sequence comparison or analysis algorithms.

"Optimal alignment" is defined as an alignment giving the highest percent identity score. Such alignment can be performed using a variety of commercially available sequence analysis programs, such as the local alignment program LALIGN using a ktup of 1, default parameters and the default PAM. A preferred alignment is the pairwise alignment performed using the CLUSTAL-W program in MACVECTOR, operated in "slow" alignment mode using default parameters, including an open gap penalty of 10.0, an extend gap penalty of 0.1, and a BLOSUM30 similarity matrix. If a gap needs to be inserted into a first sequence to optimally align it with a second sequence, the percept identity is calculated using only the residues that are paired with a corresponding amino acid residue (i.e., the calculation does not consider residues in the second sequences that are in the "gap" of the first sequence).

Optimal alignment of sequences for comparison can also be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Optimal alignment of sequences for comparison can be conducted on natural variants of AppA phytase to find residues in AppA phytase which correspond to the identical residue in a natural variant of AppA phytase.

"Percent sequence identity", with respect to two amino acid or polynucleotide sequences, refers to the percentage of residues that are identical in the two sequences when the sequences are optimally aligned. Thus, 80% amino acid sequence identity means that 80% of the amino acids in two optimally aligned polypeptide sequences are identical. Percent identity can be determined, for example, by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M.O. in "Atlas of Protein Sequence and Structure", M.O. Dayhoff ed.,* 5 Suppl. 3:353-358, National Biomedical Research Foundation, Washington, D.C., which adapts the local homology algorithm of Smith and Waterman (1981) Advances in Appl. Math. 2:482489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above.

An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid sequence is considered similar to a phytase nucleic acid sequence of this invention if the smallest sum probability in a comparison of the test nucleic acid sequence to a phytase nucleic acid sequence is less than about 0.1, more preferably less than about 0.01, and most preferably less than about 0.001. Where the test nucleic acid sequence encodes a phytase polypeptide, it is considered similar to a specified phytase nucleic acid sequence if the comparison results in a smallest sum probability of less than about 0.5, and more preferably less than about 0.2.

The phrase "substantially identical" in the context of two nucleic acid sequences or polypeptides thus typically means that a polynucleotide or polypeptide comprises a sequence that has at least 60% sequence identity, preferably at least 80%, more preferably at least 90% and most preferably at least 95%, compared to a reference sequence using the programs described above (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

"Hybridization" includes any process by which a strand of a nucleic acid sequence joins with a second nucleic acid sequence strand through base-pairing. Thus, strictly speaking, the term refers to the ability of a target sequence to bind to a test sequence, or vice-versa.

"Hybridization conditions" are typically classified by degree of "stringency" of the conditions under which hybridization is measured. The degree of stringency can be based, for example, on the calculated (estimated) melting temperature (Tm) of the nucleic acid sequence binding complex or probe. Calculation of Tm is well known in the art (see, e.g. page 9.50-9.51 of Sambrook (1989), below). For example, "maximum stringency" typically occurs at about Tm-5_C (5_below the Tm of the probe); "high stringency" at about 5-10_below the Tm; "intermediate stringency" at about 10-20_below the Tm of the probe; and "low stringency" at about 20-25_below the Tm. In general, hybridization conditions are carried out under high ionic strength conditions, for example, using 6×SSC or 6×SSPE. Under high stringency conditions, hybridization is followed by two washes with low salt solution, for example 0.5×SSC, at the calculated temperature. Under medium stringency conditions, hybridization is followed by two washes with medium salt solution, for example 2×SSC. Under low stringency conditions, hybridization is followed by two washes with high salt solution, for example 6×SSC. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, one will typically desire to employ relatively stringent conditions to form the hybrids, e.g., one will select relatively high temperature conditions. Hybridization conditions, including moderate stringency and high stringency, are provided in Sambrook et al.,Molecular Cloning: A Laboratory Manual, Second Edition, Cold Spring Harbor Press (1989); Sambrook et al., Molecular Cloning, A Laboratory Manual, 3d Ed., Cold Spring Harbor Laboratory Press, Cold Spring Harbor, N.Y. (2001), incorporated herein by reference.

The term "complementary", in the context of a nucleic acid sequence, means a nucleic acid sequence having a sequence relationship to a second nucleic acid sequence such that there is perfect alignment of Watson-Crick base pairs along the entire length of both nucleic acid sequences.

The term "isolated" or "substantially purified" means that a material is removed from its original environment (e.g., the natural environment if it is naturally occurring). For example, the material is said to be "substantially purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. A nucleic acid sequence or protein is said to be purified, for example, if it gives rise to essentially one band in an electrophoretic gel.

The present invention provides for the production of recombinant nucleic acids and proteins. By "recombinant" and grammatical equivalents thereof is meant produced using recombinant technology, whereby novel nucleic acids are made (recombinant nucleic acids) and proteins are produced therefrom (recombinant proteins). Such techniques are well known in the art and many are described in great detail herein. In a broad sense, a recombinant nucleic acid sequence may be any nucleic acid sequence not in its naturally occurring form, whether it be a sequence isolated from its naturally occurring adjoining sequence, or combined with other sequences with which it was not joined in nature to form a new nucleic acid sequence, such as in a vector. Recombinant nucleic acid sequences also includes those that are produced from recombinant nucleic acid sequences, for example complementary sequences made through polymerization, additional copies made though replication, or RNA transcribed from recombinant DNA. Recombinant protein is protein produced by translation of recombinant nucleic acid sequences.

As used herein in referring to phytate hydrolyzing enzymes (phytases), the term "derived from" is intended not only to indicate a phytase produced or producible by a strain of the organism in question, but also a phytase encoded by a DNA sequence isolated from such strain and produced in a host organism containing such DNA sequence. Additionally, the term is intended to indicate a phytase which is encoded by a DNA sequence of synthetic and/or cDNA origin and which has the identifying characteristics of the phytase in question. To exemplify, "phytases derived from *E. coli*" refers to those enzymes having phytase activity which are naturally-produced by *E. coli*, as well as to phytases like those produced by *E. coli* sources but which, through the use of genetic engineering techniques, are produced by non-*E. coli* organisms transformed with a nucleic acid sequence encoding said phytases.

The present invention encompasses phytate hydrolyzing enzymes that are equivalent to those that are derived from the particular microbial strain mentioned. Being "equivalent," in this context, means that the phytate hydrolyzing enzymes are encoded by a polynucleotide capable of hybridizing to the polynucleotide having the sequence as shown in any one of Figures  under conditions of medium to high stringency. Being equivalent means that the phytate hydrolyzing enzyme comprises at least 50% identity, preferably at least 55% identity, more preferably at least 60% identity, still more preferably at least 65% identity, yet more preferably at least 70% identity, even more preferably at least 75% identity, again more preferably at least 80% identity, yet again more preferably at least 85% identity, still more preferably at least 95% identity, and most preferably at least 96%, 97%, 98% or 99%, up to about 100% identity to the phytate hydrolyzing enzyme having the amino acid sequence disclosed in one of the amino acid sequences of FIG. 20**.

The present invention also encompasses mutants, variants and derivatives of the phytate hydrolyzing enzymes of the present invention as long as the mutant, variant or derivative phytate hydrolyzing enzyme is able to retain at least one characteristic activity of the naturally occurring phytate hydrolyzing enzyme.

As used herein, the term "mutants or variants", when referring to phytate hydrolyzing enzymes, refers to phytate hydrolyzing enzymes obtained by alteration of the naturally occurring amino acid sequence and/or structure thereof, such as by alteration of the DNA nucleotide sequence of the structural gene and/or by direct substitution and/or alteration of the amino acid sequence and/or structure of the phytate hydrolyzing enzyme.

By "natural variant of AppA phytase" is herein meant amino acid sequences which when compared using sequence comparison and analysis alorithims as described herein show substantial identity and are immunologically cross-reactive with the mature *E. Coli* phytase designated EBC18B2 of FIG. 12. "Substantial identity" is described herein. A particular amino acid residue of the mature phytase designated EBC18B2 of FIG. 12 corresponds to an identical amino acid residue of a natural variant of EBC18B2 when an optimal alignment algorithm analysis is performed as described herein.

By "natural variant" (of AppA phytase) is meant a naturally occurring amino acid sequence for an enzyme having phytase activity, which has been isolated from a source other than E. Coli, such as but not limited to *Shigella flexnarii, Shigella sonnei, Pasturella aerogenes, Entrobacter cloacae, Entrobacter agglomerans, E. Coli* strain B, and *Proteus vulgaris*. A "natural variant" encompasses a native amino acid sequence "substantially identical" (as previously defined), to the amino acid sequence of the mature E. Coli phytase sequence designated EBC18B2 of FIG. 12. A natural variant includes any one of the amino acid sequences listed in FIG. 20 with the exception of the E. Coli sequence.

The term "derivative" or "functional derivative" as it relates to phytase is used herein to indicate a derivative of phytase which has the functional characteristics of phytase of the present invention. Functional derivatives of phytase encompass naturally occurring, synthetically or recombinantly produced peptides or peptide fragments, mutants or variants which may have one or more amino acid deletions, insertions or substitutions which have the general characteristics of the phytase of the present invention.

The term "functional derivative" as it relates to nucleic acid sequences encoding phytase is used throughout the specification to indicate a derivative of a nucleic acid sequence which has the functional characteristics of a nucleic acid sequence which encodes phytase. Functional derivatives of a nucleic acid sequence which encode phytase of the present invention encompass naturally occurring, synthetically or recombinantly produced nucleic acid sequences or fragments, mutants or variants thereof which may have one or more nucleic acid deletions, substitutions or insertions and encode phytase characteristic of the present invention. Variants of nucleic acid sequences encoding phytase according to the invention include alleles and variants based on the degeneracy of the genetic code known in the art. Mutants of nucleic acid sequences encoding phytase according to the invention include mutants produced via site-directed mutagenesis techniques (see for example, Botstein, D. and Shortle, D., 1985, Science 229:1193-1201 and Myers, R. M., Lerman, L. S., and Maniatis, T., 1985, Science 229: 242-247), error-prone PCR (see for example, Leung, D. W., Chen, E., and Goeddel, D. V., 1989, Technique 1: 11-15; Eckert, K. A. and Kunkel, T. A., 1991, PCR Methods Applic. 1: 17-24; and Cadwell, R. C. and Joyce, G. F., 1992, PCR Methods Applic. 2: 28-33) and/or chemical-induced mutagenesis techniques known in the art (see for example, Elander, R. P., Microbial screening, Selection and Strain Improvement, in Basic Biotechnology, J. Bullock and B. Kristiansen Eds., Academic Press, New York, 1987, 217).

"Expression vector" means a DNA construct comprising a DNA sequence which is operably linked to a suitable control sequence capable of effecting the expression of the DNA in a suitable host. Such control sequences may include a promoter to effect transcription, an optional operator sequence to control such transcription, a sequence encoding suitable ribosome-binding sites on the mRNA, and sequences which control termination of transcription and translation. Different cell types are preferably used with different expression vectors. A preferred promoter for use in *Trichoderma reesei* is cbh1. Preferred promoters for vectors used in *Bacillus subtilis* are the PstS and AprE promoters; a preferred promoter used in *E. coli* is the Lac promoter and a preferred promoter used in *Aspergillus niger* is glaA. The vector may be a plasmid, a phage particle, or simply a potential genomic insert. Once transformed into a suitable host, the vector may replicate and function independently of the host genome, or may, under suitable conditions, integrate into the genome itself.

In the present specification, plasmid and vector are sometimes used interchangeably. However, the invention is intended to include other forms of expression vectors which serve equivalent functions and which are, or become, known in the art. Thus, a wide variety of host/expression vector combinations may be employed in expressing the DNA sequences of this invention. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage 1, e.g., NM989, and other DNA phages, e.g., M13 and filamentous single stranded DNA phages, yeast plasmids such as the 2m plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences.

Expression techniques using the expression vectors of the present invention are known in the art and are described generally in, for example, Sambrook et al., Molecular Cloning: A Laboratory Manual, Second Edition, Cold Spring Harbor Press (1989); and Sambrook et al., Molecular Cloning, A Laboratory Manual, 3d Ed., Cold Spring Harbor Laboratory Press, Cold Spring Harbor, N.Y. (2001). Often, such expression vectors including the DNA sequences of the invention are transformed into a unicellular host by direct insertion into the genome of a particular species through an integration event (see e.g., Bennett & Lasure, More Gene Manipulations in Fungi, Academic Press, San Diego, pp. 70-76 (1991) and articles cited therein describing targeted genomic insertion in fungal hosts, incorporated herein by reference).

"Host strain" or "host cell" means a suitable host for an expression vector comprising DNA according to the present invention. Host cells useful in the present invention are generally procaryotic or eucaryotic hosts, including any transformable microorganism in which expression can be achieved. For example, host strains can be *Trichoderma reesei, Bacillus subtilis, Escherichia coli, Trichoderma longibrachiatum*, and *Saccharomyces cerevisiae*. Host cells are transformed or transfected with vectors constructed using recombinant DNA techniques. Such transformed host cells are capable of both replicating vectors encoding phytase and its variants (mutants) or expressing the desired peptide product.

Examples of appropriate expression hosts include: bacterial cells, such as *E. coli, Streptomyces, Salmonella typhimurium*; fungal cells, such as *Bacillus, Trichoderma, Aspergillus* and *Penicillium*; insect cells such as *Drosophila* and *Spodoptera* Sf9; animal cells such as CHO, COS, HEK 293 or Bowes melanoma; plant cells, etc. The selection of an appropriate host is deemed to be within the scope of those skilled in the art from the teachings herein. It should be noted that the invention is not limited by the particular host cells employed.

II. Phytase Enzymes and Nucleic Acid Sequences Encoding Phytase Enzymes

One aspect of the present invention provides proteins or polypeptides which are capable of catalyzing the hydrolysis of phytate and releasing inorganic phosphate; for example, enzymes having catalytic activity as defined in Enzyme Commission EC number 3.1.3.8, or in EC number 3.1.3.26. In one preferred embodiment, the invention provides a so-called 3-phytase. The present invention additionally encompasses polynucleotides (e.g., DNA) which encode such phytate hydrolyzing proteins or polypeptides.

Preferably, the phytase and/or polynucleotides encoding the phytase according to the present invention is derived from a bacteria or is a derivative thereof. Preferably, the bacteria is an enteric bacteria such as *Escherichia* spp., including *E. coli* K-12 and *E. coli* B; *Enterobacter* spp., including *Enterobacter cloacae* and *Enterobacter agglomerans; Klebsiella* spp.; *Salmonella* spp.; and *Shigella* spp., including *Sligella flexnarii* and *Shigella sonnei*, as well as other bacteria such as *Pasturella* spp., including *Pasturella aerogenes*; and *Proteus* spp., including *Proteus vulgaris*.

According to a preferred embodiment, the phytase and/or polynucleotide encoding the phytase of the present invention is in a substantially purified form, i.e., present in a particular composition in a higher or lower concentration than exists in a naturally occurring or wild type organism or in combination with components not normally present upon expression from a naturally occurring or wild type organism.

The invention encompasses phytate hydrolyzing proteins and peptides comprising at least 50% identity, preferably at least 55% identity, more preferably at least 60% identity, still more preferably at least 65% identity, yet more preferably at least 70% identity,. even more preferably at least 75% identity, again more preferably at least 80% identity, yet again more preferably at least 85% identity, still more preferably at least 95% identity, and most preferably at least 96%, 97%, 98% or 99%, up to about 100% identity to the phytate hydrolyzing enzyme having the amino acid sequence disclosed in FIGS. 12, 14 or 20.

Figure 21B:
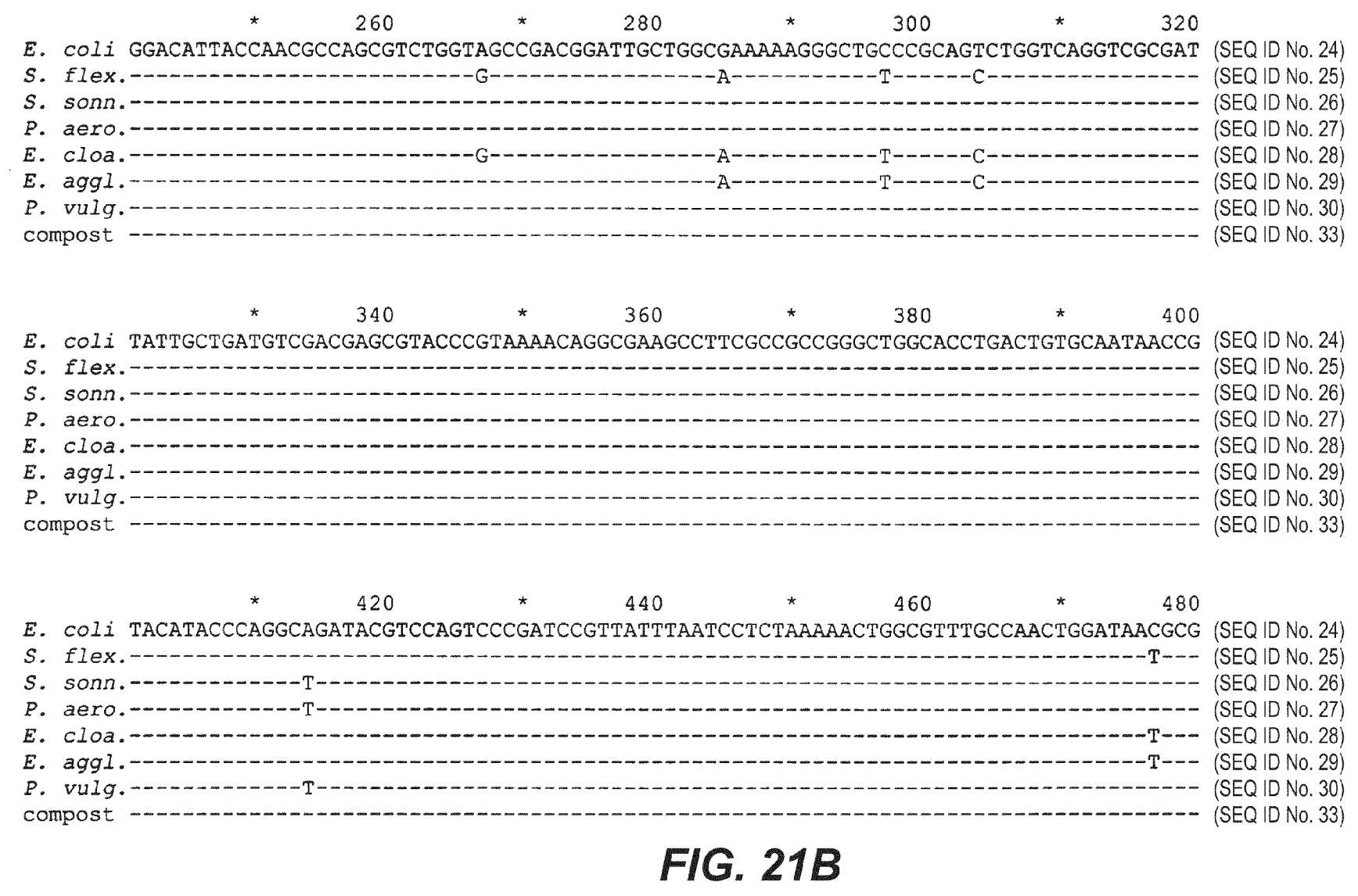
Figure 21C:
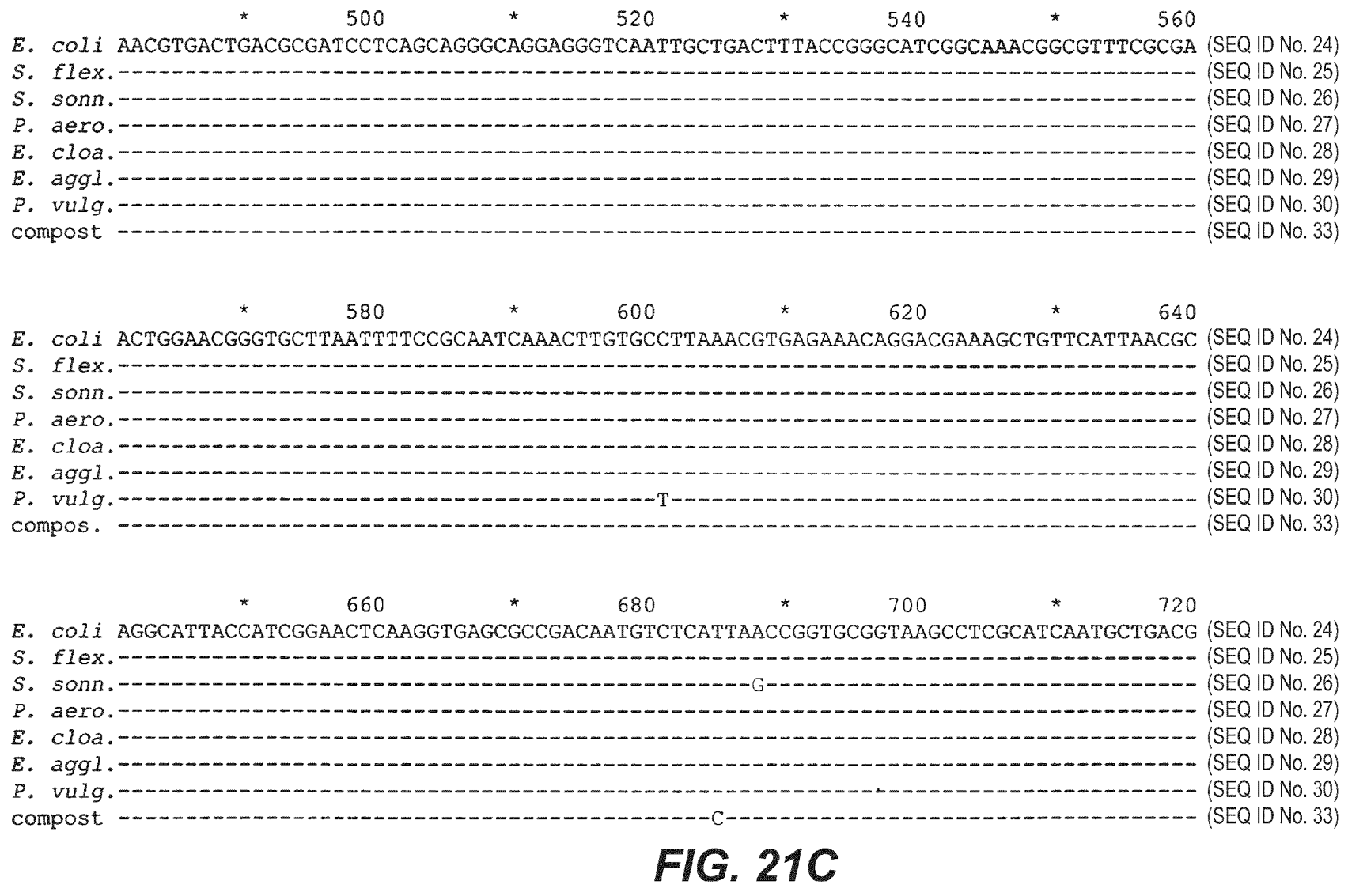

The invention further encompasses polynucleotides, e.g., DNA, which encode phytate hydrolyzing enzymes derived from bacterial sources, or functional derivatives thereof. The bacterial sources may include *Eschericia* spp., *Enterobacter* spp., *Shigella* spp., *Pasturella* spp. and *Proteus* spp., and the polynucleotides comprise a sequence having at least 65% identity, at least 70% identity, at least 75% identity, at least 80% identity, at least 85% identity, at least 90% identity at least 95%, 96%, 97%, 98%, 99% and 100% identity to any one of the polynucleotide sequences disclosed in FIG. 21, as long as the enzyme encoded by the polynucleotide is capable of catalyzing the hydrolysis of phytate and releasing inorganic phosphate. In a preferred embodiment, the polynucleotide encoding the phytate hydrolyzing enzyme has any one of the polynucleotide sequences as shown in FIG. 21, or is capable of hybridizing to any one of the polynucleotide sequences as shown in FIG. 21 or its complement, or is complementary to any one of the polynucleotide sequences as shown in FIG. 21. As will be understood by the skilled artisan, due to the degeneracy of the genetic code, a variety of polynucleotides can encode the phytate hydrolyzing enzyme disclosed in FIG. 21. The present invention encompasses all such polynucleotides.

Obtaining Polynucleotides Encoding a Phytate Hydrolyzing Enzyme

The nucleic acid sequence encoding a phytate hydrolyzing enzyme may be obtained by standard procedures known in the art from, for example, cloned DNA (e.g., a DNA "library"), by chemical synthesis, by cDNA cloning, by PCR, or by the cloning of genomic DNA, or fragments thereof, substantially purified from a desired cell, such as a bacterial species (See, for example, Sambrook et al., 2001, Molecular Cloning, A Laboratory Manual, 3d Ed., Cold Spring Harbor Laboratory Press, Cold Spring Harbor, N.Y.; Glover, DM and Hames, BD (Eds.), 1995, DNA Cloning 1: A Practical Approach and DNA Cloning 2: A Practical Approach, Oxford University Press, Oxford). Nucleic acid sequences derived from genomic DNA, and derivatives thereof, may contain regulatory regions in addition to coding regions.

In the molecular cloning of the gene from genomic DNA, DNA fragments are generated, some of which will comprise at least a portion of the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis, PCR and column chromatography.

Once nucleic acid sequence fragments are generated, identification of the specific DNA fragment encoding a phytate hydrolyzing enzyme may be accomplished in a number of ways. For example, a phytate hydrolyzing enzyme encoding gene of the present invention or its specific RNA, or a fragment thereof, such as a probe or primer, may be isolated and labeled and then used in hybridization assays to detect a generated gene. (Benton, W. and Davis, R., 1977, *Science* 196:180; Grunstein, M. and Hogness, D., 1975, *Proc. Natl. Acad. Sci. USA* 72:3961). Those DNA fragments sharing substantial sequence similarity to the probe will hybridize under medium to high stringency.

The present invention encompasses phytate hydrolyzing enzymes derived from bacterial species (esp., *Eschericia, Enterobacter, Shigella, Pasturella* and *Proteus* species), and derivatives thereof, which are identified through nucleic acid sequence hybridization techniques using one of the sequences disclosed in FIG. 21, or a suitable portion or fragment thereof (e.g., at least about 10-15 contiguous nucleotides), as a probe or primer and screening nucleic acid sequences of either genomic or cDNA origin. Nucleic acid sequences encoding phytate hydrolyzing enzymes derived from bacterial species, and derivatives thereof, having at least 80% identity to one of the sequences of FIG. 21 or a portion or fragment thereof can be detected by DNA-DNA or DNA-RNA hybridization or amplification using probes, portions or fragments of the disclosed sequences. Accordingly, the present invention provides a method for the detection of a nucleic acid sequence encoding a phytate hydrolyzing enzyme encompassed by the present invention which comprises hybridizing part or all of a nucleic acid sequence of FIG. 21 with a nucleic acid sequence of either genomic or cDNA origin.

Also included within the scope of the present invention are polynucleotide sequences that are capable of hybridizing to one of the nucleotide sequences disclosed in FIG. 21 under conditions of medium to high stringency. In one embodiment, hybridization conditions are based on the melting temperature (Tm) of the nucleic acid sequence binding complex, as taught in Berger and Kimmel (1987, Guide to Molecular Cloning Techniques, Methods in Enzymology, Vol 152, Academic Press, San Diego Calif.) incorporated herein by reference, and confer a defined stringency. In this embodiment, "maximum stringency" typically occurs at about Tm-5_C (5_C below the Tm of the probe); "high stringency" at about 5_C to 10_C below Tm; "medium" or "intermediate stringency" at about 10_C to 20_C below Tm; and "low stringency" at about 20_C to 25_C below Tm. A maximum stringency hybridization can be used to identify or detect identical or near-identical polynucleotide sequences, while an intermediate or low stringency hybridization can be used to identify or detect polynucleotide sequence homologs.

The process of amplification as carried out in polymerase chain reaction (PCR) technologies is described in Dieffenbach CW and GS Dveksler (1995, PCR Primer, a Laboratory Manual, Cold Spring Harbor Press, Plainview N.Y.) A nucleic acid sequence of at least about 10 nucleotides and as many as about 60 nucleotides from the sequences of FIG. 21, preferably about 12 to 30 nucleotides, and more preferably about 25 nucleotides can be used as a probe or PCR primer.

A preferred method of isolating a nucleic acid sequence construct of the invention from a cDNA or genomic library is by use of polymerase chain reaction (PCR) using degenerate oligonucleotide probes prepared on the basis of the amino acid sequence of the protein having the amino acid sequence as shown in FIGS. 12, 14 or 20. For instance, the PCR may be carried out using the techniques described in U.S. Pat. No. 4,683,202.

In view of the above, it will be appreciated that the polynucleotide sequences provided in FIG. 21 are useful for obtaining identical or homologous fragments of polynucleotides from other species, and particularly from bacteria (e.g., enteric bacteria) which encode enzymes having phytase activity.

IV. Obtaining Derivative or Variant Phytate Hydrolyzing Enzymes

In one embodiment, the phytase proteins are derivative or variant phytase as compared to the wild-type sequence. That is, as outlined more fully below, the derivative phytase peptide will contain at least one amino acid substitution, deletion or insertion, with amino acid substitutions being particularly preferred. The amino acid substitution, insertion or deletion may occur at any residue within the phytase peptide.

Also included in an embodiment of phytase proteins of the present invention are amino acid sequence variants. These variants fall into one or more of three classes: substitutional, insertional or deletional variants. These variants may be prepared by site specific mutagenesis of nucleotides in the DNA encoding the phytase protein, using cassette or PCR mutagenesis or other techniques well known in the art, to produce DNA encoding the variant, and thereafter expressing the DNA in recombinant cell culture as outlined above. However, variant phytase protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the phytase protein amino acid sequence. The variants typically exhibit the same qualitative biological activity as the naturally occurring analogue, although variants can also be selected which have modified characteristics as will be more fully outlined below.

While the site or region for introducing an amino acid sequence variation may be predetermined, the mutation per se need not be predetermined. For example, in order to optimize the performance of a mutation at a given site, random mutagenesis may be conducted at the target codon or region and the expressed variants screened for the optimal combination of desired activity. Techniques for making substitution mutations at predetermined sites in DNA having a known sequence are well known, for example, M13 primer mutagenesis and PCR mutagenesis. Screening of the mutants is done using assays of phytase protein activities.

In a preferred embodiment, mutations are induced and preferred mutations are identified by directed evolution. By "directed evolution" and grammatical equivalents thereof is meant a process whereby random mutations are introduced into a phytase coding sequence and the products of such mutation are assayed for activity. Sequences encoding mutants having preferred activity are subsequently selected and subjected to further random mutagenesis, whereby mutants having preferred or more preferred activity are similarly identified.

In a preferred embodiment, mutant sequences are generated using error-prone PCR. By "error-prone PCR", "mutagenic PCR", and grammatical equivalents thereof is meant any PCR reaction wherein mutations of template nucleic acid sequences are produced with sufficient frequency to identify variant products using standard assays, as further described below. In most cases, a mutagenic frequency of approximately 0.1% is sufficient, although error-prone PCR methods producing higher or lower frequencies of mutation may be employed. Error-prone PCR methods are well known in the art. (See, e.g., Cadwell et al., 1992; Fromant et al., 1995; Melnikov et al., 1999), as are other methods of producing mutant sequences (see, e.g., Stemmer, 1994; Ling et al., 1997; Harayama, 1998; Henke et al., 1999). Random mutagenesis methods, coupled with selective assays, may be employed to identify mutant phytases having characteristics that could not be anticipated using rational design methods.

Amino acid substitutions are typically of single residues; insertions usually will be on the order of from about 1 to 20 amino acids, although considerably larger insertions may be tolerated, and may occur internally or at either terminus of the encoded protein. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the phytase are desired, substitutions are generally made in accordance with the following chart of conservative substitution residues:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and may elicit the same immune response as the naturally-occurring analogue, although variants also are selected to modify the characteristics of the phytase proteins as needed. Alternatively, the variant may be designed such that the biological activity of the phytase is altered. For example, glycosylation sites may be altered or removed. Such alterations may result in altered immunogenicity, as well.

In one aspect of the invention, provided herein are methods of producing an AppA phytase having modified activity. In a preferred embodiment, the method comprises providing a nucleic acid comprising a sequence encoding a signal sequence operable in a Bacillus species, preferably Bacillus subtilis, and a mature AppA phytase or mutant thereof, preferably comprising the sequence designated PHY679, PHY735, PHY736, PHY846, or PHY902 of FIG. 12. The method further comprises subjecting the nucleic acid to error-prone amplification, transforming a host cell with an expression construct comprising an amplification product of the amplification, and culturing the cell under conditions suitable for the cell to express the amplification product. In one embodiment, the method further comprises recovering the phytase. Also provided is an isolated and/or purified enzyme having phytase activity produced by the method.

In another aspect of the invention, a recombinant modified AppA phytase is provided. Preferably, the AppA phytase comprises an amino acid sequence which is modified at a position corresponding to residue 113 of a mature E. coli AppA phytase or of a natural variant thereof. In a preferred embodiment, the modification is a substitution. In one embodiment, the modification is a substitution of arginine for histidine. In a preferred embodiment, the AppA phytase comprises the sequence of residues 31-440 of the sequences designated PHY850 or PHY902 in FIG. 12. By "natural variant" is meant a naturally occurring amino acid sequence, encoding an enzyme having phytase activity, which has been isolated from a source other than E. Coli, such as but not limited to Shigella flexnarii, Shigella sonnei, Pasturella aerogenes, Entrobacter cloacae, Entrobacter agglomerans E. Coli strain B, and Proteus vulgaris.

In other embodiments, the AppA phytase or natural variant thereof comprises a modification of one or more amino acid residues corresponding to position 26, 43, 46, 54, 73, 113, 126, 184, 228, 384 and 410 of a mature E. coli AppA phytase or of a natural variant thereof. In addition to sites of mutation that are found to give improved phytase characteristics, residues adjacent to sites of mutation may similarly play a significant role in folding and secretion of the phytase so obtained. Specifically, modifications of neighboring residues up to 5 positions upstream or downstream in linear sequence may provide novel phytases with improved characteristics. In an additional embodiment, the AppA phytase comprises a modification of one or more residues which is located within 5 residues either upstream or downstream in linear sequence of the following residues: residue 26(the upstream and downstream residues include residues 21,22,23,24,25,27,28,29,30,31), residue 43 (the upstream and downstream residues include residues 38,39,40,41,42, 44,45,46,47,48), residue 46 (the upstream and downstream residues include residues 41, 42, 43, 44, 45, 47, 48, 49, 50, 51), residue 54 (the upstream and downstream residues include residues 49, 50, 51, 52, 53, 55, 56, 57, 58, 59), residue 73 (the upstream and downstream residues include residues 68,69,70,71,72,74,75,76,77,78), residue 126 (the upstream and downstream residues include residues 121,122,123,124, 125,127,128,129,130,131), residue 113 (the upstream and downstream residues include 108,109,110,111,112,114,115, 116,117,118), residue 184 (the upstream and downstream residues include 179, 180, 181, 182, 183, 185, 186, 187, 189), residue 228 (the upstream and downstream residues include 223, 224, 225, 226, 227, 229, 230, 231, 232, 233), residue 384 (the upstream and downstream residues include 379,380,381, 382,383,385,386,387,388,389), residue 410 (the upstream and downstream residues include 405,406,407,408,409,411, 412,413,414,415). In a preferred embodiment, the AppA phytase comprises a modification located within 4 residues of the above stated residues, more preferably located within 3 residues of the above stated amino acid residues, even more preferably located within 2 amino acid residues, most preferably located within 1 residue of the above stated amino acid residues. In a preferred embodiment, the AppA phytase comprises the sequence of amino acids 31-440 of the. sequence designated PHY679, PHY735, PHY736, or PHY846, PHY850 or PHY902 of FIG. 12 or PHY1361 or PHY1363 of FIG. 14. In yet another preferred embodiment, the AppA phytase comprises the sequence of amino acids 31-440 of the mature E. coli AppA phytase or any of the natural variants of AppA phytase listed in FIG. 20.

In addition, for the mature folded phytase, modifications of neighboring residues include s residues that have their alpha carbon atoms at least within 6 Δ of the alpha carbons of the amino acid residues corresponding to position 26, 43, 46, 54, 73, 113, 126, 184, 228, 384 and 410 of a mature E. coli AppA or of a natural variant thereof, preferably at least within 5Δ of the alpha carbons of the above mentioned amino acid residues in the folded protein, more preferably within 4Δ of the alpha carbons of the above mentioned residues, still more preferably within 3Δ of the alpha carbons of the above mentioned amino acid residues, and most preferably within 2Δ of the above mentioned amino acid residues in the mature folded phytase. The structure of the folded protein can be determined by x-ray crystallography or NMR as known in the art.

Covalent modifications of phytase polypeptides are included within the scope of this invention. One type of covalent modification includes reacting targeted amino acid residues of a phytase polypeptide with an organic derivatizing agent that is capable of reacting with selected side chains or the N-or C-terminal residues of a phytase polypeptide.

Derivatization with bifunctional agents is useful, for instance, for crosslinking a phytase to another protein. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleinides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the phytase polypeptide included within the scope of this invention comprises altering the native glycosylation pattern of the polypeptide. "Altering the native glycosylation pattern" is intended for purposes herein to mean deleting one or more carbohydrate moieties found in native phytase, and/or adding one or more glycosylation sites that are not present in the native polypeptide.

Addition of glycosylation sites to polypeptides may be accomplished by altering the amino acid sequence thereof The alteration may be made, for example, by the addition of, or substitution by, one or more serine or threonine residues to the native sequence phytase polypeptide (for O-linked glycosylation sites). The phytase amino acid sequence may optionally be altered through changes at the DNA level, particularly by mutating the DNA encoding the phytase polypeptide at preselected bases such that codons are generated that will translate into the desired amino acids.

Another means of increasing the number of carbohydrate moieties on the phytase polypeptide is by chemical or enzymatic coupling of glycosides to the polypeptide. Such methods are described in the art, e.g., in WO 87/05330 published 11 Sep. 1987, and in Aplin and Wriston, Crit. Rev. Biochem., pp. 259-306 (1981).

Removal of carbohydrate moieties present on the phytase may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Th6takura et al., Meth. Enzymol., 138:350 (1987).

Another type of covalent modification of phytase comprises linking the phytase polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Phytases of the present invention may also be modified to form chimeric molecules comprising a phytase polypeptide fused to another, heterologous polypeptide or amino acid sequence. In one embodiment, such a chimeric molecule comprises a fusion of a phytase polypeptide with a tag polypeptide which provides an epitope to which an anti-tag antibody can selectively bind. The epitope tag is generally placed at the amino-or carboxyl-terminus of the phytase polypeptide. The presence of such epitope-tagged forms of a phytase can be detected using an antibody against the tag polypeptide. Also, provision of the epitope tag enables the phytase to be readily purified by affinity purification using an anti-tag antibody or another type of affinity matrix that binds to the epitope tag. In a preferred embodiment, the chimeric molecule may comprise a fusion of a phytase polypeptide with an initial sequence or signal polypeptide, such as a secretion signal, of a different phytase or other protein. The fusion may involve the addition of a sequence from a protein, such as a phytase, which is native to the host cell in which the phytase is being expressed. Specific examples of this are provided in the Examples section, below. In a preferred embodiment, a chimeric phytase comprises the secretion signal of residues 1-30 of the sequence designated EBC18B2 in FIG. 12 fused to a mature phtyase protein or mutant thereof.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Also included with the definition of phytase in one embodiment are other phytase proteins from other organisms, which are cloned and expressed as outlined below. Thus, probe or degenerate polymerase chain reaction (PCR) primer sequences may be used to find other related phytases from fungi or other organisms. As will be appreciated by those in the art, particularly useful probe and/or PCR primer sequences include the highly conserved amino acid sequences and the known binding or catalytic sequences. For example, the phosphate binding region of phytase produced in various fungi is highly conserved. As is generally known in the art, preferred PCR primers are from about 15 to about 35 nucleotides in length, with from about 20 to about 30 being preferred, and may contain inosine as needed.

The conditions for the PCR reaction are well known in the art. The present invention further provides polynucleotide sequences coding for the enzyme comprising DNA sequences as shown in FIG. 21; a polynucleotide which encodes one of the amino acid sequences shown in FIGS. 12, 14, or 20; a polynucleotide which encodes a phytase which comprises an amino acid segment which differs from the sequences in FIG. 12, 14, or 20, provided that the polynucleotide encodes a derivative of the phytase specifically described herein; and a polynucleotide which encodes a phytase that comprises an amino acid sequence which differs from the sequences in FIGS. 12, 14 or 20, provided that the polynucleotide hybridizes under medium to high stringency conditions with a nucleic acid sequence comprising all or part of one off the nucleic acid sequences in FIG. 21.

The present invention also provides a polynucleotide encoding an enzyme having phytate hydrolyzing activity and including a nucleotide sequence as shown in FIG. 21; a polynucleotide which encodes the amino acid sequence as shown in FIGS. 12, 14 or 20; a polynucleotide which encodes a phytase which comprises an amino acid segment which s differs from the sequence in FIGS. 12, 14 or 20, provided that the polynucleotide encodes a derivative of the phytase specifically described herein; and a polynucleotide which encodes a phytase that comprises an amino acid segment which differs from one of the sequences in FIGS. 12, 14 or 20, provided that the polynucleotide hybridizes under medium to high stringency conditions with a nucleotide sequence as shown in FIG. 21.

Additionally, the present invention encompasses vectors which include the polynucleotide sequences described above, host cells which have been transformed with such polynucleotides or vectors, fermentation broths comprising such host cells and phytase proteins encoded by such polynucleotides which are expressed by the host cells. Preferably, the polynucleotide of the invention is in purified or isolated form and is used to prepare a transformed host cell capable of producing the encoded protein product thereof. Additionally, polypeptides which are the expression product of the polynucleotide sequences described above are within the scope of the present invention.

According to one embodiment, the polynucleotide encodes a phytate-hydrolyzing enzyme including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIGS. 12, 14 or 20.

Another aspect of the present invention provides an isolated polynucleotide encoding an enzyme having phytase activity, wherein the enzyme is derived from a *Eschrichia* spp. source. The source can be, for example, *Eschrichia coli*.

In another embodiment, the polynucleotide encoding a phytate-hydrolyzing enzyme has at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 21, or (ii) is capable of hybridizing to a probe derived from one of the nucleotide sequences disclosed in FIG. 21 under conditions of medium to high stringency, or (iii) is complementary to one of the nucleotide sequences disclosed in FIG. 21.

Yet a further aspect of the present invention provides an expression construct including a polynucleotide sequence (i) having at least 55% identity, preferably at least 60% identity, s more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 21, or (ii) being capable of hybridizing to a probe derived from the nucleotide sequence disclosed in FIG. 21 under conditions of medium to high stringency, or (iii) being complementary to the nucleotide sequence disclosed in FIG. 21. Also provided are a vector (e.g., a plasmid) including such expression construct, and a host cell (such as an *Bacillus*, e.g., *Bacillus subtilus*) transformed with such a vector.

In another of its aspects, the present invention provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in Figure \*, or (ii) being capable of hybridizing to a polynucleotide including a sequence as disclosed in Figure \* under conditions of medium to high stringency, or (iii) being complementary to one of the nucleotide sequences disclosed in FIG. 21.

In one embodiment, the microbial source is a bacterial source, e.g., a *Escherichia* species, such as *Escherichia coli*.

The present invention additionally provides a food or animal feed including an enzyme having phytase activity, wherein the enzyme comprises an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIGS. 12, 14 or 20 and the enzyme is derived from a bacterial source such as *Escherichia coli*.

Another aspect of the present invention provides a method of producing an enzyme having phytase activity, comprising:

(a) providing a host cell transformed with an expression vector comprising a polynucleotide encoding a phytase enzyme comprising at least one modification of at least one amino acid residue as described herein;
(b) cultivating the transformed host cell under conditions suitable for the host cell to produce the phytase; and
(c) recovering the phytase.

In one embodiment, the host cell is a plant cell. In this embodiment, cells or entire transformed plants may be grown and used.

Another aspect of the present invention provides a method of producing an enzyme having phytase activity, comprising:
(a) providing a host cell transformed with an expression vector comprising a polynucleotide encoding a phyatse enzyme comprising at least one modification of at least one amino acid residue as described herein;
(b) cultivating the transformed host cell under conditions suitable for the host cell to produce the phytase. The transformed cells, as well as organisms grown from such cells, may be used without further isolation of the enzyme.

In another aspect, the invention provides a purified enzyme having phytase activity, produced by the methods described above.

In yet another of its aspects, the present invention provides a method of separating phosphorous from phytate, comprising the step of treating the phytate with an enzyme comprising an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in FIGS. 12, 14, or 20.

The present invention further provides a method of separating phosphorous from phytate, comprising the step of treating the phytate with an enzyme as defined above.

The present invention further provides a vector (e.g., plasmid) including such an expression construct, as well as a host cell (e.g., *Bacillus subtilis*) transformed with a vector as described above.

The present invention additionally provides a probe for use in detecting nucleic acid sequences coding for an enzyme having phytase activity derived from a microbial source, comprising: a nucleotide sequence (i) having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to a nucleotide sequence as disclosed in FIG. 21, or (ii) being capable of hybridizing to a polynucleotide including a sequence as disclosed in FIG. 21 under conditions of medium to high stringency, or (iii) being complementary to the nucleotide sequence disclosed in FIG. 21.

Still further, the present invention provides a method of separating phosphorous from is phytate, comprising the step of treating the phytate with an enzyme (i) having phytate hydrolyzing activity and (ii) including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in Figure *. In another aspect, the invention provides a method of separating phosphorous from phytate, comprising the step of treating the phytate with an enzyme (i) having phytate hydrolyzing activity and (ii) including an amino acid sequence having at least 55% identity, preferably at least 60% identity, more preferably at least 65% identity, still more preferably at least 70% identity, yet more preferably at least 75% identity, even more preferably at least 80% identity, again more preferably at least 85% identity, yet again more preferably at least 90% identity, and most preferably at least 95% up to about 100% identity to an amino acid sequence as disclosed in Figure *, or as disclosed in Figure *.

In another aspect of the invention, provided herein is a recombinant AppA phytase comprising a signal sequence operable in a *Bacillus* species and the sequence of a mature phytase comprising a modification of at least one amino acid sequence position. In a preferred embodiment, the signal sequence has the amino acid sequence of amino acids 1-30 of the sequence designated EBC18B2 of FIG. 12 or FIG. 14. In a preferred embodiment, the recombinant AppA phytase comprises the amino acid sequence of the sequence designated PHY679, PHY735, PHY736, PHY846 or PHY902 of FIG. 12.

In yet another aspect of the invention, a recombinant AppA phytase is provided comprising a modification of the secretion signal of amino acids 1-30 of the sequence designated s EBC18B2 of FIG. 12 or FIG. 14 and the sequence of a mature AppA phytase or of a natural variant or of a mutant thereof. In a preferred embodiment, the modification is of residue 11, preferably a substitution. In a preferred embodiment, the substitution is leucine for serine. In a preferred embodiment, the AppA phytase comprises the amino acid sequence of the sequence designated PHY850 in FIG. 12 or PHY850, PHY1361 or PHY1363 of FIG. 14.

Also provided herein is a nucleic acid comprising a sequence encoding an AppA phytase described above, as well as an expression construct comprising such a sequence. In addition, a vector comprising the expression construct and a host cell transformed with the expression construct are provided. In a preferred embodiment, the host cell is a *Bacillus* species, preferably *Bacillus subtilis*.

In a different aspect of the invention, provided herein are methods of producing an enzyme having phytase activity. In a preferred embodiment, the method comprises providing a host cell transformed with an expression construct described above and culturing the host cell under conditions suitable for the cell to produce the phytase. In one embodiment, the method further comprises recovering the phytase. Preferably, the host cell is a *Bacillus* species, preferably *Bacillus subtilis*.

Also provided herein are methods of producing a heterologous polypeptide having phytase activity in a *Bacillus* species, preferably *Bacillus subtilis*. In a preferred embodiment, the method comprises a providing a host *Bacillus* with an expression vector comprising a polynucleotide encoding a *Bacillus* signal sequence linked to a polynucleotide encoding a mature AppA phytase or mutant thereof, thereby encoding a chimeric polypeptide, and cultivating said host *Bacillus* under conditions suitable for said *Bacillus* to produce said chimeric polypeptide. In a preferred embodiment, the signal sequence is a composite signal sequence. In a preferred embodiment, the AppA phytase is derived from *E. coli*. In a preferred embodiment, the expression vector comprises a sequence encoding the sequence designated EBC18B2, PHY679, PHY735, PHY736, PHY846, HY850 or PHY902 of FIG. 12 or EBC18B2, PHY850, Phy1361 or PHY1363 of FIG. 14. Also provided are polypeptides having phytase activity produced by this method.

Further provided herein are methods of separating phosphorous from phytate comprising treating the phytate with an AppA phytase described above. In addition, food or animal feed comprising an AppA phytase described above is provided

V. Expression and Recovery of Phytate Hydrolyzing Enzymes

The polynucleotide sequences of the present invention may be expressed by operatively linking them to an expression control sequence in an appropriate expression vector and employed in that expression vector to transform an appropriate host according to techniques well established in the art. The polypeptides produced upon expression of the nucleic acid sequences of this invention can be isolated from the fermentation of cell cultures and substantially purified in a variety of ways according to well established techniques in the art. One of skill in the art is capable of selecting the most appropriate isolation and purification techniques.

More particularly, the present invention provides host cells, expression methods and systems for the production of phytate hydrolyzing enzymes derived from microorganisms, such as *Eschericia* species, and derivatives thereof. Once a nucleic acid sequence encoding a phytate hydrolyzing enzyme of the present invention is obtained, recombinant host cells containing the nucleic acid sequence may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989) and Sambrook et al., Molecular Cloning, A Laboratory Manual, 3d Ed., Cold Spring Harbor Laboratory Press, Cold Spring Harbor, N.Y. (2001).

In one embodiment, nucleic acid sequences encoding phytate hydrolyzing enzymes derived from *E. coli* strains and having at least 60%, at least 70%, at least 80%, at least 85%, at least 90%, at least 95%, 96%, 97%, 98% and at least 99% identity to any one of the nucleic acid sequences of FIG. 21 or a functional derivative thereof, or which is capable of hybridizing under conditions of intermediate to high stringency to any one of the nucleic acid sequences of FIG. 21, or which is complementary to any one of the nucleic acid sequences of FIG. 21 are obtained and transformed into a host cell using appropriate vectors.

The nucleic acid sequences encoding phytate hydrolyzing enzymes can include a leader sequence capable of providing for the secretion of the encoded phytase. Depending on whether the phytase is to be expressed intracellularly or is secreted, a DNA sequence or expression vector of the invention can be engineered such that the mature form of the phytase is expressed with or without a natural phytase signal sequence or a signal sequence which functions in a bacteria (e.g., *Bacillus subtilis*), other prokaryotes, or eukaryotes. Expression can also be achieved by either removing or partially removing said signal sequence.

A variety of vectors and transformation and expression cassettes suitable for the cloning, transformation and expression in bacteria, fungus, yeast, insect and plant cells are known by those of skill in the art. Typically, the vector or cassette contains sequences directing transcription and translation of the nucleic acid sequence, a selectable marker, and sequences allowing autonomous replication or chromosomal integration. Suitable vectors comprise a region 5' to the gene which harbors transcriptional initiation controls and a region 3' to the DNA fragment which controls transcriptional termination. These control regions may be derived from genes homologous or heterologous to the host, or may be derivatives of naturally occurring sequences, as long as the control region selected is able to function in the host cell.

Initiation control regions or promoters which are useful to drive expression of the phytate hydrolyzing enzymes in a host cell are known to those skilled in the art. A nucleic acid sequence encoding the phytate hydrolyzing enzyme is linked operably through initiation codons to selected expression control regions for effective expression of such enzyme. Once suitable cassettes are constructed, they are used to transform the host cell.

In cases where plant expression vectors are used, the expression of a sequence encoding phytase may be driven by any of a number of promoters. For example, viral promoters such as the 35S and 19S promoters of CaMV (Brisson et al (1984) Nature 310:511-514) maybe used alone or in combination with the omega leader sequence from TMV (Takamatsu et al (1987) EMBO J 6:307-311). Alternatively, plant promoters such as the small subunit of RUBISCO (Coruzzi et al (1984) EMBO J 3:1671-1680; Broglie et al (1984) Science 224:838-843); or heat shock promoters (Winter J and Sinibaldi RM (1991) Results Probl Cell Differ 17:85-105) may be used. These constructs can be introduced into plant cells by direct DNA transformation or pathogen-mediated transfection. For reviews of such techniques, see Hobbs S or Murry LE (1992) in McGraw Hill Yearbook of Science and Technology, McGraw Hill, New York, N.Y., pp 191-196; or Weissbach and Weissbach (1988) Methods for Plant Molecular Biology, Academic Press, New York, N.Y., pp 421-463.

General transformation procedures are taught in Current Protocols In Molecular Biology (3rd edition, edited by Ausubel et al., 1995, Chapter 9) and Molecular Cloning, A Laboratory Manual (3d Ed., Sambrook et al., 2001, Chapter 1) and include calcium phosphate methods, transformation using PEG and electroporation. Transformation of bacteria is routine in the art (see, e.g., Inoue et al., Gene 96:23-28 (1990)), and some bacteria, such as *Bacillus* spp., *Streptococcus* spp. and *Haemphilus* spp., have a natural ability to take up DNA and incorporate it as part of the host genome. For filamentous, PEG and Calcium mediated protoplast transformation can be used (Finkelstein, DB 1992 Transformation. In Biotechnology of Filamentous Fungi. Technology and Products (eds by Finkelstein & Bill) 113-156. Electroporation of protoplast is disclosed in Finkelestein, DB 1992 Transformation. In Biotechnology of Filamentous Fungi. Technology and Products (eds by Finkelstein & Bill) 113-156. Microprojection bombardment on conidia is described in Fungaro et al. (1995) Transformation of *Aspergillus nidulans* by microprojection bombardment on intact conidia, FEMS Microbiology Letters 125 293-298. *Agrobacterium* mediated transformation is disclosed in Groot et al. (1998) *Agrobacterium tumefaciens*-mediated transformation of filamentous fungi, Nature Biotechnology 16 839-842. For transformation of *Saccharomyces*, lithium acetate mediated transformation and PEG and calcium mediated protoplast transformation as well as electroporation techniques are known by those of skill in the art.

Host cells which contain the coding sequence for a phytate hydrolyzing enzyme of the present invention and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid sequence or protein. Examples of specific assays are provided herein.

It should also be noted that the invention contemplates in vitro expression of the phytase enzymes described herein.

In preferred embodiments of the invention, phytase is produced in bacterial cells. In one embodiment of the present invention, a polynucleotide sequence encoding a phytate hydrolyzing enzyme derived from *E. coli* (deposit no. ATCC ***25404; 29947?***), or a derivative thereof, is isolated and expressed in *Bacillus subtilis*. In this embodiment, the phytase may be expressed under conditions in which it might not otherwise be expressed, or the phytase will be overexpressed under conditions that the indigenous phytase is expressed. The expressed phytase can then be recovered, e.g., as described below.

In preferred embodiments of the invention, the phytase is expressed in plants. "Transgenic plant", as used herein, refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant and parts of said plant, for instance grains, seeds, flowers, leaves, roots, fruit, pollen, stems, etc.

The present invention is applicable to both dicotyledonous plants (e.g. tomato, potato, soybean, cotton, tobacco, etc.) and monocotyledonous plants, including, but not limited to graminaceous monocots such as wheat (*Triticum* spp.), rice (*Oryza* spp.), barley (*Hordeum* spp.), oat (*Avena* spp.), rye (*Secale* spp.), corn (*Zea mays*), sorghum (*Sorghum* spp.) and millet (*Pennisetum* spp). For example, the present invention can be employed with barley genotypes including, but not limited to Morex, Harrington, Crystal, Stander, Moravian III, Galena, Salome, Steptoe, Klages, Baronesse, and with wheat genotypes including, but not limited to Yecora Rojo, Bobwhite, Karl and Anza. In general, the invention is particularly useful in cereals.

Standard molecular biology methods and plant transformation techniques can be used to produce transgenic plants that produce seeds containing phytase protein. The following description provides general guidance as to the selection of particular constructs and transformation procedures.

The present invention utilizes recombinant constructs that are suitable for obtaining expression of phytase in plant seeds relative to non-transformed plant seeds. In their most basic form, these constructs may be represented as Pr-Ph, wherein Pr is a seed-specific promoter and Ph is a nucleic acid sequence encoding phytase. In another embodiment, a peptide signal sequence that targets expression of the phytase polypeptide to an intracellular body may be employed. Such constructs may be represented as Pr-SS-Ph, wherein SS is the signal peptide. Nucleic acid molecules that may be used as the source of each of these components are described in the Definitions section above.

Each component is operably linked to the next. For example, where the construct comprises the hordein D-promoter (P), the hordein D-signal sequence (SS) encoding the hordein signal peptide, and an open reading frame encoding a phytase (Ph), the hordein promoter is linked to the 5' end of the sequence encoding the hordein signal sequence, and the hordein signal sequence is operably linked to the 5' end of the phytase open reading frame, such that C terminus of the signal peptide is joined to the N-terminus of the encoded protein.

The construct will also typically include a transcriptional termination region following the 3' end of the encoded protein ORF. Illustrative transcriptional termination regions include the nos terminator from *Agrobacterium* Ti plasmid and the rice alpha-amylase terminator.

Standard molecular biology methods, such as the polymerase chain reaction, restriction enzyme digestion, and/or ligation may be employed to produce these constructs comprising any nucleic acid molecule or sequence encoding a phytase protein or polypeptide.

Introduction of the selected construct into plants is typically achieved using standard transformation techniques. The basic approach is to: (a) clone the construct into a transformation vector; which (b) is then introduced into plant cells by one of a number of techniques (e.g., electroporation, microparticle bombardment, *Agrobacterium* infection); (c) identify the transformed plant cells; (d) regenerate whole plants from the identified plant cells, and (d) select progeny plants containing the introduced construct. Preferably all or part of the transformation vector will stably integrate into the genome of the plant cell. That part of the transformation vector which integrates into the plant cell and which contains the introduced Pr-Ph or Pr-SS-Ph sequence (the introduced "phytase transgene") may be referred to as the recombinant expression cassette.

Selection of progeny plants containing the introduced transgene may be made based upon the detection of phytase expression in seeds, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include:

U.S. Pat. No. 5,571,706 ("Plant Virus Resistance Gene and Methods");
U.S. Pat. No. 5,677,175 ("Plant Pathogen Induced Proteins");
U.S. Pat. No. 5,510,471 ("Chimeric Gene for the Transformation of Plants");
U.S. Pat. No. 5,750,386 ("Pathogen-Resistant Transgenic Plants");
U.S. Pat. No. 5,597,945 ("Plants Genetically Enhanced for Disease Resistance");
U.S. Pat. No. 5,589,615 ("Process for the Production of Transgenic Plants with Increased Nutritional Value Via the Expression of Modified 2S Storage Albumins");
U.S. Pat. No. 5,750,871 ("Transformation and Foreign Gene Expression in *Brassica* Species");
U.S. Pat. No. 5,268,526 ("Over expression of Phytochrome in Transgenic Plants");
U.S. Pat. No. 5,780,708 ("Fertile Transgenic Corn Plants");
U.S. Pat. No. 5,538,880 ("Method For Preparing Fertile Transgenic Corn Plants");
U.S. Pat. No. 5,773,269 ("Fertile Transgenic Oat Plants");
U.S. Pat. No. 5,736,369 ("Method For Producing Transgenic Cereal Plants");
U.S. Pat. No. 5,610,049 ("Methods For Stable Transformation of Wheat").

These examples (which are incorporated herein in their entirety) include descriptions of transformation vector selection, transformation techniques and the construction of constructs designed to express an introduced transgene.

The transgene-expressing constructs of the present invention may be usefully expressed in a wide range of higher plants to obtain seed- or grain-specific expression of selected polypeptides. The invention is expected to be particularly applicable to monocotyledonous cereal plants including barley, wheat, rice, rye, maize, triticale, millet, sorghum, oat, forage, and turf grasses. In particular, the transformation methods described herein will enable the invention to be used with genotypes of barley including Morex, Harrington, Crystal, Stander, Moravian III, Galena, Golden Promise, Steptoe, Klages and Baronesse, and commercially important wheat genotypes including Yecora Rojo, Bobwhite, Karl and Anza.

The invention may also be applied to dicotyledenous plants, including, but not limited to, soybean, sugar beet, cotton, beans, rape/canola, alfalfa, flax, sunflower, safflower, brassica, cotton, flax, peanut, clover, vegetables such as lettuce, tomato, cucurbits, cassava, potato, carrot, radish, pea, lentils, cabbage, cauliflower, broccoli, Brussels sprouts, peppers; and tree fruits such as citrus, apples, pears, peaches, apricots, and walnuts.

A number of recombinant vectors suitable for stable transformation of plant cells or for the establishment of transgenic plants have been described including those described in Weissbach and Weissbach, (1988), and Gelvin et al., J. Bacteriol. 172(3):1600-1608 (1990). Typically, plant transformation vectors include one or more ORFs under the transcriptional control of 5' and 3' regulatory sequences and a dominant selectable marker with 5' and 3' regulatory sequences. The selection of suitable 5' and 3' regulatory sequences for constructs of the present invention is discussed above. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Methods for the transformation and regeneration of both monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium* mediated transformation. Typical procedures for transforming and regenerating plants are described in the patent documents listed at the beginning of this section.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown to maturity to allow seed set, the seeds can be harvested and assayed for expression of phytase.

The phytase of the invention can be recovered from culture medium or from host cell lysates. If membrane-bound, it can be released from the membrane using a suitable detergent solution (e.g. Triton-X 100) or by enzymatic cleavage. Cells employed in expression of phytase can be disrupted by various physical or chemical means, such as freeze-thaw cycling, sonication, mechanical disruption, or cell lysing agents. It may be desired to purify the phytase from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants; and metal chelating columns to bind epitope-tagged forms of the phytase. Various methods of protein purification may be employed and such methods are known in the art and described for example in Deutscher, *Methods in Enzymology*, 182 (1990); Scopes, *Protein Purification: Principles and Practice*. Springer-Verlag, New York (1982). The purification step(s) selected will depend, for example, on the nature of the production process used and the particular form of phytase produced.

In a preferred embodiment, the phytase(s) is/are produced in transgenic non-human animals. Methods of producing such transgenic animals are described, for example, in U.S. Pat. No. 6,291,740. Methods for the successful production of transgenic bovine (e.g., U.S. Pat. Nos. 6,080,912 and 6,066,725), swine (e.g., U.S. Pat. Nos. 6,271,436 and 5,942,435), goats (e.g., U.S. Pat. No. 5,907,080) and fish (e.g., U.S. Pat. No. 5,998,697) are available in the art. Furthermore, organ-specific expression, particularly expression in milk produced by the transgenic animals, is within the skill of the ordinary artisan (e.g., e.g., U.S. Pat. Nos. 6,268,545 and 6,262,336). The disclosure of each of these patents is incorporated herein in its entirety.

VI. Assaying for Phytase Activity

Assays for phytase activity are well known in the art. Perhaps the most widely used is the classic assay for liberation of inorganic phosphate developed by Fiske and SubbaRow, *Journal of Biological Chemistry* 66:375-392 (1925). A variation of this method is found in Mitchell et al., *Microbiol.* 143:245-252 (1997). A preferred method is described in *Food Chemicals Codex,* 4th Edition, Committee on Food Chemicals Codex, Institute of Medicine, National Academy Press, Washington, D.C., 1996 at pages 809-810. Each of these references are incorporated herein. Specific examples of such assays are described herein.

Generally, the assay involves allowing a measured weight or volume of a phytase sample to react with phytate in solution for a measured period of time. The reaction is stopped and a color solution containing ammonium molybdate (AM) is added to the reaction solution. Colorimetry is then performed using a spectrophotometer and compared to controls of known concentration of inorganic phosphate ($P_i$) and/or controls produced by reactions with enzymes having known phytase activity. A Unit of activity is determined as the amount of enzyme sample required to liberate 1 µmol $P_i$ per minute from phytate under defined reaction conditions.

Enzyme reactions are frequently run at pH 5.5 and 37° C. However, pH and temperature conditions may be varied to determine optimum reaction conditions and tolerances for a given phytase. When different reaction conditions are tested, Units of activity should still be related to a single specific set of reaction conditions.

The reaction may be stopped and then the color solution added, or a stop/color solution may be used that both arrests the enzyme activity and adds a product whose spectral absorbance is measurably affected by the concentration of $P_i$ in a predictable and calculatable manner. As discussed above, the color solutions generally contain AM. Various examples of such solutions are available in the relevant literature. In U.S. Pat. No. 6,039,942, the reaction is stopped using trichloroactetate (TCA) and the color solution added thereafter contained ferrous sulfate and AM. In other examples wherein the reaction was first stopped with TCA, different color solution contained sulfuric acid, AM and ascorbic acid (U.S. Pat. No. 6,221,644) and sulfuric acid, AM and ferrous sulfate (U.S. Pat. No. 6,190,897). In other cases, the color and stop solution are the same. For example, in both U.S. Pat. Nos. 6,139,902 and 6,261,592, the solution contained sulfuric acid, AM and acetone, after which a solution containing acetic acid was added. In a preferred embodiment, the color/stop s solution contains ammonium vanadate, AM and nitric acid (see *Food Chemicals Codex*, above).

Wavelength-specific absorption by the final solution, containing the reaction solution and stop/color solution(s), is measured using a spectrophotometer. Many such instruments are available and their use is routine in the art. The wavelength used for absorption measurement can vary with the components of the color solution. For example, the references cited above measured absorbance at 380, 415, 690, 700 or 750 nm. Any of these may provide adequate indication of $P_i$ concentration in these solutions. However, the wavelength used should generally be the one described in a given protocol. The skilled artisan can easily determine empirically which wavelength provides optimum discrimination of differences in $P_i$ concentration by comparing the linearity of absorption change between serially diluted control solutions of known $P_i$ concentration at different wavelengths.

VII. Applications of Phytate Hydrolyzing Enzymes

The phytase and derivatives thereof as taught herein can be used in a variety of applications where it is desirable to separate phosphorous from phytate. Several exemplary applications are set forth below.

For example, the invention provides for the use of cells or spores capable of producing phytase according to the invention as a probiotic or direct fed microbial product. Preferred embodiments for said uses are phytase-producing *Bacillus* spp. of the invention.

In addition, the invention contemplates the use of phytase as described herein in food or animal feed.

The present invention provides food or animal feed including phytase as described herein. Preferably, said food or animal feed comprises phytase as an additive which is active in the digestive tract, preferably the crop and/or small intestine, of livestock, such as poultry and swine, and aquatic farm animals including fish and shrimp. Said additive is also preferably active in food or feed processing.

In an alternative embodiment, phytase or phytase producing organisms are added as a pretreatment to food or animal feed, such as in the processing of the food or feed. In this embodiment, the phytase is active prior to consumption of the food or feed, but may or may not be active at the time the food or animal feed is consumed.

Compositions comprising polypeptides or proteins possessing phytase activity may be prepared in accordance with methods known in the art and may be in the form of a liquid or a dry composition. The polypeptide to be included in the composition may be stabilized in accordance with methods known in the art.

The invention additionally provides food or animal feed comprising cells, spores or plant parts, including seeds, capable of expressing phytase as described herein.

Still further, the present invention contemplates a method for the production of a food or animal feed, characterized in that phytase according to the invention is mixed with said food or animal feed. Said phytase is added as a dry product before processing or as a liquid before or after processing.

According to one embodiment, wherein a dry powder is used, the enzyme is diluted as a liquid onto a dry carrier such as milled grain.

Liquid compositions need not contain anything more than the phytase enzyme, which may be in either a substantially purified or unpurified form, preferably in a substantially purified form. Usually, however, a stabilizer such as glycerol, sorbitol or mono propylene glycol is also added. The liquid composition may also comprise one or more other additives, such as salts, sugars, preservatives, pH-adjusting agents (i.e., buffering agents), proteins, or phytate (a phytase substrate). Typical liquid composition are aqueous or oil-based slurries. The liquid compositions can be added to a food or feed after an optional pelleting thereof.

Dry compositions may be spray-dried compositions, in which case the composition need not contain anything more than the enzyme in a dry form. Usually, however, dry compositions are so-called granulates which may readily be mixed with for example food or feed components, or more preferably, form a component of a pre-mix. The particle size of the enzyme granulates preferably is compatible with that of the other components of the mixture. This provides a safe and convenient means of incorporating enzymes into for example an animal feed.

Agglomeration granules are prepared using agglomeration techniques in a high shear mixer (e.g., Lodige) during which a filler material and the enzyme are co-agglomerated to form granules. Absorption granulates are prepared by having cores of a carrier material to adsorb/be coated by the enzyme.

Typical filler materials are salts such as disodium sulphate. Other fillers are kaolin, talc, magnesium aluminum silicate and cellulose fibers. Optionally, binders such as dextrins are also included in agglomeration granules.

Typical carrier materials are starch, e.g., in the form of cassava, corn, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as coloring agents, aroma compounds, stabilizers, vitamins, minerals other feed or food enhancing enzymes and the like. This is so in particular for the so-called pre-mixes.

A "feed" and a "food," respectively, means any natural or artificial diet, meal or the like or components of such meals intended or suitable for being eaten, taken in, digested, by an animal and a human being, respectively.

A "food or feed additive" is an essentially pure compound or a multi component composition intended for or suitable for being added to food or feed. It usually comprises one or more compounds such as vitamins, minerals or feed enhancing enzymes and suitable carriers and/or excipients, and it is usually provided in a form that is suitable for being added to animal feed.

The phytases of the invention can also be used in poultry food to improve egg shell quality (reduction of losses due to breaking), see for example, The Merck Veterinary Manual (Seventh Edition, Merck & Co., Inc., Rahway, N.J., USA, 1991, page 1268); Jeroch et al. Bodenkultur Vo. 45(4):361-368 (1994); Poultry Science, 75(l):62-68 (1996); Canadian Journal of Animal Science 75(3):439-444 (1995); Poultry Science 74(5):784-787 (1995) and Poultry Science 73(10):1590-1596 (1994).

An effective amount of the polypeptide in food or feed is typically from about 10 to 50,000 U/kg feed or food; preferably from about 10 to 15,000, more preferably from about 10 to 10,000, in particular from about 100 to 5,000, especially from about 100 to about 2,000 U/kg feed or food.

The present invention also provides a method for the production of a food or animal feed, characterized in that cells, plant parts, including seeds, and/or spores capable of expressing phytase according to the invention are added to said food or animal feed. Such cells or spores, may be of any origin, bacterial, plant, or animal.

Further, the present invention provides for the use of the phytase described herein with or without accessory phosphatases in the production of inositol and inorganic phosphate, and phytate intermediates.

Also provided is a method for the reduction of levels of phosphorous in animal manure, characterized in that an animal is fed an animal feed according to the invention in an amount effective in converting phytate contained in said animal feed.

In one embodiment, the transgene protein, for example phytase expressed in plants, especially seeds or grains, using the methods described herein, is used in the production and synthesis of phytase. The phytase transgene expressed by the recombinant nucleic acid of the invention may be harvested at any point after expression of the protein has commenced. When harvesting from the seed or grain or other part of a plant for example, it is not necessary for the seed or grain or other part of the plant to have undergone maturation prior to harvesting. For example, transgene expression may occur prior to seed or grain maturation or may reach optimal levels prior to seed or grain maturation. The transgene protein may be isolated from the seeds or grain, if desired, by conventional protein purification methods. For example, the seed or grain can be milled, then extracted with an aqueous or organic extraction medium, followed by purification of the extracted phytase protein. Alternatively, depending on the nature of the intended use, the transgene protein may be partially purified, or the seed or grain may be used directly without purification of the transgene protein for food or animal feed, food processing or other purposes.

Alpha-amylases break down starch 1-4 linkages. Amylases are enzymes fundamental to the brewing and baking industries. Amylases are required to break down starch in malting and in certain baking procedures carried out in the absence of added sugars or other carbohydrates. Obtaining adequate activity of these enzymes is problematic especially in the malting industry. It has been known for some time that phytate has an inhibitory effect on amylases. A method of adequately increasing the activity of amylases with a physiologically acceptable system, leads to more rapid malting methods and, owing to increased sugar availability, to alcoholic beverages such as beers with reduced carbohydrate content.

Accordingly, seeds or grains with phytase expression provide advantages in the production of malt and beverages produced by a fermentation process. Enhanced activity of amylases in grain increases the speed and efficiency of germination, important in malting, where malt is produced having increased enzymatic activity resulting in enhanced hydrolysis of starch to fermentable carbohydrates, thereby, improving the efficiency of fermentation in the production of alcoholic beverages, for example, beer and scotch whiskey. Enhanced fermentation processes also find use in the production of alcohols that are not intended for human consumption, i.e., industrial alcohols.

The phytase and phytate-derived intermediates of the invention also find use in many other agricultural, industrial, medical and nutritional applications. For example phytase and phytate-derived intermediates can be used in grain wet milling. Phytate is used in cleaning products, rust removal products and in the removal of metals and other polycations from such diverse materials as waste products and carbonated beverages. Phytate and phytases may be used in the isolation and recovery of rare metals. Phytases may be used to produce lower phosphate homologs of phytate, which may be used in dentifrice and other dental care products as well as potential treatments or preventatives of bone resorption (e.g., in osteoporosis) and renal calculi (kidney stones). Phytate and derivatives have found use in the production of tofu, and chelation of minerals (e.g., iron, zinc, calcium or magnesium) with phytate, followed by release with addition of phytase may provide a unique means of providing these nutrients. Phytases may be used in the production of inositol from phytate its use in food products. Phytases may also be used in the chemical and biochemical synthesis of phosphate containing materials. Phytases, phytate and lower phosphate phytate derivatives find many other uses in personal care products, medical products and food and nutritional products, as well as various industrial applications, particularly in the cleaning, textile, lithographic and chemical arts.

The following examples are offered for illustrative purposes only, and are not intended to limit the scope of the present invention in any way. The skilled artisan will appreciate that 2s the methods disclosed may be applied to any number of different species, including to obtain all sequences disclosed herein. All patent and literature references cited in the present specification are hereby incorporated by reference in their entirety.

EXAMPLES

Example 1

Preparation of Genomic DNA Encoding Phytases

Genomic DNA is prepared from various microbial sources for the purpose of undertaking a PCR reaction to determine the sequences of natural variants of the *E. coli* AppA encoding phytase enzyme, including sequences 3' and 5' to the transcribed region, as well as sequences of any introns.

PCR templates were prepared from either genomic DNA (*E. coli* K-12), from single colonies of various enteric strains listed in Table II (strains courtesy of Texas A&M, Dept. of Biology), and from the biomass of phytate culture enrichments (zoo comost and soil). Genomic DNA is obtained and isolated according to standard methods. As the skilled artisan will recognize, probes for genomic nucleic acid sequences are readily obtained from any of the *E. coli* phytase cDNA sequences disclosed in FIG. 21. Such probes may be used, following the PCR methods described below, to obtain genomic sequences.

The following is an alternate method for obtaining genomic phytase sequences.

Alignments were performed for several known phytase sequences, including those from *Shigella flexnarii, Shigella sonnei, Pasturella aerogenes, Entrobacter cloacae, Entrobacter agglomerans*, and *Proteus vulgaris*.

The following DNA primers have been constructed for use in amplification of phytase genes from the libraries constructed from the various microorganisms.

```
AppA3F    5'-atgaaagcgatcttaat         (SEQ ID No. 12)

AppA5F    5'-cgtcatggtgtgcgtgctcc      (SEQ ID No. 13)
```

-continued
```
AppA6F    5'-cgccagaggttgcccg         (SEQ ID No. 14)

AppA7R    5'-gcggctggcaacctctgg       (SEQ ID No. 15)

AppA4R    5'-ttacaaactgcacgccggta-    (SEQ ID No. 16)
             tgcgtgcgtgcttcatt
```

Primer combinations included:
AppA 3F+4R=1.3 kb product
AppA 3F+7R=0.86 kb product
AppA 5F+4R=1.19 kb product
AppA 6F+4R=0.44 kb product
AppA 5F+7R=0.75 kb product PCR is performed on a standard PCR machine such as the PTC-150 Mini Cycler from MJ Research Inc. (Watertown, Mass.) or an Eppendorf Mastercycler (Hamburg, Germany). In the experiments described below, PCR was performed using a Hybaid Touchdown thermocycler (Middlesex, UK).

Two approaches were developed for amplification of phytase genes from the genomic DNA:

A) A first PCR is run using BOXb 1 and BOX6 primers; the products are run on an agarose gel and approximately 1 kb fragments are isolated and run in a second PCR using nested primers. For the second PCR run, best results were obtained using primers from BOX1-BOX5 or from BOX5-BOX6 or BOX2.5/BOX4'.

Protocol A:
PCR1:-2' at 94° C. (1 cycle)
  45" at 94° C.; 1'30" at 40° C.; 1'30" at 72° C. (30 cycles)
  7' at 72° C. (1 cycle)
  hold at 4° C.

Fragments were put on a 1% low melting gel and fragments around the expected size (0.0-1.2 kb) were sliced from the gel, isolated and used as a template for the second PCR run (PCR2). PCR 2 followed the same cycling protocol as PCR1.

B) Touchdown PCR was performed using BOX2.5/BOX4' primers. Using this technique, a specific fragment could be isolated, cloned into a TOPO vector (Invitrogen Corp., Carlsbad, Calif.), and sequenced without further processing.

Protocol B:
  3' at 95° C. (1 cycle)
    1' at 95° C.; 1' at 60° C., decreasing to 50° C.; 30" at 72° C. (20 cycles, so that the temperature dropped 0.5° C. each cycle in the annealing step)
  1' at 95° C.; 1' at 50° C.; 30" at 72°C. (10 cycles)
  hold at 4° C.

From the sequenced fragments, it was possible to use the RAGE technique (rapid amplification of genomic ends) to rapidly obtain the sequence of the full length gene. Using the GenomeWalker™ Kit from Clontech Laboratories, Inc (Palo Alto, Calif.) and manufacturer's protocol (GenomeWalker™ Kits User Manual, published Nov. 10, 1999, expressly incorporated herein), adapter ligations were derived from the fragment sequences to further determine upstream gene sequence. Sequences of phytase genes were determined from chromosomal DNA of various species.

Example 2

Sequence Analysis of AppA Variants

A PCR survey of the various enteric strains (including *E. coli* K-12 as a control) resulted in the isolation of three complete and four partial AppA gene fragments. Strains *E. coli* K-12, *Shigella flexnarii* and *Shigella sonnei* all yeilded PCR products whose size was consistent with a full-length AppA gene. Strains *Pasturella aerogenes, Entrobacter cloacae*,

*Entrobacter agglomerans*, and *Proteus vulgaris* yielded only truncated AppA fragments. Sequence analysis of these cloned products revealed significant homology to the *E. coli* AppA gene. The predicted amino acid sequences of the *S. sonnei* and *S. flexnarii* variants differed from the published *E. coli* sequence at one and six amino acid positions, respectively, resulting from single base pair changes. Furthermore, the *S. flexnarii* gene s contained eight silent nucleotide changes (A267G, G285A, C297T, C477T, G756A, A882G, G957A and C966T) while *S. sonnei* gene contained no silent change.

The partial enteric AppA gene sequences contained as few as no amino acid changes (*P. aerogenes*) and as many as three amino acid changes (*E. cloacae*). The *E. cloacae* and *E. agglomerans* AppA s were highly similar and differed at only two amino acid positions. The biomass that resulted from liquid culture phytate enrichment of zoo compost was used to prepare genomic DNA for PCR amplification. The amplified product was cloned directly into a T/A cloning vector and transformants were analyzed for the presence of AppA-related sequences. Like some of the enteric strains, only a partial AppA gene sequence was recovered. The gene fragment recovered from the compost enrichment contained 2 amino acid changes when compared to the *E. coli* AppA sequence.

Example 3

Evidence of Phytate Hydrolyzing Activity in Liquid Culture

A selected bacterial species is grown in defined media containing various concentrations of inorganic phosphate, and growth characteristics and phytase production are assayed and compared. Suspensions are used to inoculate a minimal media (Vogels) where the phosphate concentration is altered to see how this will affect growth and phytase production. Cultures are grown in 50ml of medium in shake flask culture at 25° C. to 30° C. Cultures are harvested at 24, 48, 72 and 96 hours. Culture supernatants are assayed for phytase activity using the method of Fiske and SubbaRow, Journal of Biological Chemistry 66:375-392 (1925). Growth may be determined by dry weight or OD readings.

3A. Effect of Different Media Conditions on Growth and Morphology

A series of microbial growth curves are produced to look at the effect of available P in the medium on growth and phytase production. In some instances, when the P level is reduced, morphological changes in the growth of the bacteria are observed which are associated with a stressed condition (e.g., bacterial morphology, pelleting, heterogeneous growth and an overall appearance of a pale yellow color). This physiological strain may be related to the appearance of phytase activity at a point in the growth curve, for example approaching late exponential phase. Morphological evidence of phytic acid utilization may be observed in cultures of low P (e.g., 0.57 mM) supplemented after 24 hours growth with 1 mM phytate as a phosphorus source. The morphological changes seen without added phytate may not be AppArent, indeed the supplement samples may resemble cultures in media of higher P which were not limiting. This response would indicate that a phytic acid specific hydrolyzing activity was being produced so that P could be supplied to the growing bacteria. As a caveat, it is possible that higher concentrations of phytate (e.g., 5 mM) supplementing the cultures result in a lack of cell growth. Such a result would suggest that the high level of phytate in the medium chelates essential minerals resulting in a medium that cannot support bacterial growth and nutrition.

In an exemplary study, the microbe is grown in media containing
High phosphate (1.14 mM)
Low phosphate (0.57 mM)
Low phosphate plus 1 mM supplemented phytate.

Growth is monitored over 0, 24, 48, 72 and 96 hours by dry weight measurements, and the morphological characteristics in response to the different media conditions are also observed. In a situation where phytate hydrolyzing activity which allows the to access phosphate from phytate, and so circumvent phosphate starvation stresses that the culture may otherwise experience, the major observations that would be expected are:

1. Good growth in high phosphate, consistent bacterial morphology indicative of healthy culture.
2. Markedly poorer growth in low phosphate condition, bacterial morphology heterogenous with evidence of clumping. The culture may have a sickly yellow appearance.
3. Similar cultures as for (2), when supplemented with phytate (the substrate), no longer appear to be under the same physiological stress. Biomass growth is similar to condition (1) and the bacterial morphology is the same as for the high phosphate condition.
4. Growth curves and photographic evidence support these observations.

3B. Phytase Activity in Culture Supernatants

Phytase activity in the supernatants of bacterial growing on media with variable levels of inorganic P can be measured. Supernatant samples are used to compare activities at a specified time post inoculation. Phytase activity may be expressed as the number of mmoles P released per minute per ml culture supernatant. Sample activities are calculated from triplicate culture flasks where supernatants are assayed for phytase in duplicate. Activities are shown as mean_SD. Along with the observations above, a clear physiological stress associated with cultures where phosphate is limited, which adversely affected growth, may be observed and linked to the appearance of phytase activity.

3C. Concentration of Culture Supernatants

Additional evidence of phytase activity can be expected from concentrated supernatant (concentrated protein). For example, concentrated protein samples can be obtained from:
1. Cultures of bacteria from conditions of stress and low phosphate (where phytase is expected to be expressed),
2. Cultures of bacteria of high phosphate and no stress, where phytase is not expected to be produced, and
3. Cultures supplemented with low phosphate and supplemental phytate.

Silver stained SDS-PAGE gels of these concentrated protein samples are expected to show a protein profile demonstrating the appearance of a protein band (putative phytase band) in concentrated protein from condition 1 (above) which is not present in condition 2. A similar appearance of this band is also expected in condition 3, albeit at a lower level. Based on the amino acid sequence of a specific phytase, and on whether it appears to be an extracellular enzyme, the size of the protein may be approximated. It should be noted, however, that glycosylation modification, (if expressed in an organism capable of this post-translational modification), on the extracellular enzyme may increase the MW.

Example 4

PCR Amplification of Phytase Gene Fragments

PCR is performed on a standard PCR machine such as the PTC-150 Mini Cycler from MJ Research Inc. (Watertown, Mass.), the Eppendorf Mastercycler (Hamburg, Germany) or the Hybaid Touchdown thermocycler (Middlesex, UK). PCR conditions for Pwo polymerase (Boehringer Mannheim, Cat # 1644-947) comprise a 100 microliter solution made of 10 microliter of 10 X reaction buffer (10 X reaction buffer comprising 100 mM Tris HCl, pH 8-8.5; 250 mM KCl; 50 mM (NH4)2SO4; 20 mM MgSO$_4$); 0.2 mM each of dATP, dTTP, dGTP, dCTP (final concentration), 1 microliter of 100 nanogram/microliter genomic DNA, 1 microliter of PWO at 1 unit per microliter, 500 mM primers (final concentration) and water to 100 microliters. The solution is overlaid with mineral oil.

4A. Degenerate Primer Design

Based on alignments of published phytase amino acid sequences, a range of degenerate primers are designed against conserved structural and catalytic regions. Such regions included those that are highly conserved among the phytases, as well as those known to be important for enzyme structure and function.

For example, amino acid sequences for published phytases are aligned. It should be noted that many phytase sequences are publicly available from GenBank, and each is incorporated herein by reference.

Particular regions are chosen to meet the criteria above, and a range of forward and reverse primers designed from the amino acid sequences. Using the genetic code for codon usage, degenerate nucleotide PCR primers are synthesized.

As another example, primers are designed from the published amino acid sequence for different phytases from a single species (e.g., *S. Flexnarii*). These primers may be designed as follows:
1. Primer 1: Forward (5'-3') primer from, for example, the phosphate binding domain of a phytase, which should be essential for catalytic activity.
2. Primer 2: Reverse primer from a central phytase region which seems to be conserved relatively well.

All primers may be synthesized in the 5'-3' direction. The standard genetic code is used to change from amino acid to triplet codon, and standard IUB code for mixed base sites are used (e.g. to designate I for A/C/T/G).

Degenerate primers developed as described above may be used to amplify a phytase encoding region from other species by PCR, as described next.

4B. PCR Amplification of Phytase Gene Fragments

Genomic DNA from a species of interest may be used as a template for PCR amplification of putative phytase gene fragments using combinations of primers made as described above. PCR is carried out using the PCR Ready-to-go Beads from Amersham Pharmacia. Conditions are determined by individual experiments, but typically thirty cycles are run in a Techne thermal cycler. Successful amplification is verified by electrophoresis of the PCR reaction on a 1% agarose gel. A PCR phytase product that is amplified by the primers may be anticipated by a correct expected size. The product is then purified by gel extraction using the Qiaquick Spin Gel Extraction kit from Qiagen. The purified PCR product is ligated into the commercial pGEM-T Easy vector System (Promega Corporation) to facilitate cloning. Ligation reactions are incubated at 4° C. overnight in a total volume of 10 ml containing 0.1 volumes of 10×ligase buffer and 1 ml (1 U.ml$^{-1}$) of T4 DNA ligase. Typically insert DNA is used in the reaction in a 1-4:1 molar ratio of insert to vector DNA. A 100 ml aliquot of CaCl$_2$ competent *E. coli* XL-1 Blue cells are removed from -80° C. storage and thawed on ice for transformation. 31 of ligation mix is added to the cells and the mixture incubated on ice for 20 min. The cells are then heat shocked at 42 C for 1 min. and returned to ice for 5 min. The transformation mixture is added to 0.9 mL of L-broth, and the cells incubated with shaking and without selection to allow expression of the ampicillin resistance gene product before selection is applied (37_C, 1 h). Aliquots of 200, 300 and 400 ml of this culture are then spread directly on selective agar plates. Plates are incubated at 37 C overnight. Colonies containing recombinant plasmids are visualized using blue/white selection. For rapid screening of recombinant transformants, plasmid DNA is prepared from cultures of putative positive (white) colonies. DNA is isolated by the method of Birnboim and Doly following the protocol in Sambrook et al (1989). The presence of the correct insert (650 bp) in the recombinant plasmid is confirmed by restriction analysis. DNA is digested with restriction enzymes (e.g., Not1-pPst1) overnight at 37° C., and digest products visualized by agarose gel electrophoresis. A number of clones may contain the correct sized insert and can be selected for manual sequencing to see if the insert is a phytase gene fragment. Inserts are sequenced using the dideoxy chain termination method of Sanger et al (1977) with a modified form of T7 DNA polymerase (Sequenase version 2.0). The reactions are carried out using reagents supplied in the Sequenase version 2.0 kit (Amersham Life Science-United States Biochemical Corporation), following the manufacturer's protocol. Partial sequence from the ends clones may indicate that a phytase gene fragment had been cloned. Full sequencing of the double-stranded inserts is performed on plasmid DNA from these clones.

5C. Sequence Analysis

The sequences are analyzed by BLAST and protein translation sequence tools. BLAST comparison at the nucleotide level may show various levels of homology to published phytase sequences. Initially, nucleotide sequences are submitted to BLAST (Basic BLAST version 2.0) by accessing the BLAST database on the world wide web. The web site used is at http://ncbi.nlm.nih.gov/cgi-bin/BLAST. The program chosen is blastn, and the database chosen is nr. Standard/default parameter values are employed. Sequence data for putative gene fragments are entered as sequence in FASTA format and the query submitted to BLAST to compare these sequences to those already in the database.

The sequences are then subjected to a DNA-to-protein translation tool called Protein machine. This tool is also available on the web at http://medkem.gu.se/edu/translat.html. Another suitable translation tool is known as Translation Machine, available on the web at http://www2.ebi.ac.ukl/translate/. The DNA sequences of putative phytase gene fragments are inserted into the analysis block, and the standard genetic code is used as the basis for the translation. Translations are carried out in all three frames and on forward and reverse strands. The translated amino acid sequence is delivered on the screen by the analysis tool as amino acid sequence in one letter code. Ideally, analysis of the amino acid sequence will show that the fragment contains both correct ends (as used to design the primers), contains the essential P binding motif and perhaps other residues which are also present in published phytase sequences. From this, it may be concluded that the fragment cloned is a phytase gene fragment.

Sequence alignments and analysis of those alignments is carried out at the nucleotide and amino acid level using the ALIGN program (Alignment Editor Version 4/97; Dominick Hepperle, Fontanestr. 9c, D016775, Neuglobsow, Germany). In performing the analysis, subject sequences are pasted in, and the PHYLIP Interleaved format employed. The homology analysis is carried out using the "Analyze" section of the program, and specifically the option entitled "Distance Analysis." This calculates % homologies and the number of different sites between species, using a minimum of two amino acid sequences (i.e., two "species"). Minimal and maximal homologies are calculated as %. The basis for homology analysis is done as % identity, on the calculation of "number of identical amino acids (or bases) divided by the total number of amino acids (or bases) multiplied by 100 to give a percentage value. Amino acid sequences are placed into the ALIGN program along with published phytase sequences and a manual alignment at the amino acid level is carried out. From this, the deduced translation for the PCR product obtained using degenerate primers may be obtained.

Example 6

Southern Analysis for Library Production

Genomic DNA from different species is digested with a range of restriction enzymes overnight at 37° C. Successfully digested DNA is run out on a 1% agarose gel in preparation for transfer to the nylon membrane. After completion of electrophoresis, the agarose gel is soaked for 10 min. in 0.2M HCl to depurinate the DNA and then rinsed briefly in ddH$_2$O. The DNA is transferred to the Hybond™–N+ membrane.(Amersham International PLC) by alkali capillary blotting. The blot is set up so that the nylon filter is sandwiched between the gel and a stack of absorbent paper towels. A wick of Whatman 3 MM paper (Schleicher and Schuell, Dassel, Germany) is prepared on a glass plate over a reservoir of transfer buffer (0.4M NaOH). The gel is inverted on the wick, taking care to avoid the formation of air bubbles, and surrounded by strips of Nescofilm to prevent the blotting action of the paper towels from by-passing the gel at-its edges. The gel is covered with an equal sized piece of Hybond™–N+ membrane which had been cut in the corner to match the gel and pre-wetted in 3×SSC. Next, 3-5 pieces of 3 MM paper are placed on top of the filter and the blot completed by adding a 10 cm stack of blotting paper followed by a 0.5 kg weight. The blot is left for 8-24 h to transfer the DNA. The membrane is then washed briefly in 2×SSC at RT and baked in a vacuum oven at 80° C. to fix the DNA to the membrane. An isolated fragment from the procedures above is used to probe the Southern blot. It is firstly labelled with $^{32}$p isotope by use of the High Prime DNA Labelling Kit (Boehringer Mannheim). Denatured fragment is added into a random primed labelling reaction which incorporates radio-labelled adenine. The Southern blot is prehybridised for 1 hour at 42° C. in 12 mL of Easy-Hyb buffer (Boehringer Mannheim) in a hybridisation tube. Radiolabelled probe is denatured and added to 5mL of Easy-Hyb hybridisation buffer and left to hybridise overnight at 42° C. Following hybridisation, the blot is washed by incubation in 40 mL 3×SSC, 0.1%SDS for 15 min at 42° C. This low stringency wash is repeated with fresh wash solution. After stringency washing, the lot is rinsed in 3×SSC, sealed in clear plastic and exposed to x-ray film. This is left for 2 hours and the film developed. Strong hybridizing bands may be observed for a given species digest. Such results indicate that the fragment can be used as a probe for library screening.

Example 7

Isolation of a Polynucleotide Sequence From the Genome of a Species of Interest Encoding a Phytase
7A. Genomic Library Generation and Screening Following the Southern hybridization analysis, a partial genomic library may be made in order to clone a full-length phytase gene. A size restricted plasmid library targeting a digestion fragment (as estimated from Southern analysis) is generated. Digested genomic DNA is run out on a 1.25% agarose gel. The digested fragments of a preferred approximate size are extracted from the gel, and purified by Glass-Max (Gibco-BRL, Scotland). Purified genomic fragments are used in a shotgun ligation reaction with restriction nuclease linearized pSK II Bluescript vector (Stratagene). The vector is first dephosphorylated before ligation, and the ligation reaction is carried out at 14° C. overnight. The library is produced by transformation of *E. coli* XL-10 Gold ultracompetent cells (Stratagene). 100 ml aliquots of cells are removed from -80° C. storage and thawed on ice for transformation. 4 mL of b-mercaptoethanol is added to the cells on ice. 3 ml of ligation mix is added to the mixture and the mixture incubated on ice for 20 min. The cells are then heat shocked at 42°C. for 30 sec and returned to ice for 2 min. The transformation mixture is added to 0.9mL of NZY-broth, and the cells incubated with shaking and without selection to allow expression of the ampicillin resistance gene. The transformed cells are plated out on blue/white selection LB-agar plates, and left to incubate overnight at 37° C. The colonies are lifted onto nitrocellulose filters by the method of Maniatis (10% SDS—lysis, 3min; 1.5 M NaOH-denaturation, 5 min; 1.5 M TricHCln—neutralisation, 5 min; 3×SSC—rinse, 5 min). The filters are then baked for 2 hours at 80° C. under vacuum to fix the DNA. The library is screened with $^{32}$P radiolabelled 636 bp probe in the same manner as for Southern hybridisation. After hybridisation the filters are washed twice in 3×SSC, 0.1%SDS, 42° C., 15 min. The filters are then rinsed in 3×SSC, sealed in plastic and exposed to X-ray film overnight at −80° C. Positive hybridizing spots are identified on the film. These are aligned to the agar plates containing the transformants. The hybridising spots may match up to more than one single colony on the agar plates. All colonies in the radius of the hybridizing spot are picked up using sterile loops and used to inoculate 2 mL of Luria broth. The cultures are grown at 37° C. for 2 hours. Dilutions of the cultures are made from $10^{-1}$ to $10^{-5}$ and 100 mL of each sample is plated out on LB-amp agar plates and incubated overnight at 37° C. The plates which have between 10 and 150 colonies on them are chosen to go forward for a secondary screen. Colony lifts are done as before, and filters are processed using the same procedures. Fresh $^{32}$p labelled probe is prepared, and the filters screened in the same way as outlined previously. Stringency washes are carried out using 2×SSC, 0.1%SDS at 42° C. for 15 min. Filters are then rinsed in 2×SSC, sealed in plastic and exposed to X-ray film for 2 hours. The developed film should show hybridizing spots, consistent with amplification of the positive colonies from the primary screen. The film is then aligned to the plates, and the spots co-ordinated to see if they corresponded to single isolated colonies. The best positives that match up to single colonies are picked and used to inoculate Luria broth for plasmid DNA preparations. Plasmid DNA is purified by Qiaspin Mini-Prep kit (Qiagen) and restriction analysis carried out to estimate the size of the inserts. Clones that give the same restriction profile can be used to suggest an insert size. Clones may be partially sequenced to determine if they are the correct gene/gene fragment. The full sequence of these clones are then determined.

7B. Percentage Identity Comparison Between Bacterial Phytases

The deduced polypeptide product of the cloned phytase gene fragment is used for homology analysis with published phytases (see FIG. 20). The analysis shows percent identities and, together with analysis of the translated sequence, may provided evidence that the gene fragment cloned is a homolog of a specific phytase.

7C. Generation and Screening of SalI-Based Size-Restricted Genomic Library to Isolate Remainder of Phytase Gene In order to isolate the remaining portion of a gene, a second restriction enzyme may be used to generate a second partial genomic library, and fragments may then be subcloned together. The restriction endonuclease recognition sites present within a cloned phytase sequence are identified using Webcutter. Of particular interest are sites for enzymes that are used in the Southern analysis discussed above. Very large fragments (e.g., 8 Kb), would be difficult to clone in a plasmid-based library. A low degree of hybridisation with a specific restriction enzyme band argues against use of such in a library screen, and the presence of two bands in a restriction enzyme lane is likely to complicate the screening process. The library is made as before in pbluecript SKII, and screened using the same probe. A selection of positive hybridising colonies are chosen and aligned to colonies on the plates. Matching colonies are picked for plasmid DNA-preparations. Restriction analysis may show how many clones have inserts. These clones are then fully sequenced.

7D. Amplification of Contiguous Phytase Gene for Heterologous Expression

A composite phytase sequence is produced from genomic clones and used to design a number of upstream and downstream primers which could be used to amplify a contiguous phytase gene sequence. PCR amplification is also designed to facilitate cloning and expression of the complete phytase gene in to a heterologous expression vector (e.g., pGAPT-PG, a 5.1 Kb construct provided by Genencor International, Inc.). Restriction enzyme sites within the multiple cloning site of the vector which are not present within the phytase gene sequence are determined. A number of 5' and 3' flanking primers may be designed using the phytase gene sequence, and modified to include the restriction enzyme recognition sites for these enzymes.

Restriction enzyme recognition sites are designed into the primer sequences to facilitate cloning into the expression vector. The upstream and downstream flanking regions used to design the primers are arbitrarily chosen at approximately 100 bp upstream from the ATG (start) codon and downstream from the TAG (stop) codon respectively. The gene sequence used is also chosen to contain as equal balance of bases as possible.

Amplification of the phytase gene by PCR may be done using genomic DNA combinations of primers. PCR should amplify a region corresponding to the full-length phytase gene. The desired product produced by amplification with the primers is cloned into a vector and several clones which contain the correct size of insert are selected for sequencing. Homology analysis of the clone sequences is then performed and a full length phytase sequence determined.

PCR amplification genomic DNA is carried out using a combination of 5' primers and 3' primers, and using a high fidelity DNA polymerase, Taq, to minimise error for expression of the phytase gene. This polymerase is Taq DNA polymerase (Stratagene) and comes as part of the Taq DNA polymerase kit for PCR. For these reactions, reaction buffer, dNTPs, target DNA and primers are mixed together, and 2.5 units of Taq polymerase added in a final reaction volume of 50_L. After amplification, a 5_L aliquot of the reaction mixture is analysed by gel electrophoresis. Selected fragments are cloned directly into the vector pCR-Blunt II TOPO (Invitrogen), and a select number of clones analysed to confirm the presence of the correct insert. (Blunt-ended PCR products that are generated by Taq DNA polymerase are cloned into the Zero Blunt_TOPO_PCR cloning kit (Invitrogen). This vector contains a MCS site and a kanamycin gene for anitbiotic resisistance, but also allows selection based on disruption of the lethal E. coli gene ccdb, as opposed to blue-white slection. Purified PCR product (50-200 ng) is added to 1_L of pCR-BluntII-TOPO vector and the reaction volume made up to 5_L with sterile water. This is mixed gently at left to incubate for 5 min at room temperature. 1_L of 6×TOPO Cloning Stop Solution is added, and the reaction left on ice or frozen at −20° C. for up to 24 hours for transformation.) The integrity of the engineered restriction sites are also confirmed by this analysis. A number of clones are prepared and sequenced. Sequence analysis may confirm the presence of a full-length phytase gene. This gene may then be taken forward for expression in a heterologous system, and subsequent biochemical characterisation of the enzyme.

7E. Analysis of Phytase Sequence

An alignment is made of the isolated sequence and published phytases and homology analysis done, on a percentage identity basis.

7F. Biochemical Characterisation of a Phytase

To prove that the cloned gene represents a specific phytase activity, and to characterise that activity, a range of biochemical analyses are carried out on the over-expressed enzyme. Preliminary characterisation may indicate that the gene is producing a phytic-acid hydrolysing activity. This analysis can be extended to examine activity at different pHs, temperatures and against different substrates.

Transformant are taken forward for these analyses, and cultures are harvested at optimum expression time, as determined above. With phytic acid as the substrate, the pH effect on enzyme activity can be shown. The substantially purified enzyme sample is desalted from culture supernatant, and eluted in 0.025 mM sodium acetate pH 5.0. This is then added to substrate which is made in solutions of the following buffers: pH 3.0: 0.4M glycine-HCl, pH 4.0: 0.4M Sodium acetate, pH 5.0: 0.4M Sodium acetate, pH 6.0: 0.4M imidazole-HCl, pH 7.0: 0.4M Tris-HCl, pH 8.0: 0.4M Tris-HCl pH 9.0: 0.4M Tris-HCl. An optimum pH for the phytase activity may be determined, as well. Little activity seen when 4-nitrophenyl-phosphate is used as the substrate indicates a high level of specificity for the phytic-acid substrate.

The temperature profile of the enzyme is characterised using pH 5.0 buffer, over a range of temperatures, using phytic acid as the substrate. The phytase temperature activity range and optimum activity temperature can be determined.

Preliminary stability studies may also be carried out on the phytase. Samples of the protein are left at −20° C., 4° C., and 37° C. overnight, and then assayed under standard conditions. Samples may also be exposed to high temperature (e.g., 85° C. for 20 minutes, and 100° C. for 10 minutes) to determine the thermostability of the phytase activity. Residual activity is based on comparison to phytase activity determinations taken from the samples before exposure to each condition. Samples may be assayed afterwards in the same assay conditions.

The following set of examples pertain to the isolation and characterization of mutant AppA phytases from E. coli.

Example 8

Construction of B. Subtilis Strains Containing AppA

A B. subtilis strain expressing the E. coli appA gene was constructed in a series of steps.

Figure 3:
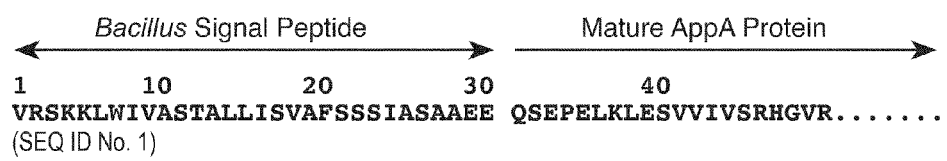
FIG. 3 shows the sequence of the composite Bacillus signal sequence and the mature AppA protein found in the fusion phytase protein expressed in Bacillus subtilis strain 1 8B2. This Bacillus strain was produced as described in Example 1.

The 5' region of the appA gene sequence (starting with the first amino acid codon of the mature phytase sequence to the stop codon) was first fused with an upstream sequence containing the PstS promoter (Qi et al., 1997) and encoding a 30 amino acid composite signal sequence of Bacillus origin (see, e.g., FIG. 3). This was accomplished using PCR fusion of the appA gene fragment with a fragment derived from plasmid pSW4. Plasmid pSW-4 (7.769 kb) contains a pUC replication origin and kanamycin (Km) determinant for selection purposes in *E. coli*. In addition, pSW-4 contains the subtilisin protease gene cassette flanked upstream by the PstS promoter, yhfO and a partial yhfP gene and downstream by a chloramphenicol (Cm) resistance gene (cat), and part of the yhfN gene.

Following replacement of the subtilisin protease cassette by the appA gene and transformation of the resulting products into *E. coli*, Km resistant transformants were screened by restriction endonuclease analysis for the presence of appA sequences. One clone, designated pLE18 (FIG. 1, top), with the desired fusion of the appA gene with the *Bacillus* transcriptional, translational and secretory regulatory sequences was chosen for further study.

Figure 2:
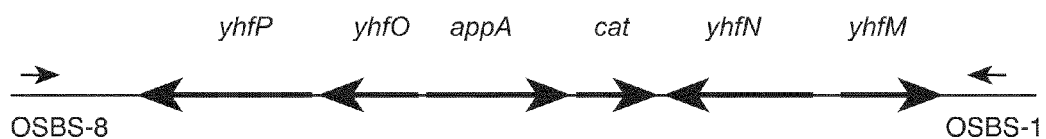
FIG. 2 depicts the genome map of Bacillus subtilis strain 18B2. OSBS-1 and OSBS-8 indicate the approximate location where these primers hybridize with the Bacillus genome to amplify the appA containing region.

The next step involved the stable integration of the appA gene into the *B. subtilis* chromosome. Plasmid pLE18 was introduced into competent cells of strain OS21.10 and appA integration events were selected by plating onto Luria-Bertani (LB) medium containing chloramphenicol. PCR amplification of an appropriately integrated appA construct using primers OSBS-1 and OSBS-8 is predicted to generate a 6.9 kb product (FIG. 2). One Cm resistant transformant, designated 18B2, produced a characteristic 6.9 kb band following PCR analysis. DNA sequence analysis of the 18B2 PCR product confirmed the presence of an intact PstS promoter located upstream of the entire mature appA gene fused in frame to the *Bacillus* signal peptide (FIG. 3).

Example 9

Random Mutagenesis of the AppA Gene and Screening for Increased Activity Upon Expression in a *B. Subtilis* Host Phytase mutants that demonstrate enhanced activity in *B. subtilis* were generated using a random mutagenesis approach. Improved appA variants were identified primarily through the use of a high throughput phytate growth screen. However, a limited number of clones from library #1 were screened using a fluorescence-based assay (FIG. 4).

2A. Library Construction

Z-Taq™ polymerase (Takara, available from Panvera, Madison, Wis.) was used according to the manufacturers recommendations to amplify the 6.9 kb region containing the appA gene. This treatment was sufficient to produce a mutagenic frequency of approximately 0.1%. Following each cycle of PCR mutagenesis, the library was introduced into *B. subtilis* strain OS21.10 and transformants were initially selected on LB plates containing chloramphenicol (5 µg/mL). The chloramphenicol-resistant colonies were collected by scraping the plates and resuspending the cells in P1 minimal medium containing 100 µM phosphate and chloramphenicol. Following an appropriate outgrowth period, which varied from 2 hrs to overnight, the optical density of the cell culture was measured. The cells were diluted with a MES-1 medium (pH 6.0), containing 50 µM phytate to an approximate cell density of 0.5 cells/75 µL. The diluted cells were dispensed into 384-well microtiter plates and incubated at 37° C. for 41 hours. Following growth on phytate, cell densities (OD600) were measured with a plate reader and the results compared to the level of growth achieved with the 1 8B2 control strain.

Figure 4:
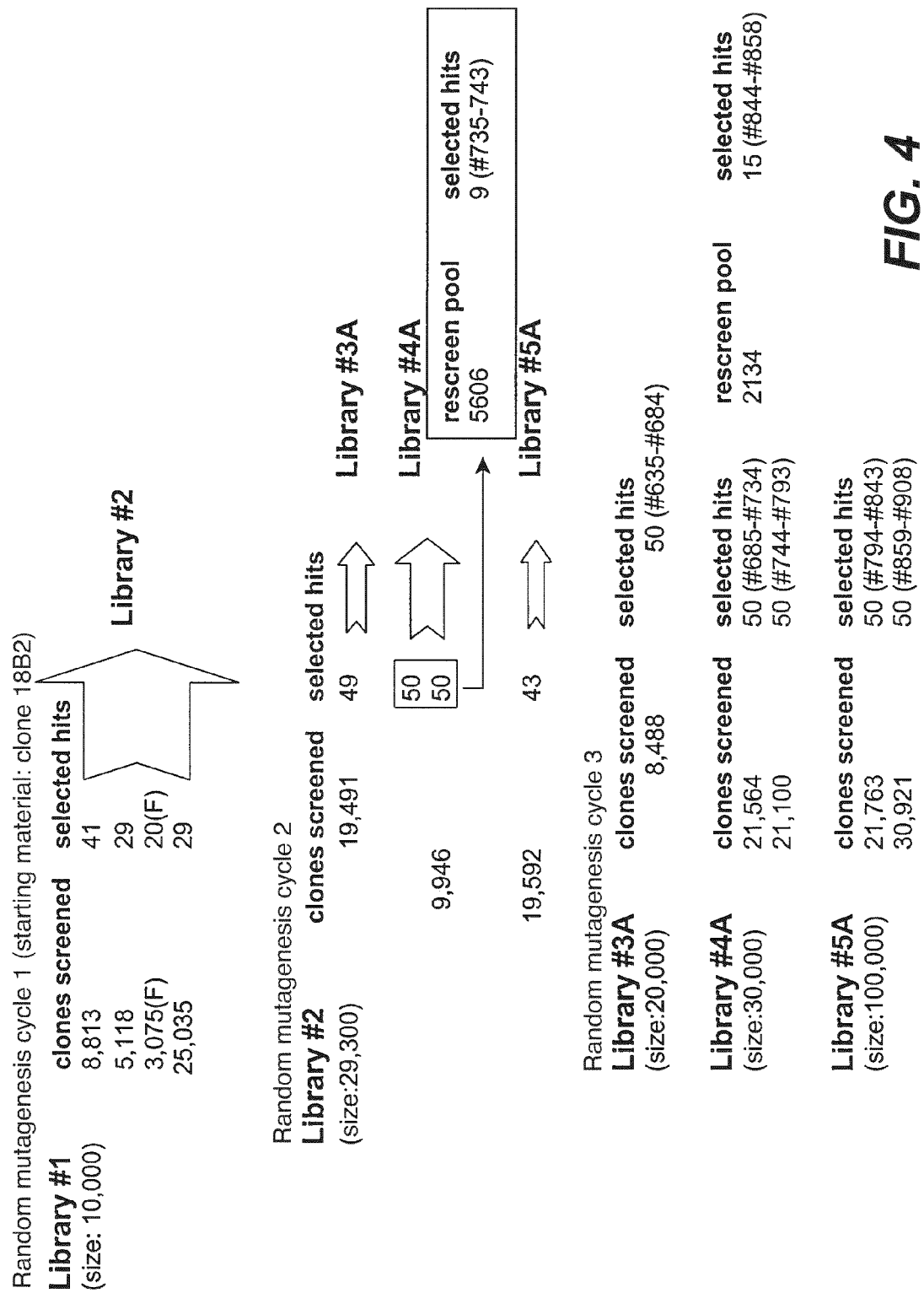
FIG. 4 outlines the screening strategy used to provide directed evolution of the AppA phytase expressed in Bacillus. Example 2 provides details of this strategy.
Figure 5:
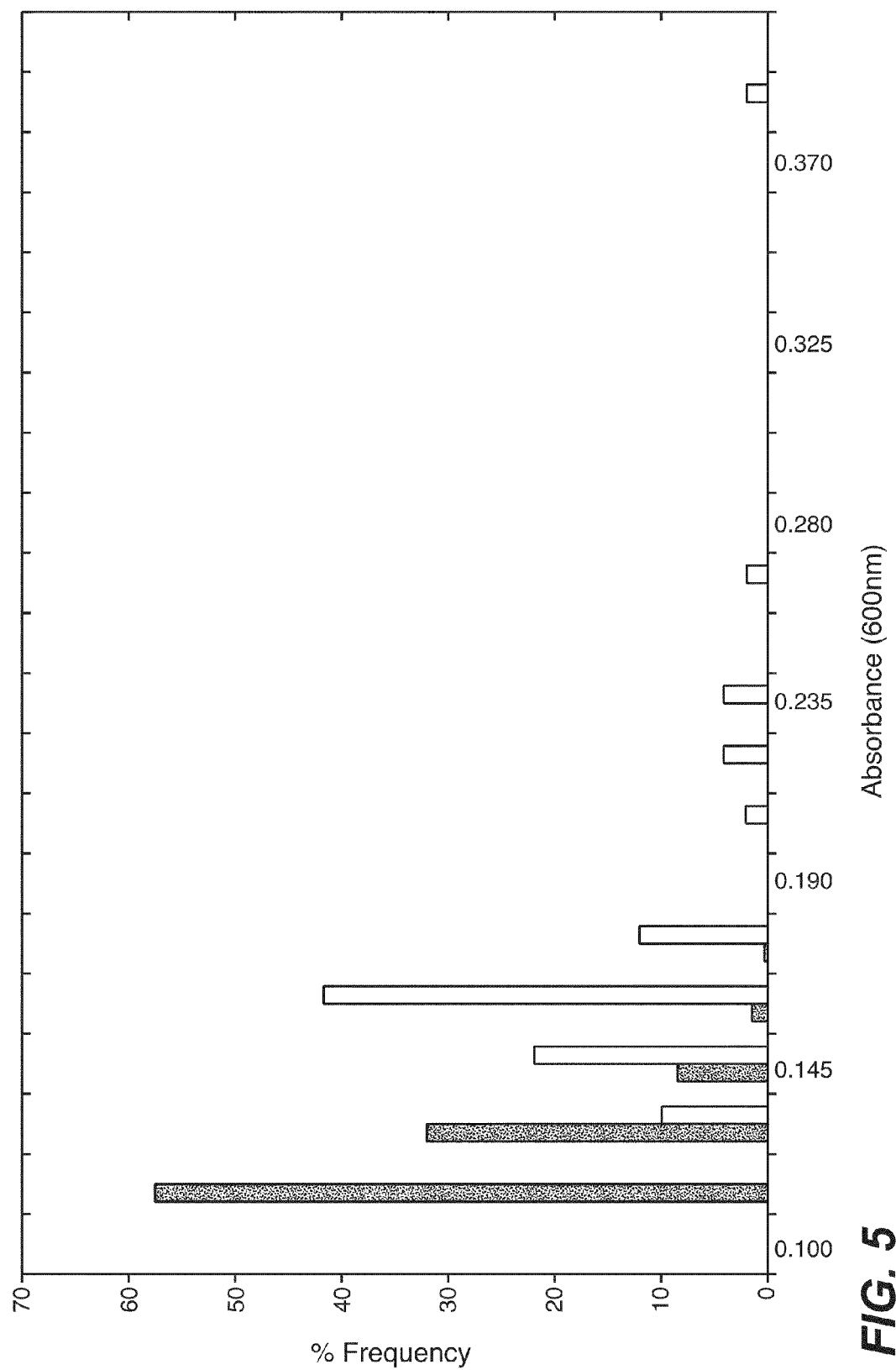
FIG. 5 shows relative growth of Bacillus clones with phytate as the sole source of phosphate. Cell growth was shown using photocytometry, measuring relative absorbance at 600 nm, which correlates to cell density. The graph shows the % frequency of all clones screened after 3 cycles of random mutagenesis (dark bars) and of a pool of 50 selected clones (designated PHY859-908; light bars) having markedly improved growth utilizing phytate as a phosphate source in comparison to clones having the sequence found in clone 18B2 (i.e., the non-mutagenized sequence). Measurements were taken after growing individual clones for 41 hours at 37° C. in MES-1 medium with 50μM phytate.
Figure 6:
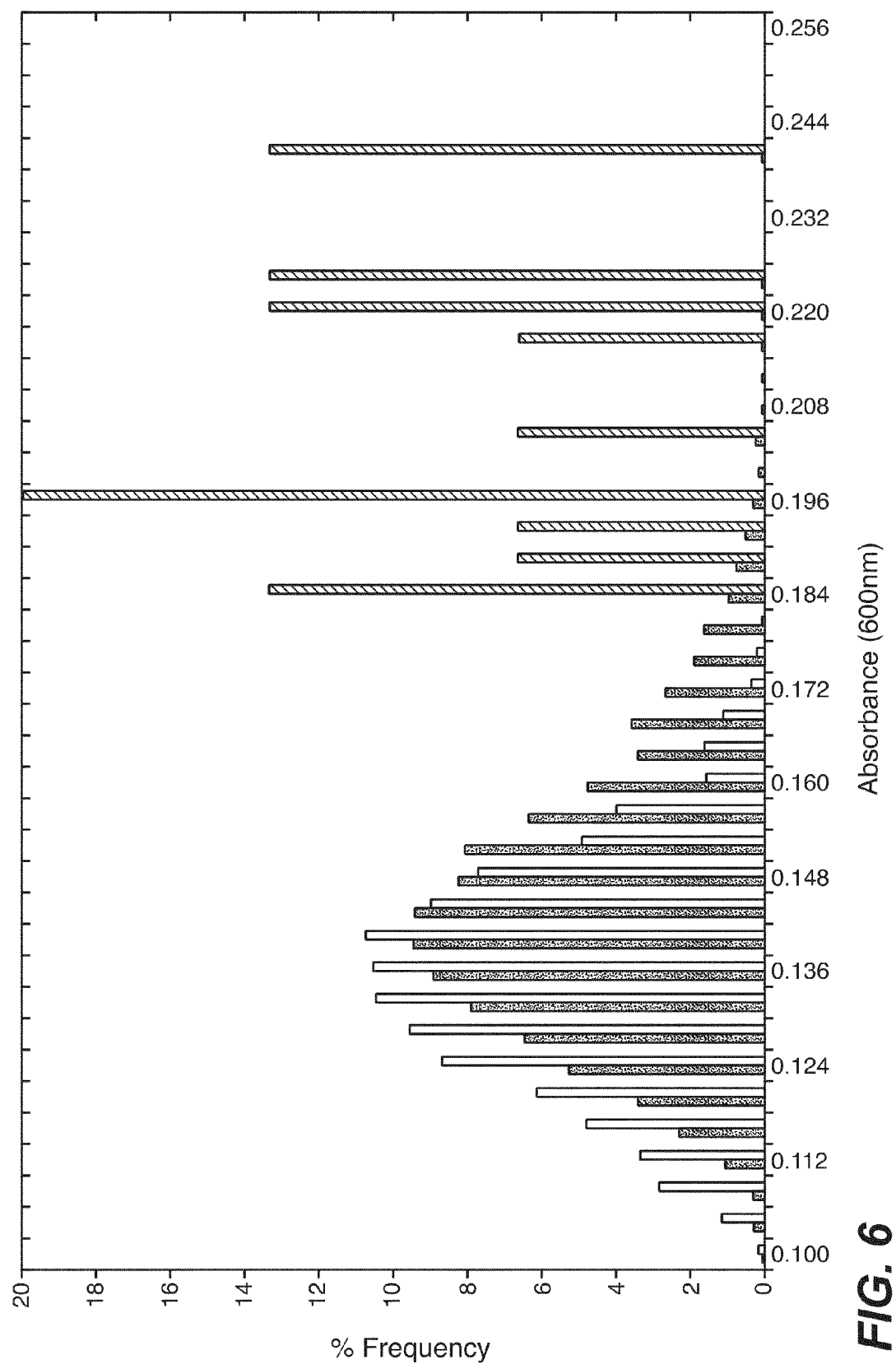
FIG. 6 shows relative growth of 3 pools of Bacillus clones having phytate as the sole source of phosphate. Cells were grown and measured as described for FIG. 5. The graph shows %-frequency of 2383 clones encoding and AppA having the sequence found in clone 18B2 (light bars), 2134 clones having gone through three cycles of mutagenesis (dark bars), and 15 clones selected from this latter group (crosshatched bars), which were designated clones PHY844-858.

FIG. 4 shows the screening strategy following each cycle of appA gene mutagenesis using the error-prone PCR described above. After screening libraries #1 and #2, selected "hits" (i.e., clones with growth characteristics that were superior to that of a *B. subtilis* strain expressing the wild-type AppA phytase, strain 18B2) were pooled and isolated genomic DNA from these clones was used to construct the third generation libraries #3A, #4A and #5A. Screening of these third generation libraries resulted in the identification of numerous hits that grew significantly better than 18B2 with phytate as the sole source of phosphorus (FIG. 5). Occasionally, selected hits identified in the third generation libraries were pooled and re-screened in the 384-well format. This process generated several hits that performed better than 18B2 (FIG. 6).

Example 10

Characterization of Phytase Activity Improvements

The ability of several hits identified in the 384-well plate screening process to grow with improved growth rates using phytate was further characterized.

10A. Growth With Phytate as the Sole Phosphorus Source

Figure 7:
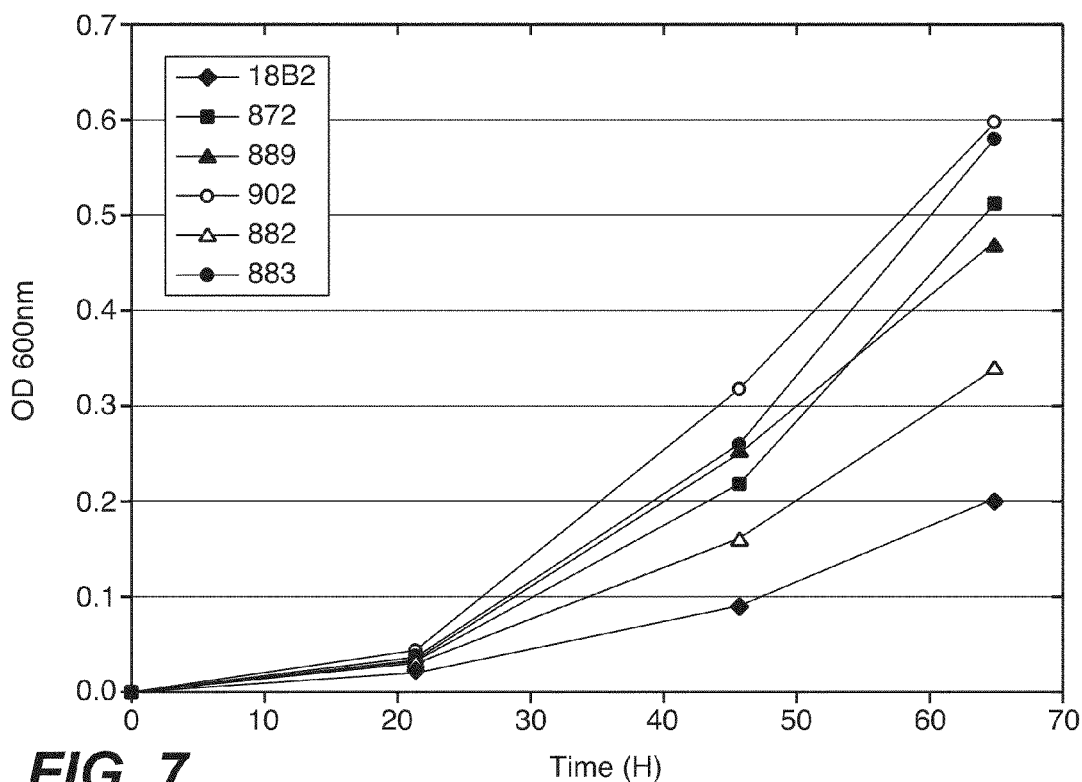
FIG. 7 shows a graph of relative growth rates of Bacillus clones expressing phytase having the 18B2 sequence (closed diamond), as well as clones expressing various mutant phytases, as indicated in the legend. Clones were grown in 5 ml MES-1 medium (pH 6.0) containing 50 μM phytate and 5 μg/ml chloramphenicol at 37° C. with shaking at 250 rpm. All of the mutant clones represented in the graph grew at a significantly faster rate than the 18B2 clone.

Seed cultures of 18B2 and different hits were inoculated into test tubes containing 5 mL MES-1 medium (pH 6.0), 50 µM phytate and chloramphenicol. After 65 hrs of incubation at 37° C. with shaking, hits PHY902, PHY883, PHY872, PHY889 and PHY882 grew with significantly faster growth rates than the 18B2 control strain (FIG. 7).

10B. Accumulation of Phytase Activity Under Phosphate Starvation Conditions

Figure 8:
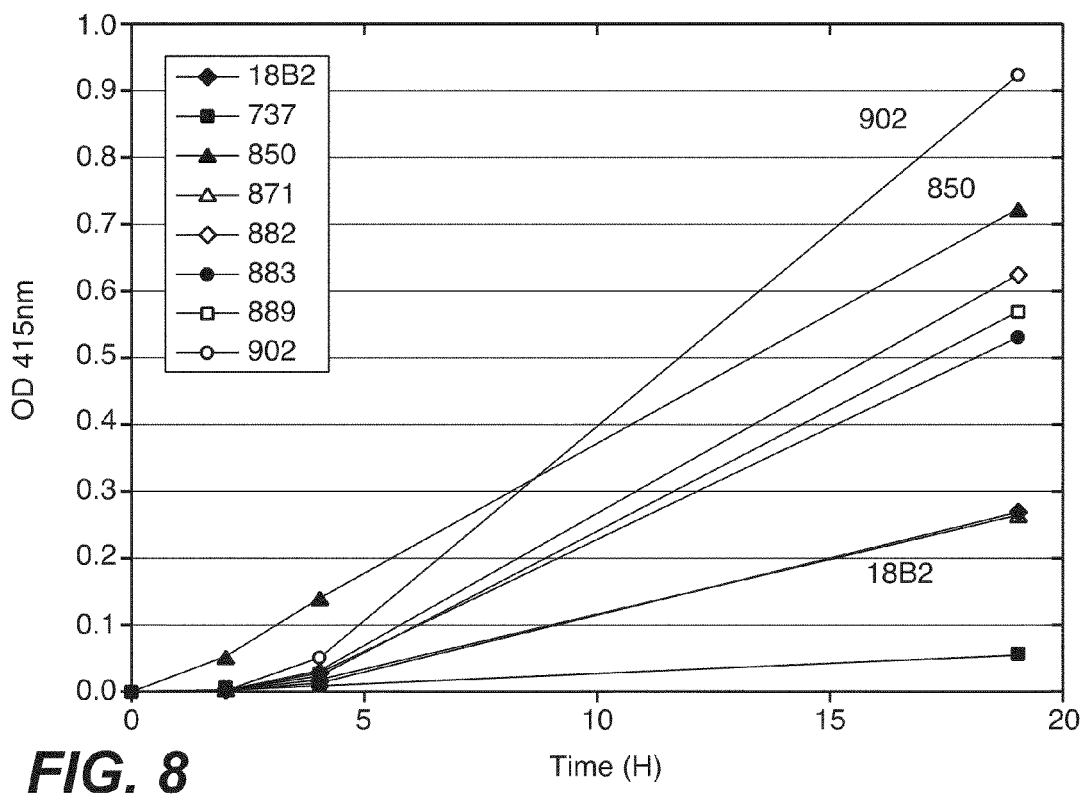
FIG. 8 shows a graph of the accumulation of phytase activity for different clones grown in phosphate-starved, high density cultures. Bacillus clones were first grown in 5 mL LB medium containing chloramphenicol. Cells from stationary phase cultures were washed and resuspended to approximately the same density in P1 medium lacking a phosphorous source. Production of phytase activity over time was assayed using a molybdate-vanadate phosphate assay, where color (optical density) was measured at 415 nm. Several of the mutant clones accumulated more phytase activity over time under these conditions than the 18B2 control strain.

Several hits were examined to correlate the increased growth rates on phytate observed with an increase in phytase activity. Select hits PHY902, PHY850, PHY882, PHY889, PHY883, PHY747 and the parent strain 18B2 were first grown in 5 mL LB medium containing chloramphenicol. The cells from stationary phase cultures were washed and resuspended in P1 medium lacking a phosphorus source to approximately the same cell density. Phytase activity was monitored over a 19 hour time period using a modified molybdate-vanadate phosphate assay (read at 415 nm). All of the hits examined (except for PHY747) accumulated up to 3-fold more phytase activity than the 18B2 control strain (FIG. 8).

10C. Affect of pH on Growth of Host *Bacillus* Containing an AppA Mutant

Figure 9:
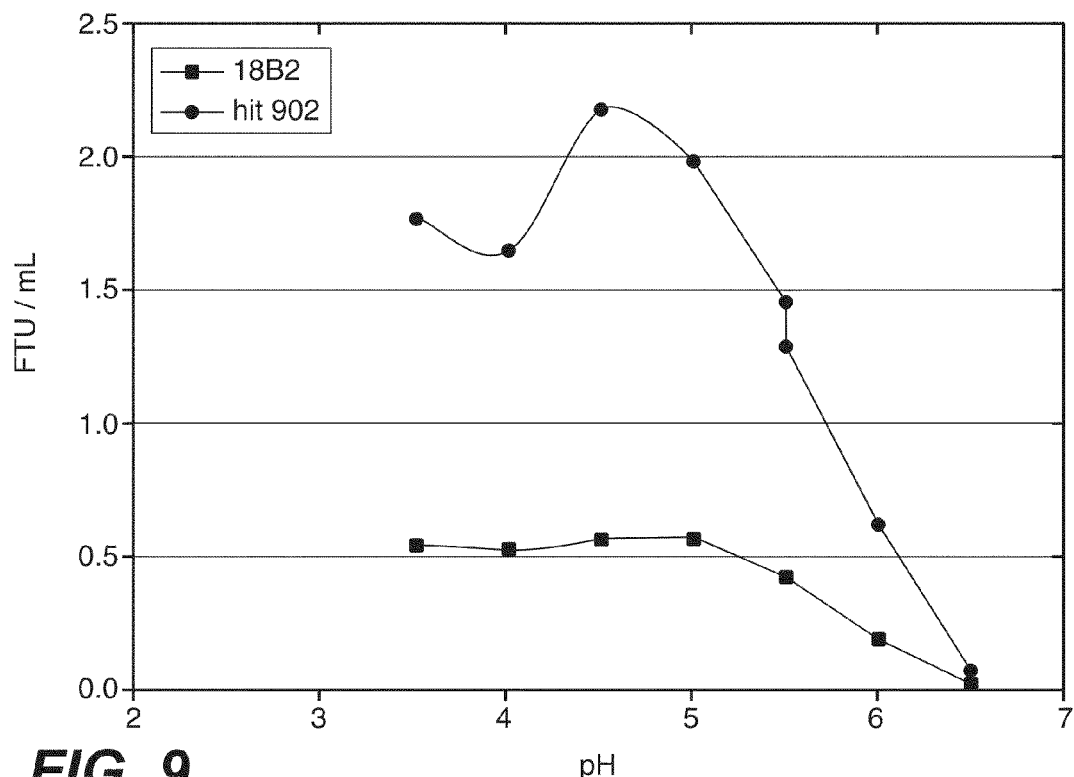
FIG. 9 shows the pH activity profiles of phytase produced by a mutant Bacillus strain (PHY902) and the 18B2 control strain. Clones were grown in LB medium, then resuspended in P1 medium lacking a phosphate source. Following incubation, supernatant from the cultures was tested for phytase activity. Both clones showed a pH optimum around 4.5, but the supernatant from the PHY902 culture had 4-fold greater phytase activity.

The phytase activity present in culture supernatants of strains 18B2 and PHY902 were examined over a range of pHs (3.5-6.5) to determine the pH optimum from the pH-activity profiles. The 18B2 and PHY902 samples were generated by resuspending LB grown cells in P1 medium lacking a phosphate source. Following incubation, 18B2 and PHY902 culture supernatants were prepared and used in phytase assays. The results show that the phytase activity (expressed as phytase units (FTU) per ml) associated with PHY902 culture supernatants had a pH optimum around 4.5, which is more or less equivalent to the wild-type enzyme expressed by strain 18B2 (FIG. 9). More importantly, however, the PHY902 phytase sample contained almost 4-fold more activity than the 18B2 sample.

10D. Transfer of Mutant Gene to New Host to Show Mutation/Activity Relationship

Figure 10:
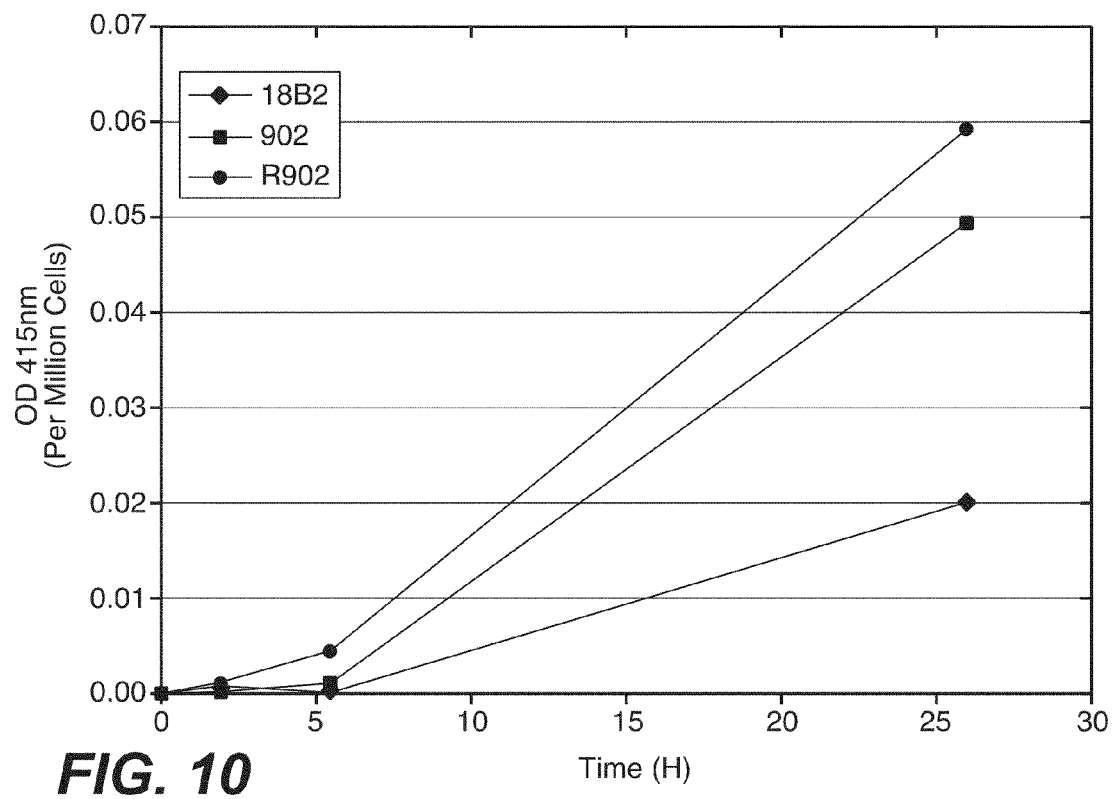
FIG. 10 shows relative phytase activity in culture supernatants from B. subtilis clones containing the 18B2 control appA (diamonds) and the PHY902 mutant (squares), as well as cultures of B. subtilis transformed with the appA gene amplified from the PHY902 mutant (R-PHY902; circles). Supernatants were generated as described for FIG. 8. The 3-fold increase in activity in the re-transformed B. subtilis clone as compared with the 18B2 control confirmed that the improved activity of the PHY902 mutant is linked to the appA gene.

In order to determine if the phytase activity improvement observed in PHY902 culture supernatants was linked genetically to the appA gene, the entire appA gene containing region of strain PHY902 was PCR amplified from genomic DNA and the resulting 6.9 kb product was used to re-transform *B. subtilis* OS21.10. Following transformation, a single chloramphenicol-resistant colony, designated R-PHY902, was chosen for further analysis. Culture supernatants of 18B2, PHY902 and R-PHY902 were generated as previously described and used in phytase assays. A R-PHY902 culture supernatant contained 3-fold higher phytase activity than those produced by 18B2 confirming that the improvement in activity was linked to the appA gene present in clone PHY902 (FIG. 10).

10E. Phytase Production of Cells Grown With Free Phosphate

Figure 11:
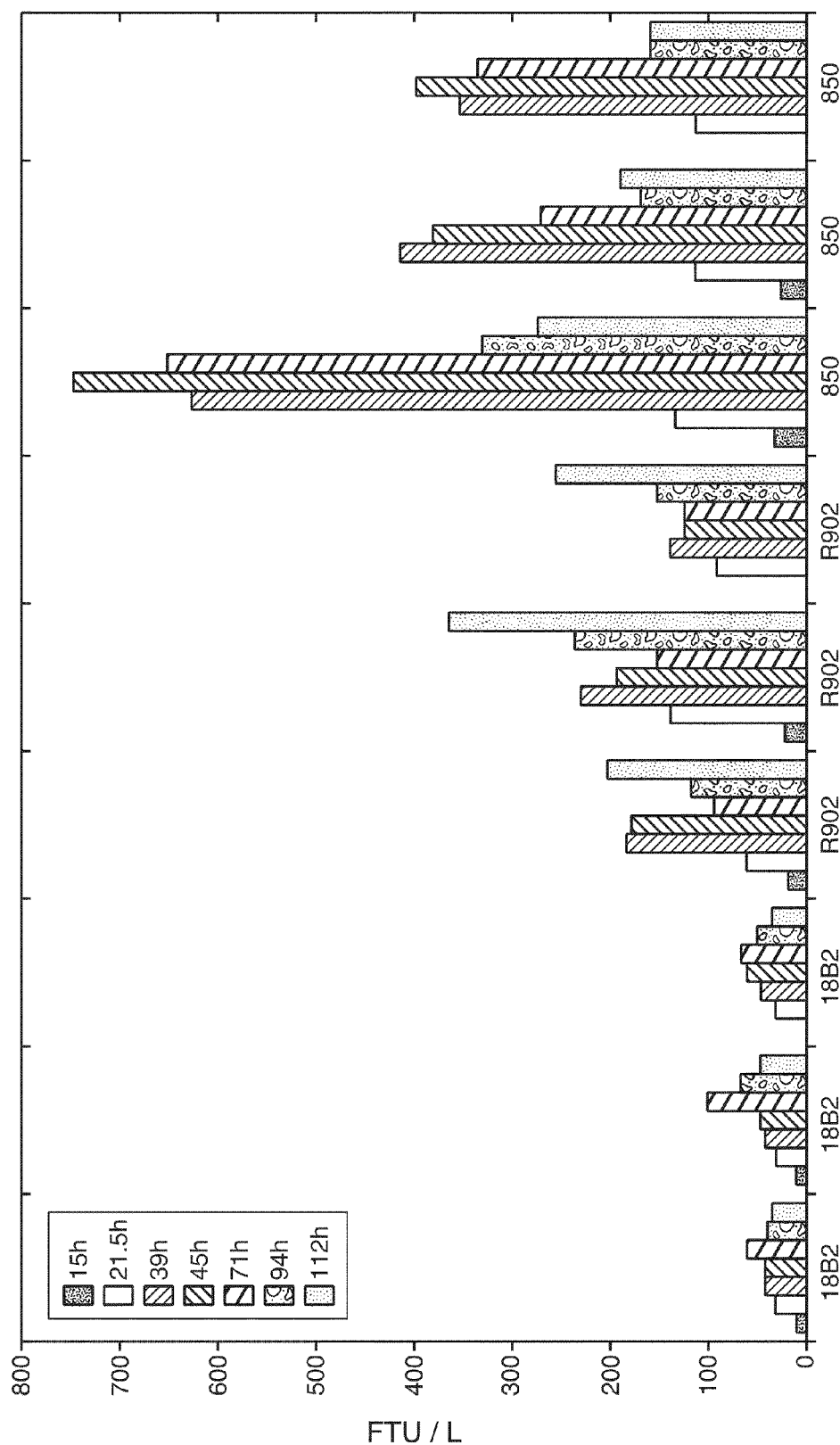
FIG. 11 shows relative phytase activity in supernatants of cultures of indivudal B. subtilis clones containing the 18B2, PHY850 or R-PHY902 appA gene. Single clones were used to inoculate 4 mL P1 medium (pH 7.3) containing 100 μM $PO_4$ and grown overnight at 37° C., with shaking. Dilutions of these cultures were used to inoculate 250 mL baffled shake flasks containing 25 mL P1 medium (pH 7.3) and 100 μM $PO_4$ to give a final density of $3.2 \times 10^6$ cells per 25 mL. The 18B2 strain had an average of 43 FTU/L, while the R-PHY902 cultures averaged 180 FTU/L (4-fold higher than control) and the PHY850 averaged 462 FTU/L (almost 11-fold higher than control).

Clones 18B2, R-PHY902, and PHY850 were examined for phytase production/activity under growth conditions. A single colony of each clone was used to inoculate 4 mL P1 medium, pH 7.3 containing 100 µM PO4. Following overnight incubation with shaking at 37° C, appropriate dilutions of the starter cultures were used to inoculate 250 mL baffled shake flasks containing 25 mL P1 medium (pH 7.3) with 100 µM PO4 (in triplicate) to give a final density of 3.2×10⁶ cells/25 mL. The cultures were monitored for both cell density (OD600) and phytase activity. FIG. 11 shows that R-PHY902 supernatants had an average activity of 180 FTU/L. This represents a 4-fold level of improvement in activity over that of the parental strain 18B2 (43 FTU/L). The PHY850 supernatants, however, contained an average activity of 462 FTU/L. This represents an almost 11-fold improvement over the activity observed for parental strain 18B2.

The entire appA gene containing region of strain PHY850 was PCR amplified from genomic DNA and the resulting 6.9 kb product was used to retransform $B.$ $subtilis$ OS21.10. Following transformation, two chloramphenicol resistant colonies, designated R-PHY850-4 and RPHY850-8, were chosen for further analysis. Culture supernatants of 18B2, R-PHY902, R-PHY8504 and R-PHY850-8 were generated under growth conditions in a limited phosphate medium as previously described (see above). The R-PHY850 culture s supernatants contained, on average, greater than 8-fold higher phytase activity than produced by 18B2 (data not shown), thereby linking the improvement in activity to the appA gene present in clone PHY850.

Example 11

Sequence Analysis of appA Mutants

DNA sequence analysis of the appA gene from phytase variants PHY850 and PHY902 revealed the presence of amino acid changes in both the mature protein as well as in the signal peptide sequence (FIG. 12). The appA gene from both PHY850 and PHY902 harbored a His to Arg change at position 143. In addition, the PHY850 appA gene also contained a missense mutation in the signal peptide at codon position I1, resulting in a replacement of serine for leucine. Examination of the crystal structure of the $E.$ $coli$ phytase revealed that amino acid residue 143 (residue 113 in the mature protein) is close to, but not intimately associated with the phytate binding pocket (Lim et al., 2000). In addition, the S11 L change in the protein produced by PHY850 is localized to the hydrophobic core (H domain) of the signal peptide and, therefore, may be responsible for a more efficient membrane translocation and/or processing of the precursor phytase protein. These improvements contain unique amino acid changes that could not have been predicted by a rational design approach.

The appA variants PHY850 and PHY902 were identified in the third generation error prone PCR libraries #4A and #5A, respectively, (see, FIG. 4). However, sequence analysis of clones PHY735 and PHY736 demonstrates that the H143R mutation could be detected as early as the second generation error prone PCR library #2 (FIG. 12). PHY736 was found to harbor two additional amino acid changes (W89R and A103V). Two H143R containing mutants, PHY679 and PHY846, were identified as hits from the third generation libraries #3A and #4A, respectively. PHY679 contains three additional amino acid changes (T56A, N156K and G258P).

The T56A change of PHY679 is located 4 residues from the AppA active site RHGXRXP (SEQ ID No. 30) motif Clone PHY846 contains only one additional change, Q214R.

Example 12

Random Mutagenesis of the PHY850 AppA Gene and Screening for Activity Productivity Improvements in a $B.$ $Subtilis$ Host Phytase mutants that demonstrate enhanced productivity in $B.$ $subtilis$ were generated using a random mutagenesis approach. Construction of the appA library was performed as follows: Ex Taq™ polymerase (Takara, available from Panvera, Madison, Wis.) was used to amplify the 6.9 kb region containing the PHY850 appA gene using the OSBS-1 and OSBS-8 primers described above. The PCR reaction conditions were modified slightly from the manufacturer's instructions to include the addition of 6% DMSO. Following mutagenic PCR, the amplified product was introduced into $B.$ $subtilis$ strain OS21.10 and transformants were selected on LB plates containing Cm (5 µg/mL). This library was designated #11 A.

Screening of the appA library involved two stages of growth. In the first stage, single colonies of library #11 A were robotically picked from LB Cm plates with the BioPick™ instrument (BioRobotics, Woburn, Mass.) and plated into 96-well polypropylene microtiter plates containing 150 µL P7 medium with 10 µM $PO_4^{-3}$ and Cm (5 µg/mL). The microtiter plates were incubated at 37_C for 24 hours with shaking (550 rpm) and the resulting cultures were used as inocula for the second stage of growth. Ten µL of the primary growth culture was transferred with a Multimek96™ liquid handling instrument (Beckman Instruments, Fullerton, Calif.) to fresh 96-well microtiter plates containing 150 µl P7 medium with 100 µM $PO_4^{-3}$ and Cm (5 µg/mL). These secondary cultures were allowed to incubate at 37_C for 44 hr with shaking (550 rpm).

Following incubation, the plates were centrifuged for 20 min @ 3500 rpm and supernatant samples (12.5 µL) from four 96-well plates were transferred to a single 384-well polystyrene microtiter plate. Phytase activity assays were performed by adding a phytate substrate solution to each well (25 µL of 0.7% phytate in 0.25 M HAc (pH 4.5) and 1 mM $CaCl_2$) and the plates were incubated for 60 min @ 37_C. Immediately after the 60 minute incubation period 25 µL/well of molybdenum-vanadate color reagent (Food Chemicals Codex, p. 809) was added to detect the liberated phosphate. The absorbance at 415 nm (A415) of each well was determined after 14 hr (overnight) incubation at room temp with a Perkin Elmer HTS 7000 Plus microtiter plate reader.

Figure 13:
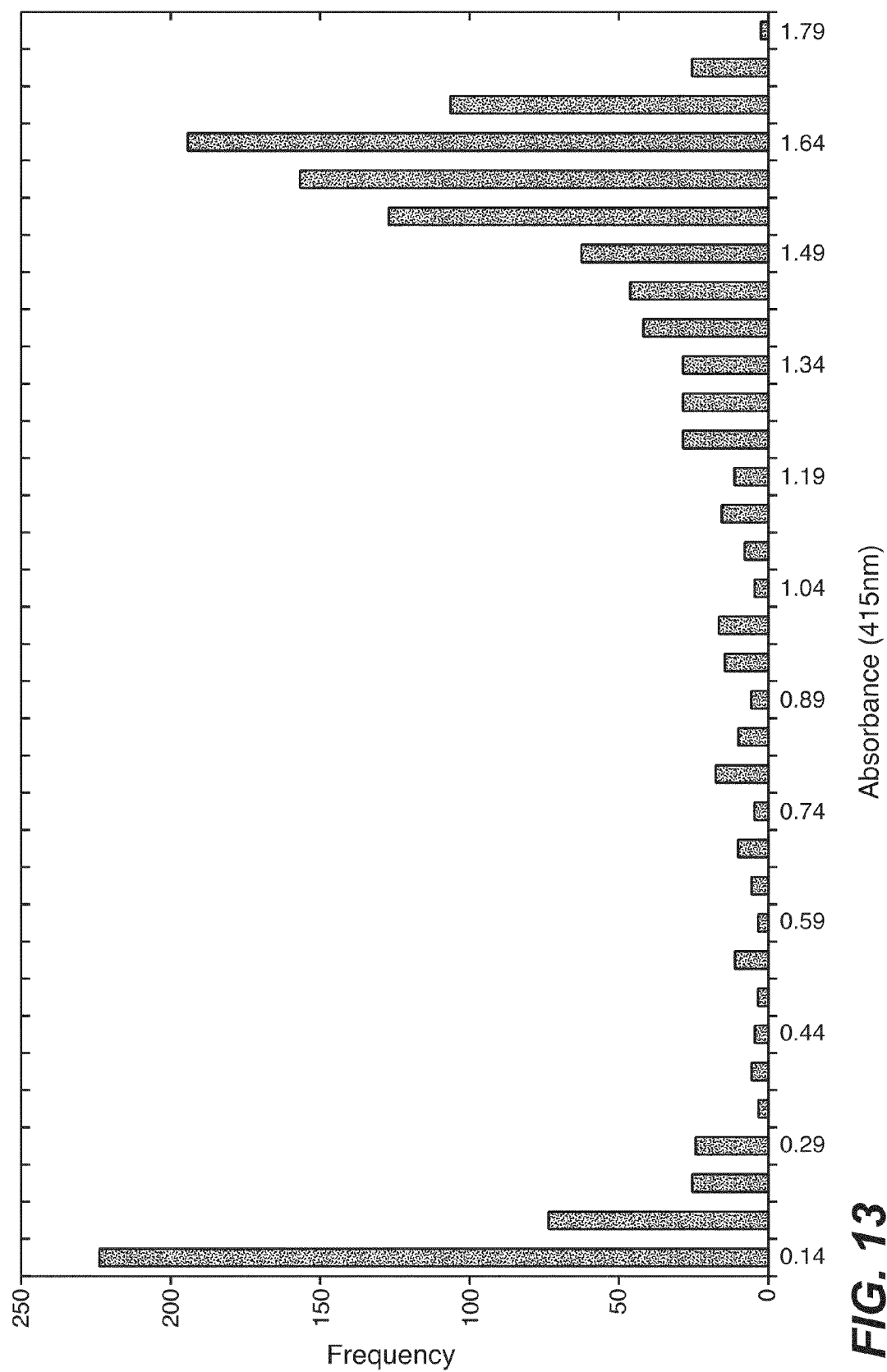
FIG. 13 shows relative phytase activity in the culture supernatant of members of a library of Bacillus clones. The library was generated by transforming hosts with amplification products from mutagenic PCR amplification of the PHY850 appA. Release of phosphate from phytase was measured by determining absorbance at 415 nm in a molybdenum-vanadate assay. Production and screening of the library is described in Example 5. Clones expressing the parent PHY850 would typically fall in the 1.2-1.4 range under these assay conditions.

A total of 1344 Cm-resistant library members were screened using the microtiter phytase assay. FIG. 13 shows a distribution of phosphate release of the examined clones as a function of their representation frequency in the library. The range of potential activities varied widely due to the rather high mutagenic frequency. The parent PHY850, under these assay conditions would typically be in the 1.2-1.4 range. Library clones with absorbance readings (A415) of less than 1.0 likely represent clones where mutations have resulted in either a marked reduction or elimination of the phytase activity. The three clones with the highest release of phosphate (A>1.7), designated PHY1361, PHY1363 and PHY1373, were chosen for further analysis.

Example 13

Sequence Analysis of Mutants of PHY850

DNA sequence analysis of the appA genes from the phytase variants PHY1361, PHY1363 and PHY1373 revealed the presence of several amino acid substitutions (FIG. 14). The appA gene from PHY1361 contained three amino acid substitutions (K73E, E414D, and L440S). The appA genes from PHY1363 and PHY1373 were discovered to be identical and contained two amino acid substitutions (I85V and E414V). In addition, these appA variants also contained the mutations present in the PHY850 parent (S11L and H143R). All of the predicted amino acid substitutions were localized in the mature protein and no new changes were found in the signal sequence. Interestingly, both the PHY1361 and PHY1363/PHY1373 appA genes contained an amino acid substitution at position 414 near the C-terminus of the protein. In addition to the mutations responsible for the amino acid substitutions, two identical silent mutations were found in the coding sequence of the 1361 and 1363 appA genes. These silent mutations were in codons 5 (Lys) and 183 (Ala), representing the changes aaa>aag and gct>gcc, respectively.

Example 14

Characterization of Phytase Activity of the Mutants of PHY850

14A. Phytase Production of Cells Grown With Free Phosphate

The phytase activity associated with the supernatants of PHY1361, PHY1363 and PHY1373 cultures was initially investigated by growing the strains in test tubes containing 5 mL P7 medium with 100 µM $PO_4^{-3}$ and Cm (5 µg/mL). Following shaking incubation at 37C for 48 hrs the culture supernatants of the three selected strains were assayed for their ability to release phosphate from phytate as described above. The amount of phosphate released was determined from a standard curve. One phytase unit (FTU) is defined as the activity that releases one µmole of inorganic phosphorus from sodium phytate per minute at 37C. All three strains examined produced significantly more phytase activity (300-400 FTU/L) than the previously described PHY902 mutant (100 FTU/L).

Figure 15:
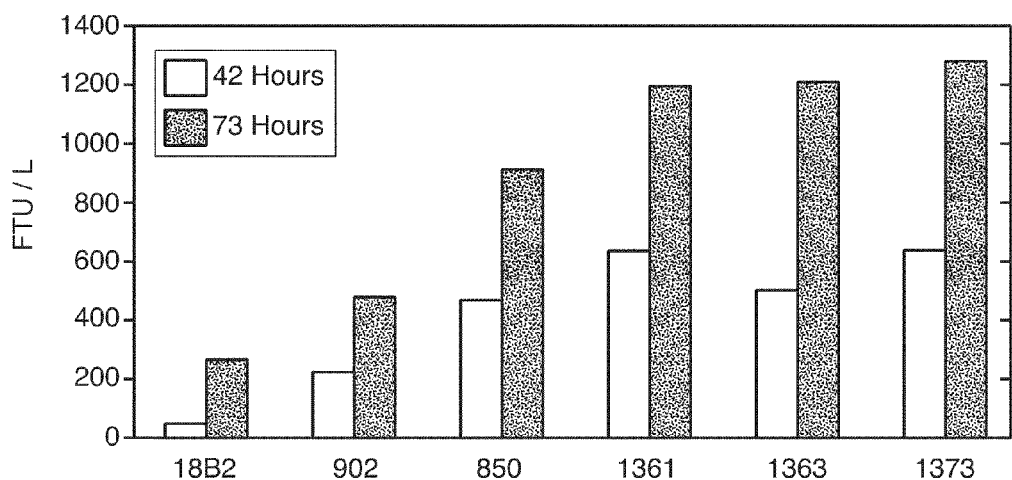
FIG. 15 shows phytase activity in the supernatant of cultures of Bacillus expressing various appA genes. Activity was determined after growth for 42 hours (left bar for each clone) and 73 hours (right bar for each clone). Supernatant samples were removed from the cultures at the indicated time points and tested as described in Example 7A.

Scale up to larger P7 medium cultures (25 mL medium +100 µM $PO_4^{-3}$+Cm [5 µg/mL] in 250 mL baffled shake flasks; incubated with shaking at 200-250 rpm; 37C), however, resulted in the accumulation of surprisingly low levels of phytase activity by all the mutants examined (data not shown). It was subsequently discovered that by using a shaking speed during incubation of approximately 75 rpm, the mutant appA clones accumulated high levels of phytase activity. FIG. 15 shows that after 73 hours of incubation PHY1361, PHY1363, and PHY1373 cultures produced extracellular phytase activity that exceeded 1200 FTU/L. These phytase levels represent a significant improvement over that produced by the parent 18B2 (FIG. 15).

Figure 16:
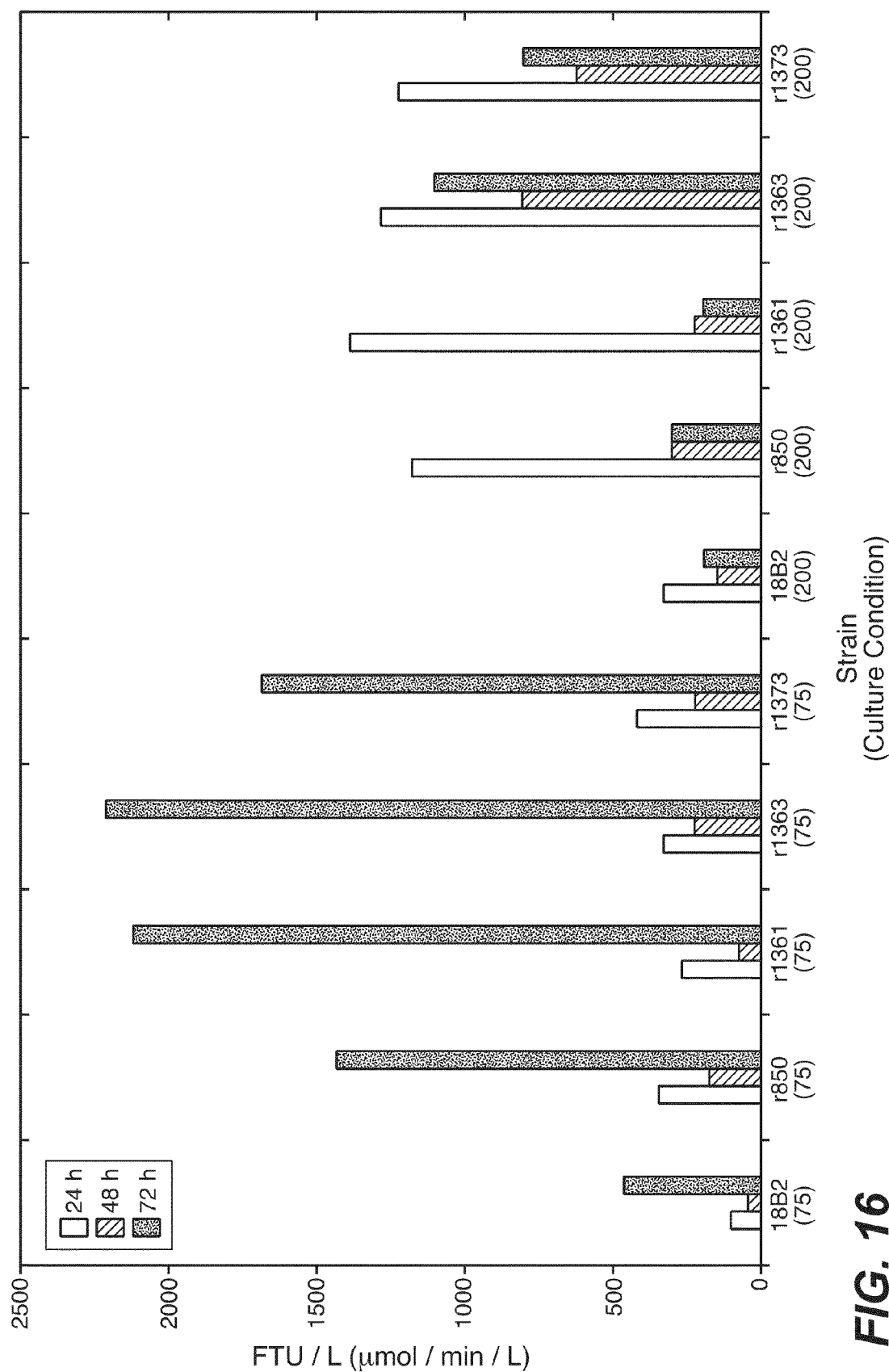
FIG. 16 shows phytase activity in the supernatant of cultures of Bacillus expressing various appA genes and grown under different agitation conditions. Activity was determined after growth for 24, 48 and 72 hours in 25 mL P7 medium containing 100 µM PO$_4$ and 5 µg/mL chloramphenicol and at shaking speeds of either 75 rpm or 200 rpm. Supernatant samples were removed from the cultures at the indicated time points and tested as described in Example 7A. Clones containing mutant appA genes had been transformed with amplification products of the appA gene from cells that had previously been isolated from the mutagenesis library, confirming that the increase phytase activity was related to the appA mutation.

In order to determine if the observed phytase activity improvements were genetically linked to the appA gene, the entire appA gene-containing region of strains PHY1361, PHY1363 and PHY1373 were PCR amplified from the corresponding genomic DNA using Herculase™ polymerase (Stratagene, LaJolla, Calif.) and the resulting 6.9 kb product was used to re-transform B. subtilis OS21.10. Following transformation, single, chloramphenicol-resistant colonies, designated r-PHY1361, r-PHY1363 and r-PHY1373, were chosen for phytase activity analysis. FIG. 16 shows that cultures of r-PHY1361, r-PHY1363 and r-PHY1373, generated under slow shaking conditions, produced phytase activity levels of between 1685 and 2204 FTU/L, representing an almost 5-fold increase over the parent 18B2 (Table 1). This result confirmed the fact that the improved phenotype of the 1300 series mutants was linked to the appA gene loci. It is interesting to note that the identical mutants PHY1363 and PHY1373, both maintained relatively high phytase activities at the higher shaker speed (200 rpm).

14B. Analysis of Phytase Specific Activity and Amount of Production/Secretion

The biochemical basis for the phytase activity improvements observed can be explained either by the production of a phytase enzyme with higher specific activity or through the increased production and/or secretion of the phytase enzyme to the extracellular environment. To distinguish between these two alternatives, the culture supernatants of the retransformed strains were used to perform a quantitative Western blot analysis. Briefly, equivalent volumes of each supernatant were concentrated by TCA precipitation, washed with 80% acetone, dissolved in SDS-PAGE running buffer diluted with sample loading buffer and subjected to SDS-PAGE analysis. Following electrophoresis, the proteins were transferred to a nitrocellulose membrane which was first exposed to a polyclonal rabbit antibody specific for the phytase protein and then a secondary HRP linked antibody to detect the AppA protein. Densitometry was used to measure the relative amount of phytase protein for comparison to the relative phytase activity.

Figure 17:
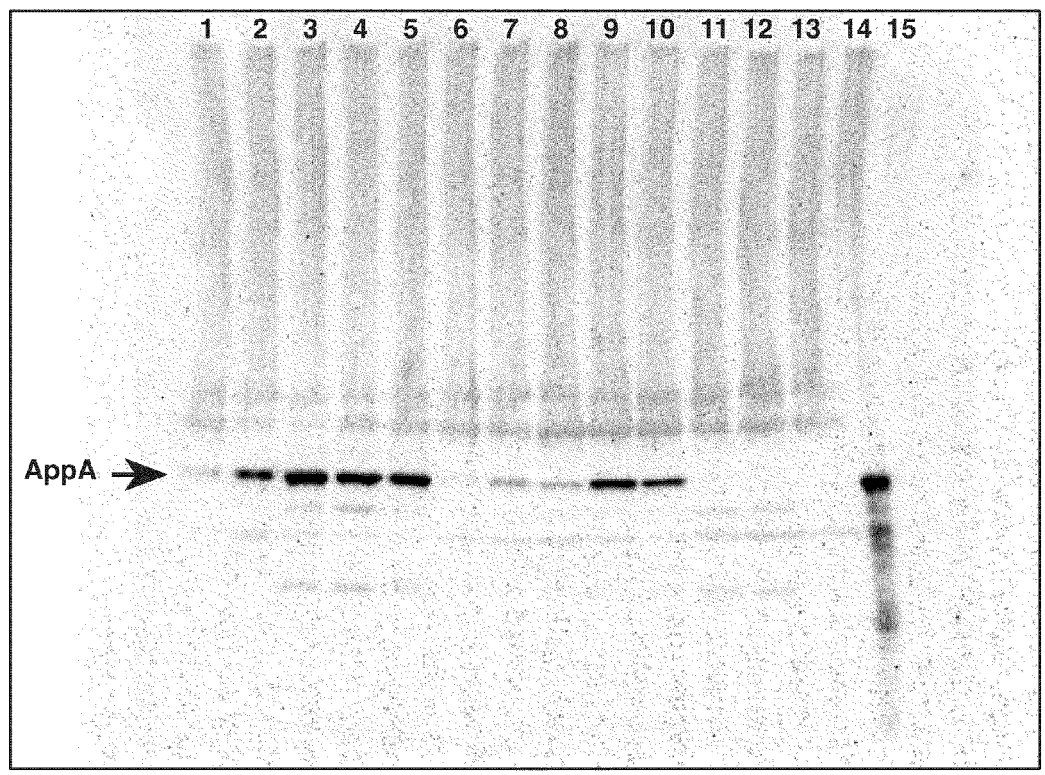
FIG. 17 shows an immunoblot of an SDS-PAGE gel. Analysis was performed on the supernatant from the cultures described in FIG. 16, as well as from several controls, as described in Example 7B. Lane #/culture: 1/18B2 at 75 rpm; 2/R-PHY850 at 75 rpm; 3/R-PHY1361 at 75 rpm, 4/R-PHY1363 at 75 rpm; 5/R-PHY1373 at 75 rpm; 6/18B2 at 200 rpm; 7/R-PHY850 at 200 rpm; 8/R-PHY1361 at 200 rpm; 9/R-PHY1363 at 200 rpm; 10/R-PHY1373 at 200 rpm; 11untransformed Bacillus subtilis strain OS21.10 at 7 rpm; 12/Bacillus subtilis expressing the subtilisin protease gene cassette at 75 rpm; 13/Bacillus subtilis expressing the subtilisin protease gene cassette at 150 rpm; 14/DBT-MO; 15/weight markers. The AppA phytase protein is indicated with an arrow.

The phytase antibody used in this study was specific for the phytase protein. The immunoblot detected a protein consistent with the size of AppA (~45 kD.) in all of the strains containing an appA gene (FIG. 17, lanes 1-10). B. subtilis strains OS21.10 (the expression strain used in this study) and a strain expressing subtilisin protease (a protease gene in the expression locus), both of which lack an appA gene, failed to produce a protein that reacted with the antibody (FIG. 17, lanes 11-13). It is apparent from the results of the Western blot that the increased levels of phytase activity observed in the culture supernatants in all of the mutants examined (FIG. 16) are, at least in part, the direct result of increased levels of AppA protein production/secretion (FIG. 17; Lanes 1-6). Densitometry of these protein bands revealed that the new appA variants produced nearly as much as nine times more phytase protein than the parent 18B2 (Table 1). It is also interesting to note that the identical mutants PHY1363 and PHY1373, both of which maintained relatively high phytase activities at the higher shaker speed (200 rpm; FIG. 4) also maintained higher phytase productivity under these incubation conditions.

14C. Thermostability of AppA Mutants

Thermostability is perhaps the single most important prerequisite for successful application of a phytase in animal feed. To determine if any of the mutations responsible for the increased enzyme production have in any way altered the thermostability profile of the enzyme, the culture supernatants of the retransformed 1300 series strains (Table 1) were assayed for phytase activity after being incubated at elevated temperatures. The supernatants from the cultures were diluted between 1:20 to 1:70 into assay buffer (0.25 M NaOAc, 1 mM $CaCl_2$, pH 4.5), incubated in a water bath at the appropriate temperature for min and then cooled in an ice water bath for 10 min (volume was 1 mL). The samples were divided into two 500 µL amounts and prewarmed to 37C for five minutes. One of each sample was diluted to 1.5 mL by the addition of 37C prewarmed 0.7% sodium phytate (prepared in assay buffer, pH 4.5) and incubated at 37C for 1 h. At the end of 1 h, the sample was further diluted to 2.5 mL by the addition of the standard color reagent and the A415 was recorded. The other half of each sample was diluted to 1.5 mL by the addition of 1 mL standard color reagent and then diluted to 2.5 mL by the addition of 1 mL of 0.7% sodium phytate. The A415 was recorded and subtracted from the A415 for the corresponding reaction and this value was used to calculate the FTU/L. FIG. 18 shows that the thermostability profiles of the new phytase variants was not significantly altered from that of the wild-type AppA protein.

Of course, it should be understood that a wide range of changes and modifications can be made to the preferred embodiment described above. It is therefore intended that the foregoing detailed description be understood in the context of the following claims, including all equivalents, which are intended to define the scope of this invention.

TABLE 1

Analysis of phytase activity and productivity in *B. subtilis*.

|  | 18B2 | r-850 | r-1361 | r-1363 | r-1373 | 18B2 | r-850 | r-1361 | r-1363 | r-1373 |
|---|---|---|---|---|---|---|---|---|---|---|
| Shaking rpm | 75 | 75 | 75 | 75 | 75 | 200 | 200 | 200 | 200 | 200 |
| FTU/L (72 h) | 460 | 1426 | 2118 | 2204 | 1685 | 189 | 299 | 187 | 1103 | 797 |
| Relative activity | 1 | 3.1 | 4.6 | 4.8 | 3.7 | 1 | 1.6 | 1 | 5.9 | 4.3 |
| Densitometry | 16 | 80 | 137 | 122 | 121 | 10 | 27 | 26 | 105 | 74 |
| Relative production | 1 | 5 | 8.6 | 7.6 | 7.6 | 1 | 2.7 | 2.6 | 10.5 | 7.4 |

The invention claimed is:

1. A method of producing a recombinant phytase having modified activity, said method comprising:
   a) subjecting to error-prone amplification a nucleic acid comprising a sequence encoding a polypeptide that is at least 98% identical to SEQ ID No. 2, to produce a product of error-prone amplification;
   b) transforming a host cell with an expression vector comprising the product of error-prone amplification, wherein the host cell is cultured under conditions suitable for said cell to express said product of error-prone amplification, thereby producing the recombinant phytase.

2. The method of claim 1, wherein said host cell is *Bacillus subtilis*.

3. The method of claim 1, further comprising:
   c) recovering said recombinant phytase.

* * * * *

```
                           SEQUENCE LISTING

<160> NUMBER OF SEQ ID NOS: 33

<210> SEQ ID NO 1
<211> LENGTH: 50
<212> TYPE: PRT
<213> ORGANISM: Artificial Sequence
<220> FEATURE:
<223> OTHER INFORMATION: synthetic chimeric protein

<400> SEQUENCE: 1

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Gln Ser
                20                  25                  30

Glu Pro Glu Leu Lys Leu Glu Ser Val Val Ile Val Ser Arg His Gly
            35                  40                  45

Val Arg
    50

<210> SEQ ID NO 2
<211> LENGTH: 440
<212> TYPE: PRT
<213> ORGANISM: Escherichia coli

<400> SEQUENCE: 2

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Gln Ser
                20                  25                  30

Glu Pro Glu Leu Lys Leu Glu Ser Val Val Ile Val Ser Arg His Gly
            35                  40                  45

Val Arg Ala Pro Thr Lys Ala Thr Gln Leu Met Gln Asp Val Thr Pro
    50                  55                  60

Asp Ala Trp Pro Thr Trp Pro Val Lys Leu Gly Trp Leu Thr Pro Arg
65                  70                  75                  80

Gly Gly Glu Leu Ile Ala Tyr Leu Gly His Tyr Gln Arg Gln Arg Leu
                85                  90                  95

Val Ala Asp Gly Leu Leu Ala Lys Lys Gly Cys Pro Gln Ser Gly Gln
            100                 105                 110
```

```
Val Ala Ile Ile Ala Asp Val Asp Glu Arg Thr Arg Lys Thr Gly Glu
            115                 120                 125
Ala Phe Ala Ala Gly Leu Ala Pro Asp Cys Ala Ile Thr Val His Thr
        130                 135                 140
Gln Ala Asp Thr Ser Ser Pro Asp Pro Leu Phe Asn Pro Leu Lys Thr
145                 150                 155                 160
Gly Val Cys Gln Leu Asp Asn Ala Asn Val Thr Asp Ala Ile Leu Ser
                165                 170                 175
Arg Ala Gly Gly Ser Ile Ala Asp Phe Thr Gly His Arg Gln Thr Ala
            180                 185                 190
Phe Arg Glu Leu Glu Arg Val Leu Asn Phe Pro Gln Ser Asn Leu Cys
        195                 200                 205
Leu Lys Arg Glu Lys Gln Asp Glu Ser Cys Ser Leu Thr Gln Ala Leu
210                 215                 220
Pro Ser Glu Leu Lys Val Ser Ala Asp Asn Val Ser Leu Thr Gly Ala
225                 230                 235                 240
Val Ser Leu Ala Ser Met Leu Thr Glu Ile Phe Leu Leu Gln Gln Ala
                245                 250                 255
Gln Gly Met Pro Glu Pro Gly Trp Gly Arg Ile Thr Asp Ser His Gln
            260                 265                 270
Trp Asn Thr Leu Leu Ser Leu His Asn Ala Gln Phe Tyr Leu Leu Gln
        275                 280                 285
Arg Thr Pro Glu Val Ala Arg Ser Arg Ala Thr Pro Leu Leu Asp Leu
290                 295                 300
Ile Lys Thr Ala Leu Thr Pro His Pro Pro Gln Lys Gln Ala Tyr Gly
305                 310                 315                 320
Val Thr Leu Pro Thr Ser Val Leu Phe Ile Ala Gly His Asp Thr Asn
                325                 330                 335
Leu Ala Asn Leu Gly Gly Ala Leu Glu Leu Asn Trp Thr Leu Pro Gly
            340                 345                 350
Gln Pro Asp Asn Thr Pro Pro Gly Gly Glu Leu Val Phe Glu Arg Trp
        355                 360                 365
Arg Arg Leu Ser Asp Asn Ser Gln Trp Ile Gln Val Ser Leu Val Phe
370                 375                 380
Gln Thr Leu Gln Gln Met Arg Asp Lys Thr Pro Leu Ser Leu Asn Thr
385                 390                 395                 400
Pro Pro Gly Glu Val Lys Leu Thr Leu Ala Gly Cys Glu Glu Arg Asn
                405                 410                 415
Ala Gln Gly Met Cys Ser Leu Ala Gly Phe Thr Gln Ile Val Asn Glu
            420                 425                 430
Ala Arg Ile Pro Ala Cys Ser Leu
        435                 440

<210> SEQ ID NO 3
<211> LENGTH: 440
<212> TYPE: PRT
<213> ORGANISM: Artificial Sequence
<220> FEATURE:
<223> OTHER INFORMATION: synthetic mutant AppA PHY679 phytase

<400> SEQUENCE: 3

Val Arg Ser Lys Lys Leu Trp Ile Val Ala Ser Thr Ala Leu Leu Ile
1               5                   10                  15
Ser Val Ala Phe Ser Ser Ser Ile Ala Ser Ala Ala Glu Glu Gln Ser
                20                  25                  30
Glu Pro Glu Leu Lys Leu Glu Ser Val Val Ile Val Ser Arg His Gly
```

```
                35                  40                  45
Val Arg Ala Pro Thr Lys Ala Thr Ala Leu Met Gln Asp Val Thr Pro
 50                  55                  60
Asp Ala Trp Pro Thr Trp Pro Val Lys Leu Gly Trp Leu Thr Pro Arg
 65                  70                  75                  80
Gly Gly Glu Leu Ile Ala Tyr Leu Gly His Tyr Gln Arg Gln Arg Leu
                 85                  90                  95
Val Ala Asp Gly Leu Leu Ala Lys Lys Gly Cys Pro Gln Ser Gly Gln
                100                 105                 110
Val Ala Ile Ile Ala Asp Val Asp Glu Arg Thr Arg Lys Thr Gly Glu
                115                 120                 125
Ala Phe Ala Ala Gly Leu Ala Pro Asp Cys Ala Ile Thr Val Arg Thr
                130                 135                 140
Gln Ala Asp Thr Ser Ser Pro Asp Pro Leu Phe Lys Pro Leu Lys Thr
145                 150                 155                 160
Gly Val Cys Gln Leu Asp Asn Ala Asn Val Thr Asp Ala Ile Leu Ser
                165                 170                 175
Arg Ala Gly Gly Ser Ile Ala Asp Phe Thr Gly His Arg Gln Thr Ala
                180                 185                 190
Phe Arg Glu Leu Glu Arg Val Leu Asn Phe Pro Gln Ser Asn Leu Cys
                195                 200                 205
Leu Lys Arg Glu Lys Gln Asp Glu Ser Cys Ser Leu Thr Gln Ala Leu
210                 215                 220
Pro Ser Glu Leu Lys Val Ser Ala Asp Asn Val Ser Leu Thr Gly Ala
225                 230                 235                 240
Val Ser Leu Ala Ser Met Leu Thr Glu Ile Phe Leu Leu Gln Gln Ala
                245                 250                 255
Gln Pro Met Pro Glu Pro Gly Trp Gly Arg Ile Thr Asp Ser His Gln
                260                 265                 270
Trp Asn Thr Leu Leu Ser Leu His Asn Ala Gln Phe Tyr Leu Leu Gln
                275                 280                 285
Arg Thr Pro Glu Val Ala Arg Ser Arg Ala Thr Pro Leu Leu Asp Leu
                290                 295                 300
Ile Lys Thr Ala Leu Thr Pro His Pro Pro Gln Lys Gln Ala Tyr Gly
305                 310                 315                 320
Val Thr Leu Pro Thr Ser Val Leu Phe Ile Ala Gly His Asp Thr Asn
                325                 330                 335
Leu Ala Asn Leu Gly Gly Ala Leu Glu Leu Asn Trp Thr Leu Pro Gly
                340                 345                 350
Gln Pro Asp Asn Thr Pro Gly Gly Glu Leu Val Phe Glu Arg Trp
                355                 360                 365
Arg Arg Leu Ser Asp Asn Ser Gln Trp Ile Gln Val Ser Leu Val Phe
                370                 375                 380
Gln Thr Leu Gln Gln Met Arg Asp Lys Thr Pro Leu Ser Leu Asn Thr
385                 390                 395                 400
Pro Pro Gly Glu Val Lys Leu Thr Leu Ala Gly Cys Glu Glu Arg Asn
                405                 410                 415
Ala Gln Gly Met Cys Ser Leu Ala Gly Phe Thr Gln Ile Val Asn Glu
                420                 425                 430
Ala Arg Ile Pro Ala Cys Ser Leu
                435                 440

<210> SEQ ID NO 4
<211> LENGTH: 440
```

```
<212> TYPE: PRT
<213> ORGANISM: Artificial Sequence
<220> FEATURE:
<223> OTHER INFORMATION: synthetic mutant AppA PHY735 phytase

<400> SEQUENCE: 4
```

| | | | | | | | | | | | | | | | |
|---|---|---|---|---|---|---|---|---|---|---|---|---|---|---|---|
| Val | Arg | Ser | Lys | Lys | Leu | Trp | Ile | Val | Ala | Ser | Thr | Ala | Leu | Leu | Ile |
| 1 | | | | 5 | | | | | 10 | | | | | 15 | |
| Ser | Val | Ala | Phe | Ser | Ser | Ser | Ile | Ala | Ser | Ala | Ala | Glu | Glu | Gln | Ser |
| | | | 20 | | | | | 25 | | | | | 30 | | |
| Glu | Pro | Glu | Leu | Lys | Leu | Glu | Ser | Val | Ile | Val | Ser | Arg | His | Gly | |
| | | 35 | | | | | 40 | | | | | 45 | | | |
| Val | Arg | Ala | Pro | Thr | Lys | Ala | Thr | Gln | Leu | Met | Gln | Asp | Val | Thr | Pro |
| | 50 | | | | | 55 | | | | | 60 | | | | |
| Asp | Ala | Trp | Pro | Thr | Trp | Pro | Val | Lys | Leu | Gly | Trp | Leu | Thr | Pro | Arg |
| 65 | | | | | 70 | | | | | 75 | | | | | 80 |
| Gly | Gly | Glu | Leu | Ile | Ala | Tyr | Leu | Gly | His | Tyr | Gln | Arg | Gln | Arg | Leu |
| | | | | 85 | | | | | 90 | | | | | 95 | |
| Val | Ala | Asp | Gly | Leu | Leu | Ala | Lys | Lys | Gly | Cys | Pro | Gln | Ser | Gly | Gln |
| | | | 100 | | | | | 105 | | | | | 110 | | |
| Val | Ala | Ile | Ile | Ala | Asp | Val | Asp | Glu | Arg | Thr | Arg | Lys | Thr | Gly | Glu |
| | | 115 | | | | | 120 | | | | | 125 | | | |
| Ala | Phe | Ala | Ala | Gly | Leu | Ala | Pro | Asp | Cys | Ala | Ile | Thr | Val | Arg | Thr |
| | 130 | | | | | 135 | | | | | 140 | | | | |
| Gln | Ala | Asp | Thr | Ser | Ser | Pro | Asp | Pro | Leu | Phe | Asn | Pro | Leu | Lys | Thr |
| 145 | | | | | 150 | | | | | 155 | | | | | 160 |
| Gly | Val | Cys | Gln | Leu | Asp | Asn | Ala | Asn | Val | Thr | Asp | Ala | Ile | Leu | Ser |
| | | | | 165 | | | | | 170 | | | | | 175 | |
| Arg | Ala | Gly | Gly | Ser | Ile | Ala | Asp | Phe | Thr | Gly | His | Arg | Gln | Thr | Ala |
| | | | 180 | | | | | 185 | | | | | 190 | | |
| Phe | Arg | Glu | Leu | Glu | Arg | Val | Leu | Asn | Phe | Pro | Gln | Ser | Asn | Leu | Cys |
| | | 195 | | | | | 200 | | | | | 205 | | | |
| Leu | Lys | Arg | Glu | Lys | Gln | Asp | Glu | Ser | Cys | Ser | Leu | Thr | Gln | Ala | Leu |
| | 210 | | | | | 215 | | | | | 220 | | | | |
| Pro | Ser | Glu | Leu | Lys | Val | Ser | Ala | Asp | Asn | Val | Ser | Leu | Thr | Gly | Ala |
| 225 | | | | | 230 | | | | | 235 | | | | | 240 |
| Val | Ser | Leu | Ala | Ser | Met | Leu | Thr | Glu | Ile | Phe | Leu | Leu | Gln | Gln | Ala |
| | | | | 245 | | | | | 250 | | | | | 255 | |
| Gln | Gly | Met | Pro | Glu | Pro | Gly | Trp | Gly | Arg | Ile | Thr | Asp | Ser | His | Gln |
| | | | 260 | | | | | 265 | | | | | 270 | | |
| Trp | Asn | Thr | Leu | Leu | Ser | Leu | His | Asn | Ala | Gln | Phe | Tyr | Leu | Leu | Gln |
| | | 275 | | | | | 280 | | | | | 285 | | | |
| Arg | Thr | Pro | Glu | Val | Ala | Arg | Ser | Arg | Ala | Thr | Pro | Leu | Leu | Asp | Leu |
| | 290 | | | | | 295 | | | | | 300 | | | | |
| Ile | Lys | Thr | Ala | Leu | Thr | Pro | His | Pro | Pro | Gln | Lys | Gln | Ala | Tyr | Gly |
| 305 | | | | | 310 | | | | | 315 | | | | | 320 |
| Val | Thr | Leu | Pro | Thr | Ser | Val | Leu | Phe | Ile | Ala | Gly | His | Asp | Thr | Asn |
| | | | | 325 | | | | | 330 | | | | | 335 | |
| Leu | Ala | Asn | Leu | Gly | Gly | Ala | Leu | Glu | Leu | Asn | Trp | Thr | Leu | Pro | Gly |
| | | | 340 | | | | | 345 | | | | | 350 | | |
| Gln | Pro | Asp | Asn | Thr | Pro | Gly | Gly | Glu | Leu | Val | Phe | Glu | Arg | Trp | |
| | | 355 | | | | | 360 | | | | | 365 | | | |
| Arg | Arg | Leu | Ser | Asp | Asn | Ser | Gln | Trp | Ile | Gln | Val | Ser | Leu | Val | Phe |
| | 370 | | | | | 375 | | | | | 380 | | | | |
| Gln | Thr | Leu | Gln | Gln | Met | Arg | Asp | Lys | Thr | Pro | Leu | Ser | Leu | Asn | Thr |

```
                385                 390                 395                 400
Pro Pro Gly Glu Val Lys Leu Thr Leu Ala Gly Cys Glu Glu Arg Asn
                    405                 410                 415

Ala Gln Gly Met Cys Ser Leu Ala Gly Phe Thr Gln Ile Val Asn Glu
                    420                 425                 430

Ala Arg Ile Pro Ala Cys Ser Leu
                    435                 440

<210> SEQ ID NO 5
<211> LENGTH: 440
<212> TYPE: PRT
<213> ORGANISM: Artificial Sequence
<220> FEATURE:
<223> OTHER INFORMATION: synthetic mutant AppA PHY736 phytase

<400> SEQUENCE: 5

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Glu Glu Gln Ser
                20                  25                  30

Glu Pro Glu Leu Lys Leu Glu Ser Val Val Ile Val Ser Arg His Gly
            35                  40                  45

Val Arg Ala Pro Thr Lys Ala Thr Gln Leu Met Gln Asp Val Thr Pro
50                  55                  60

Asp Ala Trp Pro Thr Trp Pro Val Lys Leu Gly Arg Leu Thr Pro Arg
65                  70                  75                  80

Gly Gly Glu Leu Ile Ala Tyr Leu Gly His Tyr Gln Arg Gln Arg Leu
                85                  90                  95

Val Ala Asp Gly Leu Leu Val Lys Lys Gly Cys Pro Gln Ser Gly Gln
            100                 105                 110

Val Ala Ile Ile Ala Asp Val Asp Glu Arg Thr Arg Lys Thr Gly Glu
        115                 120                 125

Ala Phe Ala Ala Gly Leu Ala Pro Asp Cys Ala Ile Thr Val Arg Thr
    130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
                165                 170                 175

Arg Ala Gly Gly Ser Ile Ala Asp Phe Thr Gly His Arg Gln Thr Ala
            180                 185                 190

Phe Arg Glu Leu Glu Arg Val Leu Asn Phe Pro Gln Ser Asn Leu Cys
        195                 200                 205

Leu Lys Arg Glu Lys Gln Asp Glu Ser Cys Ser Leu Thr Gln Ala Leu
    210                 215                 220

Pro Ser Glu Leu Lys Val Ser Ala Asp Asn Val Ser Leu Thr Gly Ala
225                 230                 235                 240

Val Ser Leu Ala Ser Met Leu Thr Glu Ile Phe Leu Leu Gln Gln Ala
                245                 250                 255

Gln Gly Met Pro Glu Pro Gly Trp Gly Arg Ile Thr Asp Ser His Gln
            260                 265                 270

Trp Asn Thr Leu Leu Ser Leu His Asn Ala Gln Phe Tyr Leu Leu Gln
        275                 280                 285

Arg Thr Pro Glu Val Ala Arg Ser Arg Ala Thr Pro Leu Leu Asp Leu
    290                 295                 300

Ile Lys Thr Ala Leu Thr Pro His Pro Pro Gln Lys Gln Ala Tyr Gly
305                 310                 315                 320
```

Val Thr Leu Pro Thr Ser Val Leu Phe Ile Ala Gly His Asp Thr Asn
            325                 330                 335

Leu Ala Asn Leu Gly Gly Ala Leu Glu Leu Asn Trp Thr Leu Pro Gly
            340                 345                 350

Gln Pro Asp Asn Thr Pro Pro Gly Gly Glu Leu Val Phe Glu Arg Trp
            355                 360                 365

Arg Arg Leu Ser Asp Asn Ser Gln Trp Ile Gln Val Ser Leu Val Phe
370                 375                 380

Gln Thr Leu Gln Gln Met Arg Asp Lys Thr Pro Leu Ser Leu Asn Thr
385                 390                 395                 400

Pro Pro Gly Glu Val Lys Leu Thr Leu Ala Gly Cys Glu Glu Arg Asn
            405                 410                 415

Ala Gln Gly Met Cys Ser Leu Ala Gly Phe Thr Gln Val Asn Glu
            420                 425                 430

Ala Arg Ile Pro Ala Cys Ser Leu
            435                 440

<210> SEQ ID NO 6
<211> LENGTH: 440
<212> TYPE: PRT
<213> ORGANISM: Artificial Sequence
<220> FEATURE:
<223> OTHER INFORMATION: synthetic mutant AppA PHY846 phytase

<400> SEQUENCE: 6

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Glu Glu Gln Ser
            20                  25                  30

Glu Pro Glu Leu Lys Leu Glu Ser Val Val Ile Val Ser Arg His Gly
            35                  40                  45

Val Arg Ala Pro Thr Lys Ala Thr Gln Leu Met Gln Asp Val Thr Pro
50                  55                  60

Asp Ala Trp Pro Thr Trp Pro Val Lys Leu Gly Trp Leu Thr Pro Arg
65                  70                  75                  80

Gly Gly Glu Leu Ile Ala Tyr Leu Gly His Tyr Gln Arg Gln Arg Leu
            85                  90                  95

Val Ala Asp Gly Leu Leu Ala Lys Lys Gly Cys Pro Gln Ser Gly Gln
            100                 105                 110

Val Ala Ile Ile Ala Asp Val Asp Glu Arg Thr Arg Lys Thr Gly Glu
            115                 120                 125

Ala Phe Ala Ala Gly Leu Ala Pro Asp Cys Ala Ile Thr Val Arg Thr
            130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
            165                 170                 175

Arg Ala Gly Gly Ser Ile Ala Asp Phe Thr Gly His Arg Gln Thr Ala
            180                 185                 190

Phe Arg Glu Leu Glu Arg Val Leu Asn Phe Pro Gln Ser Asn Leu Cys
            195                 200                 205

Leu Lys Arg Glu Lys Arg Asp Glu Ser Cys Ser Leu Thr Gln Ala Leu
            210                 215                 220

Pro Ser Glu Leu Lys Val Ser Ala Asp Asn Val Ser Leu Thr Gly Ala
225                 230                 235                 240

```
Val Ser Leu Ala Ser Met Leu Thr Glu Ile Phe Leu Leu Gln Gln Ala
                245                 250                 255

Gln Gly Met Pro Glu Pro Gly Trp Gly Arg Ile Thr Asp Ser His Gln
            260                 265                 270

Trp Asn Thr Leu Leu Ser Leu His Asn Ala Gln Phe Tyr Leu Leu Gln
        275                 280                 285

Arg Thr Pro Glu Val Ala Arg Ser Arg Ala Thr Pro Leu Leu Asp Leu
    290                 295                 300

Ile Lys Thr Ala Leu Thr Pro His Pro Pro Gln Lys Gln Ala Tyr Gly
305                 310                 315                 320

Val Thr Leu Pro Thr Ser Val Leu Phe Ile Ala Gly His Asp Thr Asn
                325                 330                 335

Leu Ala Asn Leu Gly Gly Ala Leu Glu Leu Asn Trp Thr Leu Pro Gly
            340                 345                 350

Gln Pro Asp Asn Thr Pro Gly Gly Glu Leu Val Phe Glu Arg Trp
        355                 360                 365

Arg Arg Leu Ser Asp Asn Ser Gln Trp Ile Gln Val Ser Leu Val Phe
    370                 375                 380

Gln Thr Leu Gln Gln Met Arg Asp Lys Thr Pro Leu Ser Leu Asn Thr
385                 390                 395                 400

Pro Pro Gly Glu Val Lys Leu Thr Leu Ala Gly Cys Glu Glu Arg Asn
                405                 410                 415

Ala Gln Gly Met Cys Ser Leu Ala Gly Phe Thr Gln Ile Val Asn Glu
            420                 425                 430

Ala Arg Ile Pro Ala Cys Ser Leu
        435                 440

<210> SEQ ID NO 7
<211> LENGTH: 440
<212> TYPE: PRT
<213> ORGANISM: Artificial Sequence
<220> FEATURE:
<223> OTHER INFORMATION: synthetic mutant AppA PHY850 phytase

<400> SEQUENCE: 7

Val Arg Ser Lys Lys Leu Trp Ile Val Ala Leu Thr Ala Leu Leu Ile
1               5                   10                  15

Ser Val Ala Phe Ser Ser Ile Ala Ser Ala Glu Glu Gln Ser
            20                  25                  30

Glu Pro Glu Leu Lys Leu Glu Ser Val Val Ile Val Ser Arg His Gly
        35                  40                  45

Val Arg Ala Pro Thr Lys Ala Thr Gln Leu Met Gln Asp Val Thr Pro
    50                  55                  60

Asp Ala Trp Pro Thr Trp Pro Val Lys Leu Gly Trp Leu Thr Pro Arg
65                  70                  75                  80

Gly Gly Glu Leu Ile Ala Tyr Leu Gly His Tyr Gln Arg Gln Arg Leu
                85                  90                  95

Val Ala Asp Gly Leu Leu Ala Lys Lys Gly Cys Pro Gln Ser Gly Gln
            100                 105                 110

Val Ala Ile Ile Ala Asp Val Asp Glu Arg Thr Arg Lys Thr Gly Glu
        115                 120                 125

Ala Phe Ala Ala Gly Leu Ala Pro Asp Cys Ala Ile Thr Val Arg Thr
    130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
```

```
                    165                 170                 175
Arg Ala Gly Gly Ser Ile Ala Asp Phe Thr Gly His Arg Gln Thr Ala
            180                 185                 190
Phe Arg Glu Leu Glu Arg Val Leu Asn Phe Pro Gln Ser Asn Leu Cys
        195                 200                 205
Leu Lys Arg Glu Lys Gln Asp Glu Ser Cys Ser Leu Thr Gln Ala Leu
    210                 215                 220
Pro Ser Glu Leu Lys Val Ser Ala Asp Asn Val Ser Leu Thr Gly Ala
225                 230                 235                 240
Val Ser Leu Ala Ser Met Leu Thr Glu Ile Phe Leu Leu Gln Gln Ala
                245                 250                 255
Gln Gly Met Pro Glu Pro Gly Trp Gly Arg Ile Thr Asp Ser His Gln
            260                 265                 270
Trp Asn Thr Leu Leu Ser Leu His Asn Ala Gln Phe Tyr Leu Leu Gln
        275                 280                 285
Arg Thr Pro Glu Val Ala Arg Ser Arg Ala Thr Pro Leu Leu Asp Leu
    290                 295                 300
Ile Lys Thr Ala Leu Thr Pro His Pro Pro Gln Lys Gln Ala Tyr Gly
305                 310                 315                 320
Val Thr Leu Pro Thr Ser Val Leu Phe Ile Ala Gly His Asp Thr Asn
                325                 330                 335
Leu Ala Asn Leu Gly Gly Ala Leu Glu Leu Asn Trp Thr Leu Pro Gly
            340                 345                 350
Gln Pro Asp Asn Thr Pro Gly Gly Glu Leu Val Phe Glu Arg Trp
        355                 360                 365
Arg Arg Leu Ser Asp Asn Ser Gln Trp Ile Gln Val Ser Leu Val Phe
    370                 375                 380
Gln Thr Leu Gln Gln Met Arg Asp Lys Thr Pro Leu Ser Leu Asn Thr
385                 390                 395                 400
Pro Pro Gly Glu Val Lys Leu Thr Leu Ala Gly Cys Glu Glu Arg Asn
                405                 410                 415
Ala Gln Gly Met Cys Ser Leu Ala Gly Phe Thr Gln Ile Val Asn Glu
            420                 425                 430
Ala Arg Ile Pro Ala Cys Ser Leu
        435                 440

<210> SEQ ID NO 8
<211> LENGTH: 440
<212> TYPE: PRT
<213> ORGANISM: Artificial Sequence
<220> FEATURE:
<223> OTHER INFORMATION: synthetic mutant AppA PHY902 phytase

<400> SEQUENCE: 8

Val Arg Ser Lys Lys Leu Trp Ile Val Ala Ser Thr Ala Leu Leu Ile
1               5                   10                  15
Ser Val Ala Phe Ser Ser Ser Ile Ala Ser Ala Ala Glu Glu Gln Ser
                20                  25                  30
Glu Pro Glu Leu Lys Leu Glu Ser Val Val Ile Val Ser Arg His Gly
            35                  40                  45
Val Arg Ala Pro Thr Lys Ala Thr Gln Leu Met Gln Asp Val Thr Pro
    50                  55                  60
Asp Ala Trp Pro Thr Trp Pro Val Lys Leu Gly Trp Leu Thr Pro Arg
65                  70                  75                  80
Gly Gly Glu Leu Ile Ala Tyr Leu Gly His Tyr Gln Arg Gln Arg Leu
                85                  90                  95
```

Val Ala Asp Gly Leu Leu Ala Lys Lys Gly Cys Pro Gln Ser Gly Gln
            100                 105                 110

Val Ala Ile Ile Ala Asp Val Asp Glu Arg Thr Arg Lys Thr Gly Glu
            115                 120                 125

Ala Phe Ala Ala Gly Leu Ala Pro Asp Cys Ala Ile Thr Val Arg Thr
        130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
                165                 170                 175

Arg Ala Gly Gly Ser Ile Ala Asp Phe Thr Gly His Arg Gln Thr Ala
                180                 185                 190

Phe Arg Glu Leu Glu Arg Val Leu Asn Phe Pro Gln Ser Asn Leu Cys
        195                 200                 205

Leu Lys Arg Glu Lys Gln Asp Glu Ser Cys Ser Leu Thr Gln Ala Leu
        210                 215                 220

Pro Ser Glu Leu Lys Val Ser Ala Asp Asn Val Ser Leu Thr Gly Ala
225                 230                 235                 240

Val Ser Leu Ala Ser Met Leu Thr Glu Ile Phe Leu Leu Gln Gln Ala
                245                 250                 255

Gln Gly Met Pro Glu Pro Gly Trp Gly Arg Ile Thr Asp Ser His Gln
            260                 265                 270

Trp Asn Thr Leu Leu Ser Leu His Asn Ala Gln Phe Tyr Leu Leu Gln
        275                 280                 285

Arg Thr Pro Glu Val Ala Arg Ser Arg Ala Thr Pro Leu Leu Asp Leu
        290                 295                 300

Ile Lys Thr Ala Leu Thr Pro His Pro Gln Lys Gln Ala Tyr Gly
305                 310                 315                 320

Val Thr Leu Pro Thr Ser Val Leu Phe Ile Ala Gly His Asp Thr Asn
                325                 330                 335

Leu Ala Asn Leu Gly Gly Ala Leu Glu Leu Asn Trp Thr Leu Pro Gly
            340                 345                 350

Gln Pro Asp Asn Thr Pro Pro Gly Gly Glu Leu Val Phe Glu Arg Trp
        355                 360                 365

Arg Arg Leu Ser Asp Asn Ser Gln Trp Ile Gln Val Ser Leu Val Phe
        370                 375                 380

Gln Thr Leu Gln Gln Met Arg Asp Lys Thr Pro Leu Ser Leu Asn Thr
385                 390                 395                 400

Pro Pro Gly Glu Val Lys Leu Thr Leu Ala Gly Cys Glu Glu Arg Asn
                405                 410                 415

Ala Gln Gly Met Cys Ser Leu Ala Gly Phe Thr Gln Ile Val Asn Glu
            420                 425                 430

Ala Arg Ile Pro Ala Cys Ser Leu
        435                 440

<210> SEQ ID NO 9
<211> LENGTH: 440
<212> TYPE: PRT
<213> ORGANISM: Artificial Sequence
<220> FEATURE:
<223> OTHER INFORMATION: synthetic mutant AppA PHY850 phytase

<400> SEQUENCE: 9

Val Arg Ser Lys Lys Leu Trp Ile Val Ala Leu Thr Ala Leu Leu Ile
1               5                   10                  15

-continued

Ser Val Ala Phe Ser Ser Ile Ala Ser Ala Ala Glu Glu Gln Ser
        20              25              30

Glu Pro Glu Leu Lys Leu Glu Ser Val Val Ile Val Ser Arg His Gly
            35              40              45

Val Arg Ala Pro Thr Lys Ala Thr Gln Leu Met Gln Asp Val Thr Pro
50              55              60

Asp Ala Trp Pro Thr Trp Pro Val Lys Leu Gly Trp Leu Thr Pro Arg
65              70              75              80

Gly Gly Glu Leu Ile Ala Tyr Leu Gly His Tyr Gln Arg Gln Arg Leu
                85              90              95

Val Ala Asp Gly Leu Leu Ala Lys Lys Gly Cys Pro Gln Ser Gly Gln
            100             105             110

Val Ala Ile Ile Ala Asp Val Asp Glu Arg Thr Arg Lys Thr Gly Glu
            115             120             125

Ala Phe Ala Ala Gly Leu Ala Pro Asp Cys Ala Ile Thr Val Arg Thr
        130             135             140

Gln Ala Asp Thr Ser Ser Pro Asp Pro Leu Phe Asn Pro Leu Lys Thr
145             150             155             160

Gly Val Cys Gln Leu Asp Asn Ala Asn Val Thr Asp Ala Ile Leu Ser
                165             170             175

Arg Ala Gly Gly Ser Ile Ala Asp Phe Thr Gly His Arg Gln Thr Ala
            180             185             190

Phe Arg Glu Leu Glu Arg Val Leu Asn Phe Pro Gln Ser Asn Leu Cys
        195             200             205

Leu Lys Arg Glu Lys Gln Asp Glu Ser Cys Ser Leu Thr Gln Ala Leu
210             215             220

Pro Ser Glu Leu Lys Val Ser Ala Asp Asn Val Ser Leu Thr Gly Ala
225             230             235             240

Val Ser Leu Ala Ser Met Leu Thr Glu Ile Phe Leu Leu Gln Gln Ala
                245             250             255

Gln Gly Met Pro Glu Pro Gly Trp Gly Arg Ile Thr Asp Ser His Gln
            260             265             270

Trp Asn Thr Leu Leu Ser Leu His Asn Ala Gln Phe Tyr Leu Leu Gln
        275             280             285

Arg Thr Pro Glu Val Ala Arg Ser Arg Ala Thr Pro Leu Leu Asp Leu
290             295             300

Ile Lys Thr Ala Leu Thr Pro His Pro Pro Gln Lys Gln Ala Tyr Gly
305             310             315             320

Val Thr Leu Pro Thr Ser Val Leu Phe Ile Ala Gly His Asp Thr Asn
                325             330             335

Leu Ala Asn Leu Gly Gly Ala Leu Glu Leu Asn Trp Thr Leu Pro Gly
            340             345             350

Gln Pro Asp Asn Thr Pro Pro Gly Gly Glu Leu Val Phe Glu Arg Trp
        355             360             365

Arg Arg Leu Ser Asp Asn Ser Gln Trp Ile Gln Val Ser Leu Val Phe
370             375             380

Gln Thr Leu Gln Gln Met Arg Asp Lys Thr Pro Leu Ser Leu Asn Thr
385             390             395             400

Pro Pro Gly Glu Val Lys Leu Thr Leu Ala Gly Cys Glu Glu Arg Asn
                405             410             415

Ala Gln Gly Met Cys Ser Leu Ala Gly Phe Thr Gln Ile Val Asn Glu
            420             425             430

Ala Arg Ile Pro Ala Cys Ser Leu
        435             440

<210> SEQ ID NO 10
<211> LENGTH: 440
<212> TYPE: PRT
<213> ORGANISM: Artificial Sequence
<220> FEATURE:
<223> OTHER INFORMATION: synthetic mutant AppA PHY1361 phytase

<400> SEQUENCE: 10

```
Val Arg Ser Lys Lys Leu Trp Ile Val Ala Leu Thr Ala Leu Leu Ile
 1               5                  10                  15

Ser Val Ala Phe Ser Ser Ser Ile Ala Ser Ala Glu Glu Gln Ser
            20                  25                  30

Glu Pro Glu Leu Lys Leu Glu Ser Val Val Ile Val Ser Arg His Gly
        35                  40                  45

Val Arg Ala Pro Thr Lys Ala Thr Gln Leu Met Gln Asp Val Thr Pro
50                  55                  60

Asp Ala Trp Pro Thr Trp Pro Val Glu Leu Gly Trp Leu Thr Pro Arg
65                  70                  75                  80

Gly Gly Glu Leu Ile Ala Tyr Leu Gly His Tyr Gln Arg Gln Arg Leu
                85                  90                  95

Val Ala Asp Gly Leu Leu Ala Lys Lys Gly Cys Pro Gln Ser Gly Gln
            100                 105                 110

Val Ala Ile Ile Ala Asp Val Asp Glu Arg Thr Arg Lys Thr Gly Glu
        115                 120                 125

Ala Phe Ala Ala Gly Leu Ala Pro Asp Cys Ala Ile Thr Val Arg Thr
    130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
                165                 170                 175

Arg Ala Gly Gly Ser Ile Ala Asp Phe Thr Gly His Arg Gln Thr Ala
            180                 185                 190

Phe Arg Glu Leu Glu Arg Val Leu Asn Phe Pro Gln Ser Asn Leu Cys
        195                 200                 205

Leu Lys Arg Glu Lys Gln Asp Glu Ser Cys Ser Leu Thr Gln Ala Leu
    210                 215                 220

Pro Ser Glu Leu Lys Val Ser Ala Asp Asn Val Ser Leu Thr Gly Ala
225                 230                 235                 240

Val Ser Leu Ala Ser Met Leu Thr Glu Ile Phe Leu Leu Gln Gln Ala
                245                 250                 255

Gln Gly Met Pro Glu Pro Gly Trp Gly Arg Ile Thr Asp Ser His Gln
            260                 265                 270

Trp Asn Thr Leu Leu Ser Leu His Asn Ala Gln Phe Tyr Leu Leu Gln
        275                 280                 285

Arg Thr Pro Glu Val Ala Arg Ser Arg Ala Thr Pro Leu Leu Asp Leu
    290                 295                 300

Ile Lys Thr Ala Leu Thr Pro His Pro Pro Gln Lys Gln Ala Tyr Gly
305                 310                 315                 320

Val Thr Leu Pro Thr Ser Val Leu Phe Ile Ala Gly His Asp Thr Asn
                325                 330                 335

Leu Ala Asn Leu Gly Gly Ala Leu Glu Leu Asn Trp Thr Leu Pro Gly
            340                 345                 350

Gln Pro Asp Asn Thr Pro Pro Gly Gly Glu Leu Val Phe Glu Arg Trp
        355                 360                 365
```

-continued

Arg Arg Leu Ser Asp Asn Ser Gln Trp Ile Gln Val Ser Leu Val Phe
        370                 375                 380

Gln Thr Leu Gln Gln Met Arg Asp Lys Thr Pro Leu Ser Leu Asn Thr
385                 390                 395                 400

Pro Pro Gly Glu Val Lys Leu Thr Leu Ala Gly Cys Glu Asp Arg Asn
                405                 410                 415

Ala Gln Gly Met Cys Ser Leu Ala Gly Phe Thr Gln Ile Val Asn Glu
            420                 425                 430

Ala Arg Ile Pro Ala Cys Ser Ser
        435                 440

<210> SEQ ID NO 11
<211> LENGTH: 440
<212> TYPE: PRT
<213> ORGANISM: Artificial Sequence
<220> FEATURE:
<223> OTHER INFORMATION: synthetic mutant AppA PHY1363 phytase

<400> SEQUENCE: 11

Val Arg Ser Lys Lys Leu Trp Ile Val Ala Leu Thr Ala Leu Leu Ile
1               5                   10                  15

Ser Val Ala Phe Ser Ser Ile Ala Ser Ala Ala Glu Glu Gln Ser
            20                  25                  30

Glu Pro Glu Leu Lys Leu Glu Ser Val Val Ile Val Ser Arg His Gly
        35                  40                  45

Val Arg Ala Pro Thr Lys Ala Thr Gln Leu Met Gln Asp Val Thr Pro
    50                  55                  60

Asp Ala Trp Pro Thr Trp Pro Val Lys Leu Gly Trp Leu Thr Pro Arg
65                  70                  75                  80

Gly Gly Glu Val Ile Ala Tyr Leu Gly His Tyr Gln Arg Gln Arg Leu
                85                  90                  95

Val Ala Asp Gly Leu Leu Ala Lys Lys Gly Cys Pro Gln Ser Gly Gln
            100                 105                 110

Val Ala Ile Ile Ala Asp Val Asp Glu Arg Thr Arg Lys Thr Gly Glu
        115                 120                 125

Ala Phe Ala Ala Gly Leu Ala Pro Asp Cys Ala Ile Thr Val Arg Thr
    130                 135                 140

Gln Ala Asp Thr Ser Ser Pro Asp Pro Leu Phe Asn Pro Leu Lys Thr
145                 150                 155                 160

Gly Val Cys Gln Leu Asp Asn Ala Asn Val Thr Asp Ala Ile Leu Ser
                165                 170                 175

Arg Ala Gly Gly Ser Ile Ala Asp Phe Thr Gly His Arg Gln Thr Ala
            180                 185                 190

Phe Arg Glu Leu Glu Arg Val Leu Asn Phe Pro Gln Ser Asn Leu Cys
        195                 200                 205

Leu Lys Arg Glu Lys Gln Asp Glu Ser Cys Ser Leu Thr Gln Ala Leu
    210                 215                 220

Pro Ser Glu Leu Lys Val Ser Ala Asp Asn Val Ser Leu Thr Gly Ala
225                 230                 235                 240

Val Ser Leu Ala Ser Met Leu Thr Glu Ile Phe Leu Leu Gln Gln Ala
                245                 250                 255

Gln Gly Met Pro Glu Pro Gly Trp Gly Arg Ile Thr Asp Ser His Gln
            260                 265                 270

Trp Asn Thr Leu Leu Ser Leu His Asn Ala Gln Phe Tyr Leu Leu Gln
        275                 280                 285

Arg Thr Pro Glu Val Ala Arg Ser Arg Ala Thr Pro Leu Leu Asp Leu

```
                290                 295                 300
Ile Lys Thr Ala Leu Thr Pro His Pro Pro Gln Lys Gln Ala Tyr Gly
305                 310                 315                 320

Val Thr Leu Pro Thr Ser Val Leu Phe Ile Ala Gly His Asp Thr Asn
                325                 330                 335

Leu Ala Asn Leu Gly Gly Ala Leu Glu Leu Asn Trp Thr Leu Pro Gly
                340                 345                 350

Gln Pro Asp Asn Thr Pro Pro Gly Gly Glu Leu Val Phe Glu Arg Trp
                355                 360                 365

Arg Arg Leu Ser Asp Asn Ser Gln Trp Ile Gln Val Ser Leu Val Phe
370                 375                 380

Gln Thr Leu Gln Gln Met Arg Asp Lys Thr Pro Leu Ser Leu Asn Thr
385                 390                 395                 400

Pro Pro Gly Glu Val Lys Leu Thr Leu Ala Gly Cys Glu Val Arg Asn
                405                 410                 415

Ala Gln Gly Met Cys Ser Leu Ala Gly Phe Thr Gln Ile Val Asn Glu
                420                 425                 430

Ala Arg Ile Pro Ala Cys Ser Leu
        435                 440

<210> SEQ ID NO 12
<211> LENGTH: 17
<212> TYPE: DNA
<213> ORGANISM: Artificial Sequence
<220> FEATURE:
<223> OTHER INFORMATION: synthetic mutant AppA3F

<400> SEQUENCE: 12
atgaaagcga tcttaat                                                    17

<210> SEQ ID NO 13
<211> LENGTH: 20
<212> TYPE: DNA
<213> ORGANISM: Artificial Sequence
<220> FEATURE:
<223> OTHER INFORMATION: synthetic mutant AppA5F

<400> SEQUENCE: 13
cgtcatggtg tgcgtgctcc                                                 20

<210> SEQ ID NO 14
<211> LENGTH: 16
<212> TYPE: DNA
<213> ORGANISM: Artificial Sequence
<220> FEATURE:
<223> OTHER INFORMATION: synthetic mutant AppGF

<400> SEQUENCE: 14
cgccagaggt tgcccg                                                     16

<210> SEQ ID NO 15
<211> LENGTH: 18
<212> TYPE: DNA
<213> ORGANISM: Artificial Sequence
<220> FEATURE:
<223> OTHER INFORMATION: synthetic mutant AppA/CR

<400> SEQUENCE: 15
gcggctggca acctctgg                                                   18

<210> SEQ ID NO 16
<211> LENGTH: 37
```

-continued

```
<212> TYPE: DNA
<213> ORGANISM: Artificial Sequence
<220> FEATURE:
<223> OTHER INFORMATION: synthetic mutant AppA4R

<400> SEQUENCE: 16
ttacaaactg cacgccggta tgcgtgcgtg cttcatt                              37

<210> SEQ ID NO 17
<211> LENGTH: 432
<212> TYPE: PRT
<213> ORGANISM: Escherichia coli

<400> SEQUENCE: 17
```

| | | | | | | | | | | | | | | |
|---|---|---|---|---|---|---|---|---|---|---|---|---|---|---|
| Met | Lys | Ala | Ile | Leu | Ile | Pro | Phe | Leu | Ser | Leu | Leu | Ile | Pro | Leu | Thr |
| 1 | | | | 5 | | | | | 10 | | | | | 15 | |

| Pro | Gln | Ser | Ala | Phe | Ala | Gln | Ser | Glu | Pro | Glu | Leu | Lys | Leu | Glu | Ser |
|---|---|---|---|---|---|---|---|---|---|---|---|---|---|---|---|
| | | | 20 | | | | 25 | | | | | 30 | | | |

| Val | Val | Ile | Val | Ser | Arg | His | Gly | Val | Arg | Ala | Pro | Thr | Lys | Ala | Thr |
|---|---|---|---|---|---|---|---|---|---|---|---|---|---|---|---|
| | | 35 | | | | | 40 | | | | | 45 | | | |

| Gln | Leu | Met | Gln | Asp | Val | Thr | Pro | Asp | Ala | Trp | Pro | Thr | Trp | Pro | Val |
|---|---|---|---|---|---|---|---|---|---|---|---|---|---|---|---|
| | 50 | | | | | 55 | | | | | 60 | | | | |

| Lys | Leu | Gly | Trp | Leu | Thr | Pro | Arg | Gly | Gly | Glu | Leu | Ile | Ala | Tyr | Leu |
|---|---|---|---|---|---|---|---|---|---|---|---|---|---|---|---|
| 65 | | | | | 70 | | | | | 75 | | | | | 80 |

| Gly | His | Tyr | Gln | Arg | Gln | Arg | Leu | Val | Ala | Asp | Gly | Leu | Leu | Ala | Lys |
|---|---|---|---|---|---|---|---|---|---|---|---|---|---|---|---|
| | | | | 85 | | | | | 90 | | | | | 95 | |

| Lys | Gly | Cys | Pro | Gln | Ser | Gly | Gln | Val | Ala | Ile | Ile | Ala | Asp | Val | Asp |
|---|---|---|---|---|---|---|---|---|---|---|---|---|---|---|---|
| | | | 100 | | | | | 105 | | | | | 110 | | |

| Glu | Arg | Thr | Arg | Lys | Thr | Gly | Glu | Ala | Phe | Ala | Ala | Gly | Leu | Ala | Pro |
|---|---|---|---|---|---|---|---|---|---|---|---|---|---|---|---|
| | | 115 | | | | | 120 | | | | | 125 | | | |

| Asp | Cys | Ala | Ile | Thr | Val | His | Thr | Gln | Ala | Asp | Thr | Ser | Ser | Pro | Asp |
|---|---|---|---|---|---|---|---|---|---|---|---|---|---|---|---|
| | 130 | | | | | 135 | | | | | 140 | | | | |

| Pro | Leu | Phe | Asn | Pro | Leu | Lys | Thr | Gly | Val | Cys | Gln | Leu | Asp | Asn | Ala |
|---|---|---|---|---|---|---|---|---|---|---|---|---|---|---|---|
| 145 | | | | | 150 | | | | | 155 | | | | | 160 |

| Asn | Val | Thr | Asp | Ala | Ile | Leu | Ser | Arg | Ala | Gly | Gly | Ser | Ile | Ala | Asp |
|---|---|---|---|---|---|---|---|---|---|---|---|---|---|---|---|
| | | | | 165 | | | | | 170 | | | | | 175 | |

| Phe | Thr | Gly | His | Arg | Gln | Thr | Ala | Phe | Arg | Glu | Leu | Glu | Arg | Val | Leu |
|---|---|---|---|---|---|---|---|---|---|---|---|---|---|---|---|
| | | | 180 | | | | | 185 | | | | | 190 | | |

| Asn | Phe | Pro | Gln | Ser | Asn | Leu | Cys | Leu | Lys | Arg | Glu | Lys | Gln | Asp | Glu |
|---|---|---|---|---|---|---|---|---|---|---|---|---|---|---|---|
| | | 195 | | | | | 200 | | | | | 205 | | | |

| Ser | Cys | Ser | Leu | Thr | Gln | Ala | Leu | Pro | Ser | Glu | Leu | Lys | Val | Ser | Ala |
|---|---|---|---|---|---|---|---|---|---|---|---|---|---|---|---|
| | 210 | | | | | 215 | | | | | 220 | | | | |

| Asp | Asn | Val | Ser | Leu | Thr | Gly | Ala | Val | Ser | Leu | Ala | Ser | Met | Leu | Thr |
|---|---|---|---|---|---|---|---|---|---|---|---|---|---|---|---|
| 225 | | | | | 230 | | | | | 235 | | | | | 240 |

| Glu | Ile | Phe | Leu | Leu | Gln | Gln | Ala | Gln | Gly | Met | Pro | Glu | Pro | Gly | Trp |
|---|---|---|---|---|---|---|---|---|---|---|---|---|---|---|---|
| | | | | 245 | | | | | 250 | | | | | 255 | |

| Gly | Arg | Ile | Thr | Asp | Ser | His | Gln | Trp | Asn | Thr | Leu | Leu | Ser | Leu | His |
|---|---|---|---|---|---|---|---|---|---|---|---|---|---|---|---|
| | | | 260 | | | | | 265 | | | | | 270 | | |

| Asn | Ala | Gln | Phe | Tyr | Leu | Leu | Gln | Arg | Thr | Pro | Glu | Val | Ala | Arg | Ser |
|---|---|---|---|---|---|---|---|---|---|---|---|---|---|---|---|
| | | 275 | | | | | 280 | | | | | 285 | | | |

| Arg | Ala | Thr | Pro | Leu | Leu | Asp | Leu | Ile | Lys | Thr | Ala | Leu | Thr | Pro | His |
|---|---|---|---|---|---|---|---|---|---|---|---|---|---|---|---|
| | 290 | | | | | 295 | | | | | 300 | | | | |

| Pro | Pro | Gln | Lys | Gln | Ala | Tyr | Gly | Val | Thr | Leu | Pro | Thr | Ser | Val | Leu |
|---|---|---|---|---|---|---|---|---|---|---|---|---|---|---|---|
| 305 | | | | | 310 | | | | | 315 | | | | | 320 |

| Phe | Ile | Ala | Gly | His | Asp | Thr | Asn | Leu | Ala | Asn | Leu | Gly | Gly | Ala | Leu |
|---|---|---|---|---|---|---|---|---|---|---|---|---|---|---|---|
| | | | | 325 | | | | | 330 | | | | | 335 | |

```
Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 18
<211> LENGTH: 432
<212> TYPE: PRT
<213> ORGANISM: Shigella flexnarii

<400> SEQUENCE: 18

Met Lys Ala Ile Leu Ile Pro Phe Leu Ser Leu Leu Ile Pro Leu Thr
1               5                   10                  15

Ser Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Phe
65                  70                  75                  80

Gly His Tyr Gln Arg Gln Arg Leu Val Ala Asp Gly Leu Leu Ala Lys
                85                  90                  95

Lys Gly Cys Pro Gln Pro Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
            210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285
```

```
Arg Ala Thr Pro Leu Leu Asp Leu Ile Met Ala Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Phe Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 19
<211> LENGTH: 432
<212> TYPE: PRT
<213> ORGANISM: Shigella sonnei

<400> SEQUENCE: 19

Met Lys Ala Ile Leu Ile Pro Phe Leu Ser Leu Ile Pro Leu Thr
1               5                   10                  15

Pro Gln Ser Ala Phe Ala Gln Ser Glu Pro Glu Leu Lys Leu Glu Ser
                20                  25                  30

Val Val Ile Val Ser Arg His Gly Val Arg Ala Pro Thr Lys Ala Thr
            35                  40                  45

Gln Leu Met Gln Asp Val Thr Pro Asp Ala Trp Pro Thr Trp Pro Val
        50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
210                 215                 220

Asp Asn Val Ser Leu Ala Gly Ala Val Ser Leu Ala Ser Met Leu Thr
225                 230                 235                 240
```

-continued

```
Glu Ile Phe Leu Leu Gln Gln Ala Gln Gly Met Pro Glu Pro Gly Trp
            245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
    370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 20
<211> LENGTH: 254
<212> TYPE: PRT
<213> ORGANISM: Pasteurella aerogenes

<400> SEQUENCE: 20

Arg His Gly Val Arg Ala Pro Thr Lys Ala Thr Gln Leu Met Gln Asp
1               5                   10                  15

Val Thr Pro Asp Ala Trp Pro Thr Trp Pro Val Lys Leu Gly Trp Leu
            20                  25                  30

Thr Pro Arg Gly Gly Glu Leu Ile Ala Tyr Leu Gly His Tyr Gln Arg
        35                  40                  45

Gln Arg Leu Val Ala Asp Gly Leu Leu Ala Lys Lys Gly Cys Pro Gln
    50                  55                  60

Ser Gly Gln Val Ala Ile Ile Ala Asp Val Asp Glu Arg Thr Arg Lys
65                  70                  75                  80

Thr Gly Glu Ala Phe Ala Ala Gly Leu Ala Pro Asp Cys Ala Ile Thr
                85                  90                  95

Val His Thr Gln Ala Asp Thr Ser Ser Pro Asp Pro Leu Phe Asn Pro
            100                 105                 110

Leu Lys Thr Gly Val Cys Gln Leu Asp Asn Ala Asn Val Thr Asp Ala
        115                 120                 125

Ile Leu Ser Arg Ala Gly Gly Ser Ile Ala Asp Phe Thr Gly His Arg
    130                 135                 140

Gln Thr Ala Phe Arg Glu Leu Glu Arg Val Leu Asn Phe Pro Gln Ser
145                 150                 155                 160

Asn Leu Cys Leu Lys Arg Glu Lys Gln Asp Glu Ser Cys Ser Leu Thr
                165                 170                 175

Gln Ala Leu Pro Ser Glu Leu Lys Val Ser Ala Asp Asn Val Ser Leu
            180                 185                 190
```

```
Thr Gly Ala Val Ser Leu Ala Ser Met Leu Thr Glu Ile Phe Leu Leu
        195                 200                 205

Gln Gln Ala Gln Gly Met Pro Glu Pro Gly Trp Gly Arg Ile Thr Asp
210                 215                 220

Ser His Gln Trp Asn Thr Leu Leu Ser Leu His Asn Ala Gln Phe Tyr
225                 230                 235                 240

Leu Leu Gln Arg Thr Pro Glu Val Ala Arg Ser Arg Ala Thr
                245                 250
```

<210> SEQ ID NO 21
<211> LENGTH: 253
<212> TYPE: PRT
<213> ORGANISM: Enterobacter cloacae

<400> SEQUENCE: 21

```
Arg His Gly Val Arg Ala Pro Thr Lys Ala Thr Gln Leu Met Gln Asp
1               5                   10                  15

Val Thr Pro Asp Ala Trp Pro Thr Trp Pro Val Lys Leu Gly Trp Leu
            20                  25                  30

Thr Pro Arg Gly Gly Glu Leu Ile Ala Tyr Phe Gly His Tyr Gln Arg
        35                  40                  45

Gln Arg Leu Val Ala Asp Gly Leu Leu Ala Lys Lys Gly Cys Pro Gln
    50                  55                  60

Pro Gly Gln Val Ala Ile Ile Ala Asp Val Asp Glu Arg Thr Arg Lys
65                  70                  75                  80

Thr Gly Glu Ala Phe Ala Ala Gly Leu Ala Pro Asp Cys Ala Ile Thr
                85                  90                  95

Val His Thr Gln Ala Asp Thr Ser Ser Pro Asp Pro Leu Phe Asn Pro
            100                 105                 110

Leu Lys Thr Gly Val Cys Gln Leu Asp Asn Ala Asn Val Thr Asp Ala
        115                 120                 125

Ile Leu Ser Arg Ala Gly Gly Ser Ile Ala Asp Phe Thr Gly His Arg
    130                 135                 140

Gln Thr Ala Phe Arg Glu Leu Glu Arg Val Leu Asn Phe Pro Gln Ser
145                 150                 155                 160

Asn Leu Cys Leu Lys Arg Glu Lys Gln Asp Glu Ser Cys Ser Leu Thr
                165                 170                 175

Gln Ala Leu Pro Ser Glu Leu Lys Val Ser Ala Asp Asn Val Ser Leu
            180                 185                 190

Thr Gly Ala Val Ser Leu Ala Ser Met Leu Thr Glu Ile Phe Leu Leu
        195                 200                 205

Gln Gln Ala Gln Gly Met Pro Glu Pro Gly Trp Gly Arg Ile Thr Asn
    210                 215                 220

Ser His Gln Trp Asn Thr Leu Leu Ser Leu His Asn Ala Gln Phe Tyr
225                 230                 235                 240

Leu Leu Gln Arg Thr Pro Glu Val Ala Arg Ser Arg Ala
                245                 250
```

<210> SEQ ID NO 22
<211> LENGTH: 253
<212> TYPE: PRT
<213> ORGANISM: Enterobacter agglomerans

<400> SEQUENCE: 22

```
Arg His Gly Val Arg Ala Pro Thr Lys Ala Thr Gln Leu Met Gln Asp
1               5                   10                  15

Val Thr Pro Asp Ala Trp Pro Thr Trp Pro Val Lys Leu Gly Trp Leu
```

```
            20                  25                  30
Thr Pro Arg Gly Gly Glu Leu Ile Ala Tyr Leu Gly His Tyr Gln Arg
         35                  40                  45

Gln Arg Leu Val Ala Asp Gly Leu Leu Ala Lys Lys Gly Cys Pro Gln
     50                  55                  60

Pro Gly Gln Val Ala Ile Ile Ala Asp Val Asp Glu Arg Thr Arg Lys
 65                  70                  75                  80

Thr Gly Glu Ala Phe Ala Ala Gly Leu Ala Pro Asp Cys Ala Ile Thr
                 85                  90                  95

Val His Thr Gln Ala Asp Thr Ser Ser Pro Asp Pro Leu Phe Asn Pro
            100                 105                 110

Leu Lys Thr Gly Val Cys Gln Leu Asp Asn Ala Asn Val Thr Asp Ala
        115                 120                 125

Ile Leu Ser Arg Ala Gly Gly Ser Ile Ala Asp Phe Thr Gly His Arg
    130                 135                 140

Gln Thr Ala Phe Arg Glu Leu Glu Arg Val Leu Asn Phe Pro Gln Ser
145                 150                 155                 160

Asn Leu Cys Leu Lys Arg Glu Lys Gln Asp Glu Ser Cys Ser Leu Thr
                165                 170                 175

Gln Ala Leu Pro Ser Glu Leu Lys Val Ser Ala Asp Asn Val Ser Leu
            180                 185                 190

Thr Gly Ala Val Ser Leu Ala Ser Met Leu Thr Glu Ile Phe Leu Leu
        195                 200                 205

Gln Gln Ala Gln Gly Met Pro Glu Pro Gly Trp Gly Arg Ile Thr Asp
    210                 215                 220

Ser His Gln Trp Asn Thr Leu Leu Ser Leu His Asn Ala Gln Phe Tyr
225                 230                 235                 240

Leu Leu Gln Arg Thr Pro Glu Val Ala Arg Ser Arg Ala
                245                 250

<210> SEQ ID NO 23
<211> LENGTH: 290
<212> TYPE: PRT
<213> ORGANISM: Proteus vulgaris

<400> SEQUENCE: 23

Met Lys Ala Ile Leu Ile Pro Phe Leu Ser Leu Leu Ile Pro Leu Thr
 1                5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
```

```
                145                 150                 155                 160
Asn Val Thr Asp Ala Ile Leu Ser Arg Ala Gly Gly Ser Ile Ala Asp
                    165                 170                 175

Phe Thr Gly His Arg Gln Thr Ala Phe Arg Glu Leu Glu Arg Val Leu
                180                 185                 190

Asn Phe Pro Gln Ser Asn Leu Cys Phe Lys Arg Glu Lys Gln Asp Glu
            195                 200                 205

Ser Cys Ser Leu Thr Gln Ala Leu Pro Ser Glu Leu Lys Val Ser Ala
        210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Ile Gln Arg Thr Pro Glu Val Ala Arg Ser
            275                 280                 285

Arg Ala
    290

<210> SEQ ID NO 24
<211> LENGTH: 1299
<212> TYPE: DNA
<213> ORGANISM: Escherichia coli

<400> SEQUENCE: 24
atgaaagcga tcttaatccc attttatct cttctgattc cgttaacccc gcaatctgca      60
ttcgctcaga gtgagccgga gctgaagctg aaagtgtgg tgattgtcag tcgtcatggt     120
gtgcgtgctc aaccaaggc acgcaactg atgcaggatg tcaccccaga cgcatggcca     180
acctggccgg taaaactggg ttggctgaca ccgcgcggtg gtgagctaat cgcctatctc     240
ggacattacc aacgccagcg tctggtagcc gacggattgc tggcgaaaaa gggctgcccg     300
cagtctggtc aggtcgcgat tattgctgat gtcgacgagc gtacccgtaa acaggcgaa     360
gccttcgccg ccgggctggc acctgactgt gcaataaccg tacatcccca ggcagatacg     420
tccagtcccg atccgttatt taatcctcta aaaactggcg tttgccaact ggataacgcg     480
aacgtgactg acgcgatcct cagcagggca ggagggtcaa ttgctgactt accgggcat     540
cggcaaacgg cgtttcgcga actggaacgg gtgcttaatt ttccgcaatc aaacttgtgc     600
cttaaacgtg agaaacagga cgaaagctgt tcattaacgc aggcattacc atcggaactc     660
aaggtgagcg ccgacaatgt ctcattaacc ggtgcggtaa gcctcgcatc aatgctgacg     720
gagatatttc tcctgcaaca agcacaggga atgccggagc cggggtgggg aaggatcacc     780
gattcacacc agtggaacac cttgctaagt ttgcataacg cgcaattta tttgctacaa     840
cgcacgccag aggttgcccg cagccgcgcc accccgttat tagatttgat caagacagcg     900
ttgacgcccc atccaccgca aaacaggcg tatggtgtga cattacccac ttcagtgctg     960
tttatcgccg gacacgatac taatctggca aatctcggcg gcgcactgga gctcaactgg    1020
acgcttcccg gtcagccgga taacacgccg ccaggtggtg aactggtgtt gaacgctgg    1080
cgtcggctaa gcgataacag ccagtggatt caggtttcgc tggtcttcca gactttacag    1140
cagatgcgtg ataaaacgcc gctgtcatta aatacgccgc ccggagaggt gaaactgacc    1200
ctggcaggat gtgaagagcg aaatgcgcag ggcatgtgtt cgttggcagg ttttacgcaa    1260
atcgtgaatg aagcacgcat accggcgtgc agtttgtaa                           1299
```

<210> SEQ ID NO 25
<211> LENGTH: 1299
<212> TYPE: DNA
<213> ORGANISM: Shigella flexnarii

<400> SEQUENCE: 25

| | | | | |
|---|---|---|---|---|
| atgaaagcga | tcttaatccc | attttatct | cttctgattc | cgttaacctc gcaatctgca | 60 |
| ttcgctcaga | gtgagccgga | gctgaagctg | gaaagtgtgg | tgattgtcag tcgtcatggt | 120 |
| gtgcgtgctc | caaccaaggc | cacgcaactg | atgcaggatg | tcaccccaga cgcatggcca | 180 |
| acctggccgg | taaaactggg | ttggctgaca | ccgcgcggtg | gtgagctaat cgcctatttc | 240 |
| ggacattacc | aacgccagcg | tctggtggcc | gacggattgc | tggcaaaaaa gggctgtccg | 300 |
| cagcctggtc | aggtcgcgat | tattgctgat | gtcgacgagc | gtacccgtaa aacaggcgaa | 360 |
| gccttcgccg | ccgggctggc | acctgactgt | gcaataaccg | tacataccca ggcagatacg | 420 |
| tccagtcccg | atccgttatt | taatcctcta | aaaactggcg | tttgccaact ggataatgcg | 480 |
| aacgtgactg | acgcgatcct | cagcagggca | ggagggtcaa | ttgctgactt taccgggcat | 540 |
| cggcaaacgg | cgtttcgcga | actggaacgg | gtgcttaatt | ttccgcaatc aaacttgtgc | 600 |
| cttaaacgtg | agaaacagga | cgaaagctgt | tcattaacgc | aggcattacc atcggaactc | 660 |
| aaggtgagcg | ccgacaatgt | ctcattaacc | ggtgcggtaa | gcctcgcatc aatgctgacg | 720 |
| gagatatttc | tcctgcaaca | agcacaggga | atgccagagc | cggggtgggg aaggatcacc | 780 |
| gattcacacc | agtggaacac | cttgctaagt | ttgcataacg | cgcaattta tttgctacaa | 840 |
| cgcacgccag | aggttgcccg | cagccgcgcc | accccgttat | tggatttgat catggcagcg | 900 |
| ttgacgcccc | atccaccgca | aaaacaggcg | tatggtgtga | cattacccac ttcagtactg | 960 |
| tttattgccg | gacacgatac | taatctggca | aatttcggcg | gcgcactgga gctcaactgg | 1020 |
| acgcttcccg | gtcagccgga | taacacgccg | ccaggtggtg | aactggtgtt tgaacgctgg | 1080 |
| cgtcggctaa | gcgataacag | ccagtggatt | caggtttcgc | tggtcttcca gactttacag | 1140 |
| cagatgcgtg | ataaaacgcc | gctgtcatta | aatacgccgc | ccggagaggt gaaactgacc | 1200 |
| ctggcaggat | gtgaagagcg | aaatgcgcag | ggcatgtgtt | cgttggcagg ttttacgcaa | 1260 |
| atcgtgaatg | aagcacgcat | accggcgtgc | agtttgtaa | | 1299 |

<210> SEQ ID NO 26
<211> LENGTH: 1299
<212> TYPE: DNA
<213> ORGANISM: Shigella sonnei

<400> SEQUENCE: 26

| | | | | |
|---|---|---|---|---|
| atgaaagcga | tcttaatccc | attttatct | cttctgattc | cgttaacccc gcaatctgca | 60 |
| ttcgctcaga | gtgagccgga | gctgaagctg | gaaagtgtgg | tgattgtcag tcgtcatggt | 120 |
| gtgcgtgctc | caaccaaggc | cacgcaactg | atgcaggatg | tcaccccaga cgcatggcca | 180 |
| acctggccgg | taaaactggg | ttggctgaca | ccgcgcggtg | gtgagctaat cgcctatctc | 240 |
| ggacattacc | aacgccagcg | tctggtagcc | gacggattgc | tggcgaaaaa gggctgcccg | 300 |
| cagtctggtc | aggtcgcgat | tattgctgat | gtcgacgagc | gtacccgtaa aacaggcgaa | 360 |
| gccttcgccg | ccgggctggc | acctgactgt | gcaataaccg | tacataccca ggctgatacg | 420 |
| tccagtcccg | atccgttatt | taatcctcta | aaaactggcg | tttgccaact ggataacgcg | 480 |
| aacgtgactg | acgcgatcct | cagcagggca | ggagggtcaa | ttgctgactt taccgggcat | 540 |
| cggcaaacgg | cgtttcgcga | actggaacgg | gtgcttaatt | ttccgcaatc aaacttgtgc | 600 |

| | |
|---|---|
| cttaaacgtg agaaacagga cgaaagctgt tcattaacgc aggcattacc atcggaactc | 660 |
| aaggtgagcg ccgacaatgt ctcattagcc ggtgcggtaa gcctcgcatc aatgctgacg | 720 |
| gagatatttc tcctgcaaca agcacaggga atgccggagc cggggtgggg aaggatcacc | 780 |
| gattcacacc agtggaacac cttgctaagt ttgcataacg cgcaatttta tttgctacaa | 840 |
| cgcacgccag aggttgcccg cagccgcgcc acccgttat tagatttgat caagacagcg | 900 |
| ttgacgcccc atccaccgca aaaacaggcg tatggtgtga cattacccac ttcagtgctg | 960 |
| tttatcgccg gacacgatac taatctggca aatctcggcg gcgcactgga gctcaactgg | 1020 |
| acgcttcccg gtcagccgga taacacgccg ccaggtggtg aactggtgtt tgaacgctgg | 1080 |
| cgtcggctaa gcgataacag ccagtggatt caggtttcgc tggtcttcca gactttacag | 1140 |
| cagatgcgtg ataaaacgcc gctgtcatta aatacgccgc ccggagaggt gaaactgacc | 1200 |
| ctggcaggat gtgaagagcg aaatgcgcag gcatgtgtt cgttggcagg ttttacgcaa | 1260 |
| atcgtgaatg aagcacgcat accggcgtgc agtttgtaa | 1299 |

<210> SEQ ID NO 27
<211> LENGTH: 724
<212> TYPE: DNA
<213> ORGANISM: Pasteurella aerogenes

<400> SEQUENCE: 27

| | |
|---|---|
| tcgtcatggt gtgcgtgctc caaccaaggc cacgcaactg atgcaggatg tcaccccaga | 60 |
| cgcatggcca acctggccgg taaaactggg ttggctgaca ccgcgcggtg gtgagctaat | 120 |
| cgcctatctc ggacattacc aacgccagcg tctggtagcc gacggattgc tggcgaaaaa | 180 |
| gggctgcccg cagtctggtc aggtcgcgat tattgctgat gtcgacgagc gtacccgtaa | 240 |
| aacaggcgaa gccttcgccg ccgggctggc acctgactgt gcaataaccg tacatacccga | 300 |
| ggctgatacg tccagtcccg atccgttatt taatcctcta aaaactggcg tttgccaact | 360 |
| ggataacgcg aacgtgactg acgcgatcct cagcagggca ggagggtcaa ttgctgactt | 420 |
| taccgggcat cggcaaacgg cgtttcgcga actggaacgg gtgcttaatt ttccgcaatc | 480 |
| aaacttgtgc cttaaacgtg agaaacagga cgaaagctgt tcattaacgc aggcattacc | 540 |
| atcggaactc aaggtgagcg ccgacaatgt ctcattaacc ggtgcggtaa gcctcgcatc | 600 |
| aatgctgacg gagatatttc tcctgcaaca agcacaggga atgccggagc cggggtgggg | 660 |
| aaggatcacc gattcacacc agtggaacac cttgctaagt ttgcataacg cgcaatttta | 720 |
| tttg | 724 |

<210> SEQ ID NO 28
<211> LENGTH: 757
<212> TYPE: DNA
<213> ORGANISM: Enterobacter cloacae

<400> SEQUENCE: 28

| | |
|---|---|
| tcgtcatggt gtgcgtgctc caaccaaggc cacgcaactg atgcaggatg tcaccccaga | 60 |
| cgcatggcca acctggccgg taaaactggg ttggctgaca ccgcgcggtg gtgagctaat | 120 |
| cgcctatttc ggacattacc aacgccagcg tctggtggcc gacggattgc tggcaaaaaa | 180 |
| gggctgtccg cagcctggtc aggtcgcgat tattgctgat gtcgacgagc gtacccgtaa | 240 |
| aacaggcgaa gccttcgccg ccgggctggc acctgactgt gcaataaccg tacatacccca | 300 |
| ggcagatacg tccagtcccg atccgttatt taatcctcta aaaactggcg tttgccaact | 360 |
| ggataatgcg aacgtgactg acgcgatcct cagcagggca ggagggtcaa ttgctgactt | 420 |

```
taccgggcat cggcaaacgg cgtttcgcga actggaacgg gtgcttaatt ttccgcaatc    480
aaacttgtgc cttaaacgtg agaaacagga cgaaagctgt tcattaacgc aggcattacc    540
atcggaactc aaggtgagcg ccgacaatgt ctcattaacc ggtgcggtaa gcctcgcatc    600
aatgctgacg gagatatttc tcctgcaaca agcacaggga atgccagagc cggggtgggg    660
aaggatcacc aattcacacc agtggaacac cttgctaagt ttgcataacg cgcaattta    720 tttgctacaa cgcacgccag aggttgcccg cagccgc                            757

<210> SEQ ID NO 29
<211> LENGTH: 757
<212> TYPE: DNA
<213> ORGANISM: Enterobacter agglomerans

<400> SEQUENCE: 29
tcgtcatggt gtgcgtgctc aaccaaggc cacgcaactg atgcaggatg tcacccaga     60 cgcatggcca acctggccgg taaaactggg ttggctgaca ccgcgcggtg gtgagctaat   120
cgcctatctc ggacattacc aacgccagcg tctggtagcc gacggattgc tggcaaaaaa   180
gggctgtccg cagcctggtc aggtcgcgat tattgctgat gtcgacgagc gtacccgtaa   240
aacaggcgaa gccttcgccg ccgggctggc acctgactgt gcaataaccg tacatacca   300 ggcagatacg tccagtcccg atccgttatt taatcctcta aaaactggcg tttgccaact   360
ggataatgcg aacgtgactg acgcgatcct cagcagggca ggagggtcaa ttgctgactt   420
taccgggcat cggcaaacgg cgtttcgcga actggaacgg gtgcttaatt ttccgcaatc   480
aaacttgtgc cttaaacgtg agaaacagga cgaaagctgt tcattaacgc aggcattacc   540
atcggaactc aaggtgagcg ccgacaatgt ctcattaacc ggtgcggtaa gcctcgcatc   600
aatgctgacg gagatatttc tcctgcaaca agcacaggga atgccagagc cggggtgggg   660
aaggatcacc gattcacacc agtggaacac cttgctaagt ttgcataacg cgcaattta    720 tttgctacaa cgcacgccag aggttgcccg cagccgc                            757

<210> SEQ ID NO 30
<211> LENGTH: 868
<212> TYPE: DNA
<213> ORGANISM: Proteus vulgaris

<400> SEQUENCE: 30
atgaaagcga tcttaatccc atttttatct cttctgattc cgttaacccc gcaatctgca    60
ttcgctcaga gtgagccgga gctgaagctg gaaagtgtgg tgattgtcag tcgtcatggt   120
gtgcgtgctc aaccaaggc cacgcaactg atgcaggatg tcacccaga cgcatggcca    180 acctggccgg taaaactggg ttggctgaca ccgcgcggtg gtgagctaat cgcctatctc   240
ggacattacc aacgccagcg tctggtagcc gacggattgc tggcgaaaaa gggctgcccg   300
cagtctggtc aggtcgcgat tattgctgat gtcgacgagc gtacccgtaa aacaggcgaa   360
gccttcgccg ccgggctggc acctgactgt gcaataaccg tacatacca ggctgatacg    420 tccagtcccg atccgttatt taatcctcta aaaactggcg tttgccaact ggataacgcg   480
aacgtgactg acgcgatcct cagcagggca ggagggtcaa ttgctgactt taccgggcat   540
cggcaaacgg cgtttcgcga actggaacgg gtgcttaatt ttccgcaatc aaacttgtgc   600
tttaaacgtg agaaacagga cgaaagctgt tcattaacgc aggcattacc atcggaactc   660
aaggtgagcg ccgacaatgt ctcattaacc ggtgcggtaa gcctcgcatc aatgctgacg   720
gagatatttc tcctgcaaca agcacaggga atgccggagc cggggtgggg aaggatcacc   780
```

```
gattcacacc agtggaacac cttgctaagt ttgcataacg cgcaattta tttgatacaa    840 cgcacgccag aggttgcccg cagccgcg                                      868
```

<210> SEQ ID NO 31
<211> LENGTH: 7
<212> TYPE: PRT
<213> ORGANISM: Escherichia coli
<220> FEATURE:
<221> NAME/KEY: VARIANT
<222> LOCATION: 4, 6
<223> OTHER INFORMATION: Xaa = Any Amino Acid

<400> SEQUENCE: 31

Arg His Gly Xaa Arg Xaa Pro
1               5

<210> SEQ ID NO 32
<211> LENGTH: 253
<212> TYPE: PRT
<213> ORGANISM: Artificial Sequence
<220> FEATURE:
<223> OTHER INFORMATION: synthetic compost enrichment sequence

<400> SEQUENCE: 32

Arg His Gly Val Arg Ala Pro Thr Lys Ala Thr Gln Leu Met Gln Asp
1               5                   10                  15

Val Thr Pro Asp Ala Trp Pro Thr Trp Pro Val Lys Leu Gly Trp Leu
            20                  25                  30

Thr Pro Arg Gly Gly Glu Leu Ile Ala Tyr Leu Gly His Tyr Gln Arg
        35                  40                  45

Gln Arg Leu Val Ala Asp Gly Leu Leu Ala Lys Lys Gly Cys Pro Gln
    50                  55                  60

Ser Gly Gln Val Ala Ile Ile Ala Asp Val Asp Glu Arg Thr Arg Lys
65                  70                  75                  80

Thr Gly Glu Ala Phe Ala Ala Gly Leu Ala Pro Asp Cys Ala Ile Thr
                85                  90                  95

Val His Thr Gln Ala Asp Thr Ser Ser Pro Asp Pro Leu Phe Asn Pro
            100                 105                 110

Leu Lys Thr Gly Val Cys Gln Leu Asp Asn Ala Asn Val Thr Asp Ala
        115                 120                 125

Ile Leu Ser Arg Ala Gly Gly Ser Ile Ala Asp Phe Thr Gly His Arg
    130                 135                 140

Gln Thr Ala Phe Arg Glu Leu Glu Arg Val Leu Asn Phe Pro Gln Ser
145                 150                 155                 160

Asn Leu Cys Leu Lys Arg Glu Lys Gln Asp Glu Ser Cys Ser Leu Thr
                165                 170                 175

Gln Ala Leu Pro Ser Glu Leu Lys Val Ser Ala Asp Asn Val Ser Cys
            180                 185                 190

Thr Gly Ala Val Ser Leu Ala Ser Met Leu Thr Glu Ile Phe Leu Leu
        195                 200                 205

Gln Gln Ala Gln Gly Met Pro Glu Pro Gly Trp Gly Arg Ile Thr Asp
    210                 215                 220

Ser His Gln Trp Ser Thr Leu Leu Ser Leu His Asn Ala Gln Phe Tyr
225                 230                 235                 240

Leu Leu Gln Arg Thr Pro Glu Val Ala Arg Ser Arg Ala
                245                 250

<210> SEQ ID NO 33

```
<211> LENGTH: 754
<212> TYPE: DNA
<213> ORGANISM: Artificial Sequence
<220> FEATURE:
<223> OTHER INFORMATION: synthetic compost enrichment sequence

<400> SEQUENCE: 33
tcgtcatggt gtgcgtgctc caaccaaggc cacgcaactg atgcaggatg tcaccccaga      60
cgcatggcca acctggccgg taaaactggg ttggctgaca ccgcgcggtg gtgagctaat     120
cgcctatctc ggacattacc aacgccagcg tctggtagcc gacggattgc tggcgaaaaa     180
gggctgcccg cagtctggtc aggtcgcgat tattgctgat gtcgacgagc gtacccgtaa     240
aacaggcgaa gccttcgccg ccgggctggc acctgactgt gcaataaccg tacatacccca    300 ggcagatacg tccagtcccg atccgttatt taatcctcta aaaactggcg tttgccaact     360
ggataacgcg aacgtgactg acgcgatcct cagcagggca ggagggtcaa ttgctgactt     420
taccgggcat cggcaaacgg cgtttcgcga actggaacgg gtgcttaatt ttccgcaatc     480
aaacttgtgc cttaaacgtg agaaacagga cgaaagctgt tcattaacgc aggcattacc     540
atcggaactc aaggtgagcg ccgacaatgt ctcactaacc ggtgcggtaa gcctcgcatc     600
aatgctgacg gagatatttc tcctgcaaca agcacaggga atgccggagc cggggtgggg     660
aaggatcacc gattcacacc agtggagcac cttgctaagt ttgcataacg cgcaatttta     720
tttgctacaa cgcacgccag aggttgcccg cagc                                 754
```